United States Patent
Zhang et al.

(10) Patent No.: US 8,986,186 B2
(45) Date of Patent: Mar. 24, 2015

(54) AUTOMATED TREATMENT PLANNING FOR RADIATION THERAPY

(75) Inventors: Xiaodong Zhang, Houston, TX (US);
Xiaoning Pan, Houston, TX (US);
Yupeng Li, Houston, TX (US);
Xiaoqiang Li, Houston, TX (US);
Radhe Mohan, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 477 days.

(21) Appl. No.: 13/212,164

(22) Filed: Aug. 17, 2011

(65) Prior Publication Data

US 2012/0136194 A1 May 31, 2012

Related U.S. Application Data

(60) Provisional application No. 61/374,485, filed on Aug. 17, 2010.

(51) Int. Cl.
*A61N 5/00* (2006.01)
*A61N 5/10* (2006.01)

(52) U.S. Cl.
CPC ............... *A61N 5/103* (2013.01); *A61N 5/1047* (2013.01); *A61N 2005/1087* (2013.01); *A61N 5/1031* (2013.01); *A61N 2005/1041* (2013.01)
USPC ............................................ 600/1

(58) Field of Classification Search
CPC ..................... A61N 5/103–5/1039; A61N 2005/1032–2005/1041

USPC ........ 250/492.1–492.3; 378/64–69, 145–151; 600/1–8
See application file for complete search history.

(56) References Cited

U.S. PATENT DOCUMENTS

| | | | |
|---|---|---|---|
| 6,411,675 B1 * | 6/2002 | Llacer | 378/65 |
| 2002/0080915 A1 * | 6/2002 | Frohlich | 378/65 |
| 2004/0071261 A1 * | 4/2004 | Earl et al. | 378/65 |
| 2004/0120557 A1 | 6/2004 | Sabol et al. | 382/128 |
| 2004/0165696 A1 * | 8/2004 | Lee | 378/65 |
| 2006/0020195 A1 * | 1/2006 | Falco et al. | 600/407 |
| 2006/0067469 A1 * | 3/2006 | Dooley et al. | 378/65 |
| 2007/0076846 A1 * | 4/2007 | Ruchala et al. | 378/65 |
| 2008/0191141 A1 * | 8/2008 | Nilsson | 250/393 |
| 2010/0119032 A1 | 5/2010 | Yan et al. | 378/4 |
| 2011/0124976 A1 * | 5/2011 | Sabczynski et al. | 600/300 |

OTHER PUBLICATIONS

PCT International Search Report and Written Opinion issued in International application No. PCT/US11/48151, dated Dec. 16, 2011.

* cited by examiner

*Primary Examiner* — Catherine B Kuhlman
(74) *Attorney, Agent, or Firm* — Parker Highlander PLLC

(57) ABSTRACT

This patent generally relates to developing treatment plans for use in external beam radiation therapy, and more particularly to a method, a system and a computer readable media that contains programming for the development of external beam radiation therapy treatment plans. Embodiments of the invention include (1) automatically setting beam angles based on a beam angle automation algorithm, (2) judiciously designing planning structures and (3) automatically adjusting the objectives of the objective function based on a parameter automation algorithm.

29 Claims, 39 Drawing Sheets

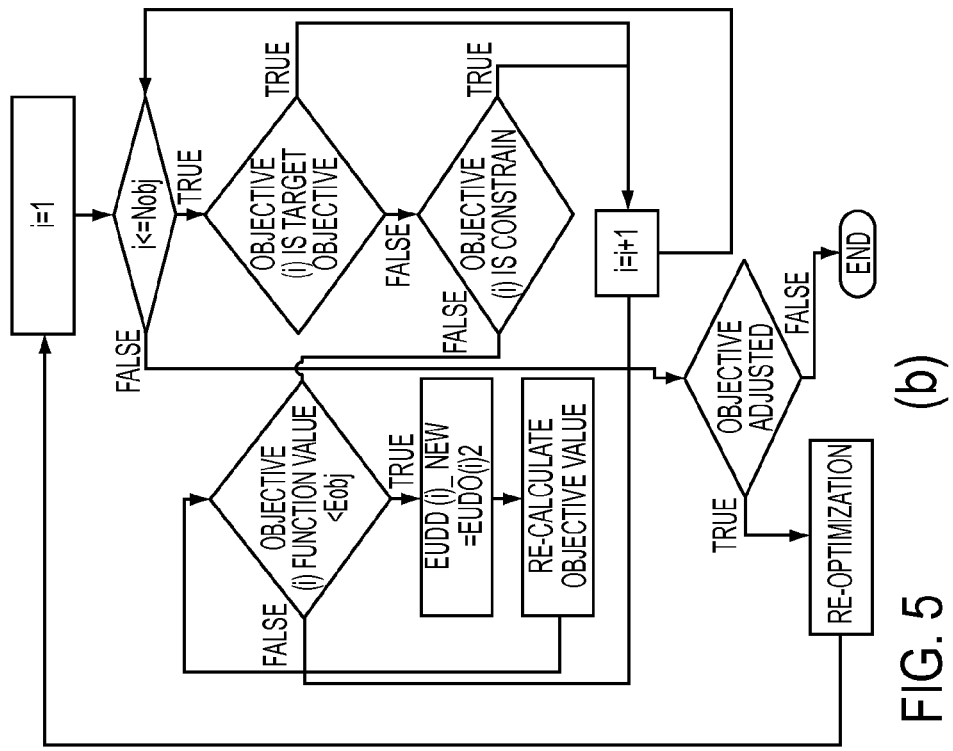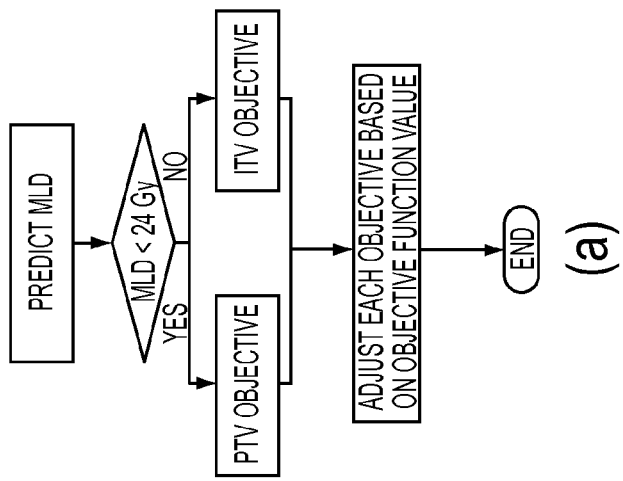
FIG. 5

| ROI | Type | Constrain | Target cGy | % Volume | % Variation | Weight | Objective Value | a |
|---|---|---|---|---|---|---|---|---|
| ◇ FS-PlanPTV | Min Dose | ☑ | 7500 | | | | 0.000176771 | |
| ◆ FS-PlanPTV | Uniform Dose | ☐ | 7500 | | | 100 | 0.246191 | |
| ◇ FS-PlanPTV | Max Dose | ☑ | 7500 | | | | 0.00228514 | |
| ◇ FS-NTAvoid | Max DVH | ☐ | 4000 | 0 | | 10 | 0.0481122 | |
| ◇ FS-LungAvoid | Max EUD | ☐ | 500 | | | 1 | 0.102984 | 1 |
| ◇ FS-CLungAvoid | Max EUD | ☐ | 240 | | | 1 | 0.00644714 | 1 |
| ◇ FS-ILungAvoid | Max EUD | ☐ | 1000 | | | 1 | 0.165728 | 1 |
| ◇ FS-LungAvoid | Max DVH | ☐ | 500 | 15 | | 1 | 0.113524 | |
| ◇ FS-HeartAvoid | Max DVH | ☐ | 4000 | 0 | | 1 | 0.0156748 | |
| ◇ FS-PrvCord | Max DVH | ☑ | 4000 | 0 | | | 0.00135199 | |
| ◇ FS-PrvCordRing | Max DVH | ☐ | 4500 | 0 | | 1 | 2.92992e-05 | |
| ◇ FS-PlanEsoph | Max DVH | ☐ | 4000 | 0 | | 1 | 0.257224 | |
| ◇ FS-NTAvoid | Max Dose | ☑ | 5700 | | | | 4.00138e-05 | |

FIG. 8

| ROI | Type | Constrain | Target cGy | % Volume | % Variation | Weight | Objective Value | a |
|---|---|---|---|---|---|---|---|---|
| ◆ FS-PlanPTV | Uniform Dose | ☐ | 7400 | | | 30 | 0.109919 | |
| ◇ FS-PlanPTV | Max Dose | ☐ | 7400 | | | 15 | 0.0347635 | |
| ◇ FS-PlanPTV | Min Dose | ☐ | 7400 | | | 30 | 0.005538881 | |
| ◇ FS-PTVRing | Max Dose | ☐ | 5600 | | | 20 | 0.0779142 | |
| ◇ FS-NTAvoid | Max Dose | ☐ | 5000 | | | 20 | 0.0166528 | |
| ◇ FS-LungAvoid | Max EUD | ☐ | 400 | | | 0.32 | 0.0824872 | 1 |
| ◇ FS-LungAvoid | Max DVH | ☐ | 500 | 15 | | 0.05 | 0.00741674 | |
| ◇ FS-CLungAvoid | Max EUD | ☐ | 240 | | | 0.05 | 0 | 1 |
| ◇ FS-ILungAvoid | Max EUD | ☐ | 1000 | | | 0.05 | 0.0165024 | 1 |
| ◇ FS-PrvCord | Max EUD | ☐ | 2000 | | | 0.1 | 0.0886904 | 50 |
| ◇ FS-PrvCordRing | Max Dose | ☐ | 300 | | | 6 | 0.00654493 | |
| ◇ FS-HeartAvoid | Max EUD | ☐ | 400 | | | 0.001 | 0.00559422 | 2 |
| ◇ FS-PlanEsoph | Max EUD | ☐ | 900 | | | 0.001 | 0.00653519 | 5 |
| ◇ FS-PlanEsoph | Max Dose | ☐ | 3500 | | | 0.001 | 0.000574722 | |

FIG. 9

| ROI | Type | Constrain | Target cGy | % Volume | % Variation | Weight | Objective Value | a |
|---|---|---|---|---|---|---|---|---|
| ◆ plan_PTV | Uniform Dose ☐ | ☐ | 7900 | | | 0.01 | 4.20887e-06 | |
| ◇ plan PTV | Max Dose ☐ | ☐ | 7900 | | | 0.01 | 1.23287e-07 | |
| ◇ plan PTV | Min Dose ☐ | ☐ | 7900 | | | 0.01 | 4.08668e-06 | |
| ◇ | Max Dose ☐ | ☐ | 7000 | | | 0.005 | 7.63049e-07 | |
| ◇ | Max DVH ☐ | ☐ | 4000 | 0 | | 0.002 | 0.6.38968e-11 | |
| ◇ FS-NormalTIssue ☐ | Max DVH ☐ | ☐ | 4000 | 0 | | 0.01 | 0.80203e-05 | |
| ◇ xxx ☐ | Max EUD ☐ | ☐ | 1600 | | | 0.01 | 0.000533553 | 2 |
| ◇ ☐ | Max EUD ☐ | ☐ | 1600 | | | 0.01 | 0.00270049 | 5 |
| ◇ xxx ☐ | Max EUD ☐ | ☐ | 3500 | | | 0.01 | 0.000124459 | 50 |

FIG. 10

| Display | Index | Type | ROI | Organ/Tumor | End Points/Stage | D50 | Gamma | Alpha Beta | Seriality |
|---|---|---|---|---|---|---|---|---|---|
| ◇ ☑ | 1 | TCP | PTV | NSC Lung | all stages | 4920 | 1 | 10 | |
| ◇ ☑ | 2 | NTCP | heart | Heart | Pericarditis | 4920 | 3 | 3 | 0.2 |
| ◇ ☑ | 3 | NTCP | total lung | Lung | Pneumonities | 2600 | 1.7 | 3 | 0.031 |
| ◇ ☑ | 4 | NTCP | esophagus | Esophagus | Clin Structure | 6800 | 2.3 | 3 | 3.4 |
| ◆ ☑ | 5 | NTCP | cord | Spinal Cord | Myelitis/Necrolytic | 6860 | 1.9 | 3 | 4 |

FIG. 13

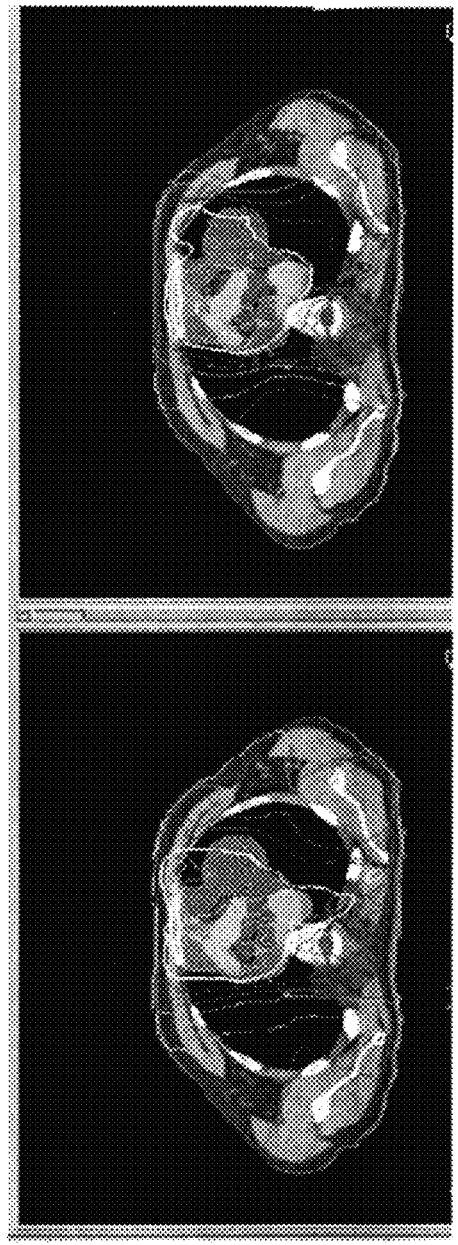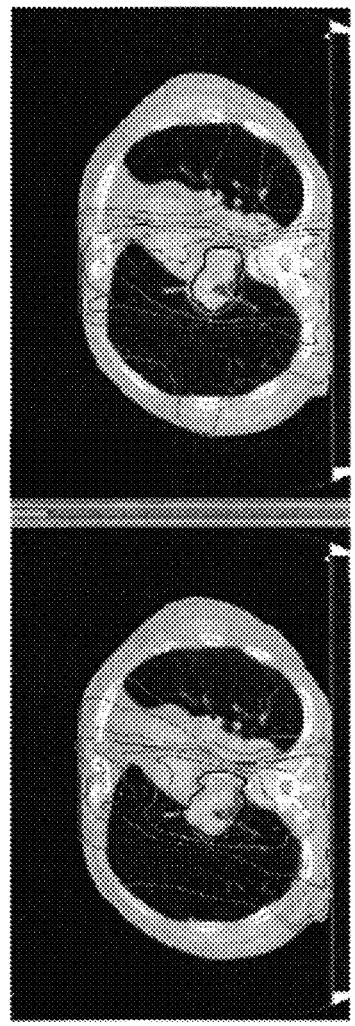
Fig. 19

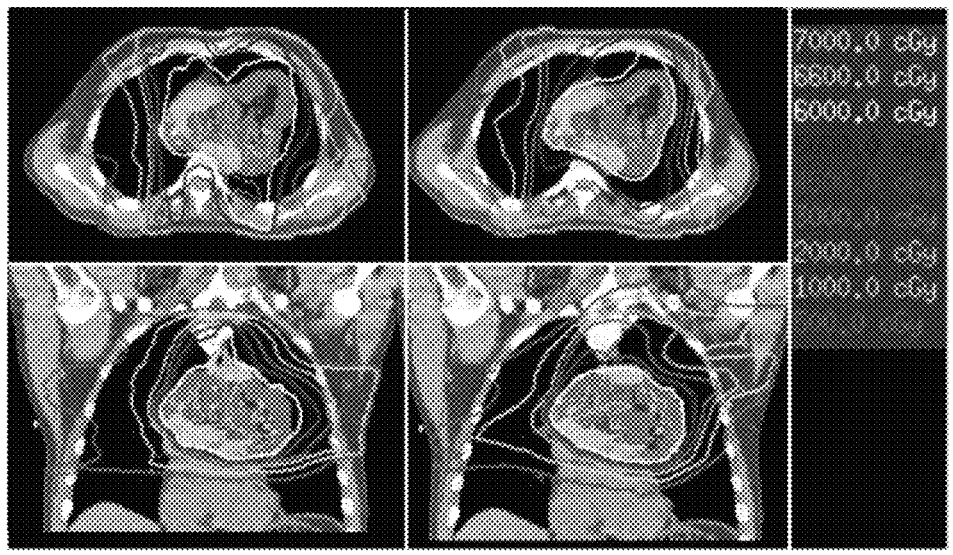
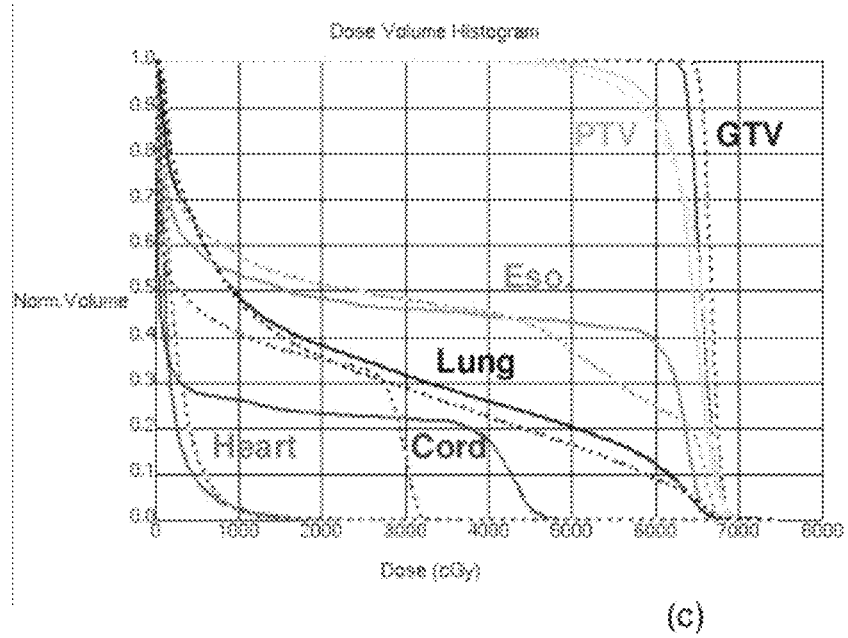
clinical plan: solid (a)   Auto_arc : dashed (b)
(c)
FIG. 31

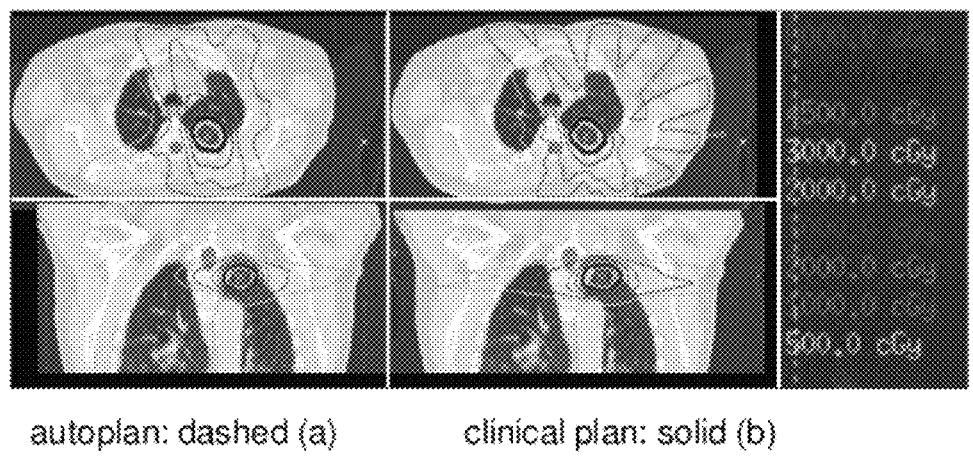
autoplan: dashed (a)   clinical plan: solid (b)
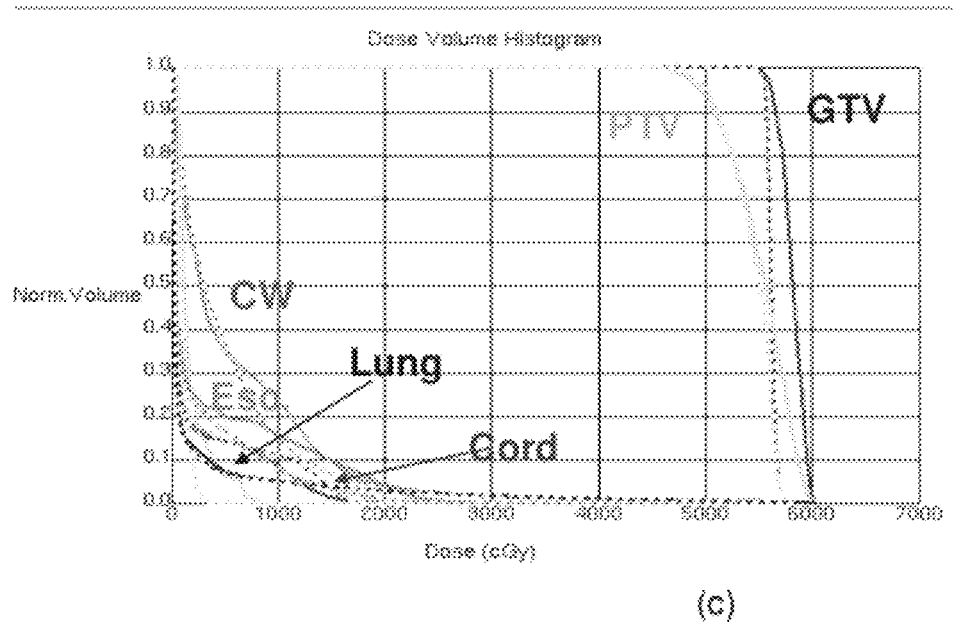
(c)
FIG. 32

FIG. 44

AUTOMATED TREATMENT PLANNING FOR RADIATION THERAPY

CROSS-REFERENCE TO RELATED APPLICATIONS

This application claims the benefit of U.S. Provisional Patent Application Ser. No. 61/374,485, filed Aug. 17, 2010, which is incorporated by reference herein in its entirety.

STATEMENT REGARDING FEDERALLY SPONSORED RESEARCH OR DEVELOPMENT

This invention was made with government support under Grant Number CA 16672 awarded the National Institutes of Health. The United States Government has certain rights in the invention.

TECHNICAL FIELD

The present invention relates generally to developing treatment plans for use in external beam radiation therapy, and more particularly to a method, a system and a computer readable media that contains programming for the development of external beam radiation therapy treatment plans, for treating patients in need of radiation therapy.

BACKGROUND OF THE INVENTION

Efforts to make radiotherapy treatment better, faster, and more cost effective have been underway since radiation was first used to treat cancer. The current radiation treatment workflow is mostly human based. First is a diagnostics/staging step where patients go through imaging, biopsy, CT/PET simulation and the staging of the cancer. A tumor definition and prescription is then outlined by a Radiation Oncologist, who draws the tumor contour based on imaging techniques such as CT/PET/MRI and gives the "prescription" dosages to a dosimetrist. The dosimetrist, or other such expert, then outlines the treatment planning which includes 1) drawing the contours of region of interests such as heart, cord, esophagus etc., (this can also be done by auto segmentation and graphical tools); 2) designing the beam directions and angles based on trial and error; 3) optimizing the beam intensities using objection function parameters based on trial and error; and 4) checking the plan with the radiation oncologist to determine if the plan is acceptable. If the plan is not accepted by the radiation oncologist, the radiation oncologist will ask the dosimetrist to modify the plan. The dosimetrist will then repeat the previous steps. Once the Radiation oncologist accepts the plan, the dosimetrist compiles all of the plan information and sends the plan to a delivery database and/or clinical station. Physicists check, quality assure and approve the plan. The therapy may be divided into fractions, (one per day, 5 days per week, for example). A radiation therapist uses the final plan to deliver the treatment to the patient.

Although IMRT treatment planning methods have improved continuously over the years, IMRT treatment planning is still a complex process that depends strongly on the medical dosimetrist's experience (Schwarz 2009). For instance, the dosimetrist specifies beam directions based on past experience and trial-and-error, and then specifies objectives for dose distribution using single dose values, a few dose—volume points, or fully flexible dose—volume histograms (DVHs). Objectives may be weighted based on their importance. The planning system represents these objectives in a cost function, which must be maximized or minimized using an optimization algorithm. The cost function numerically attempts to represent the tradeoffs that are incorporated into clinical judgment. If the dosimetrist wants to change the outcome, he or she can iteratively alter the objectives and re-optimize. However, it is difficult to translate clinical requirements into a cost function and 'steer' the optimization toward the best result. As a result, IMRT planning can be a time-consuming and frustrating task, and the quality of treatment plans with similar target dose prescriptions and normal tissue constraints will vary between treatment dosimetrists and institutions (Schwarz 2009).

It is believed that the plan quality improvement is significant to improve the overall radiation therapy healthcare quality. Although IMRT can provide better outcomes for some cancers, the clinical benefits of this treatment can be compromised by sub-optimal treatment planning. In 2003, Forster, Smythe et al. 2003 reported that IMRT could provide a local control rate of greater than 80%, with acute toxicity below grade 3, in pleural mesothelioma, a largely fatal disease with an aggressive clinical course and a high mortality rate. This technology was immediately adopted by Mass General Hospital (MGH). Allen et al. (Allen, Czerminska et al. 2006) subsequently reported fatal (grade>=4) thoracic radiation penumonities (TRPs) in 6 of 13 patients receiving IMRT treatment. After much debate, (Komaki, Liao et al. 2006; Allen and Baldini 2007; Allen, Schofield et al. 2007; Rodrigues and Roa 2007; Veldeman, Madani et al. 2008) it was concluded that the high TRPs seen by Allen et al. may have been due to less strict treatment planning objectives. Importantly, Veldeman et al. (Veldeman, Madani et al. 2008) used a similar technique to that of MDACC (MD Anderson Cancer Center) and did not observe fatal TRPs. Veldeman et al. concluded that "we operate at the verge of what is clinically tolerable. Such an aggressive regimen should therefore only be delivered within strictly defined protocols, with rigorous quality control and potential candidates selected with extreme caution." From the above description, it can be speculated that the quality of IMRT planning varies from institution to institution, and only the best designed IMRT plans offer therapeutic advantages. It can also be speculated that if the AutoPlan system would be available to MGH at the time when they adopted the mesothelioma treatment technology, it would be possible that fatal radiation damage to patients could have been avoided.

With the IMRT technique available to more and more community setting hospitals, it is very hard to ensure the plan quality. There is a long learning curve for IMRT planners, demonstrated in quality comparisons between new and seasoned dosimetrists. This learning curve was confirmed (Chung, Lee et al. 2008) by a recent plan quality comparison study for same plans designed by National University Hospital, Singapore and University of California-San Francisco. After this study, Chung et. al. concluded that "our IMRT plans were not able to fully maximize the potential dosimetric gains of IMRT over 3DCRT". Even for the big institution like MDACC, the learning cure for a new technology is also not very short. For example, the first case of mesothelioma case treated in MDACC took 8 weeks from simulation to treatment. After four years experiences on the planning constrains and beam angle selections, the treatment planning time was reduced to 1 week. It can be imagined that it is almost impossible to let community hospital to perform those complex treatments if they started from scratch. The AutoPlan system will be a vehicle to rapidly spread the newest treatment technologies to more radiation therapy facilities.

Embodiments of the invention presented here, including a method, system and computer readable medium designs a treatment plan in order to improve the quality and consistency of treatment planning. This method 1) automatically sets beam angles based on a beam angle automation (BAA) algorithm that is expert system based, and/or 2) automatically adjusts the objectives of the objective function based on an objective function parameter automation (OFPA) algorithm. The treatment plan provides methods for delivering a prescribed radiation dose to a predefined target volume while attempting to avoid giving large dose to tissue and organs surrounding the target volume.

Embodiments of the present invention relate to a novel method to select beam-angles and objective-function parameters in order to create an optimized treatment plan. A goal is to set beam-angle and objective/cost function parameters. The algorithm is executed in a reasonable time frame so that it can be used in routine clinical practice. Other methods, systems, features and advantages of the present invention will be or become apparent to one with skill in the art upon examination of the following drawings and detailed description.

BRIEF SUMMARY OF THE INVENTION

The invention relates to a method, a system and a computer readable medium that contains programming for the development of external beam radiation therapy treatment plans.

A general embodiment of the invention is a method for developing a treatment plan for radiation therapy, the method comprising: receiving information corresponding to a tumor position in a patient; selecting a plurality of beam angles based on the tumor position using an expert system; receiving information corresponding to a plurality of constrained and unconstrained objective function parameters related to at least one of a minimum and maximum radiation dosage to a specific region of interest; selecting each of the selected beam angle's intensities based, in part, on the objective function parameters; selecting new unconstrained objective function parameters based, in part, on the previous unconstrained objective function parameter; selecting new beam intensities based, in part, on the new unconstrained objective function parameters and treating the patient with the selected beam intensities. In an embodiment of the invention, the new beam intensities are selected more than twice. In this embodiment, each new beam intensity is selected based in part on the new objective function parameters. In a specific embodiment of the invention, the expert system includes information on a plurality of patients' tumor position, tumor size, general tumor site and beam angles used to treat the tumor position. In a further embodiment of the invention, the tumor position is the relative coordinate between the marked iso-center of a tumor and the center of a planning target volume. In a specific embodiment of the invention, expert database includes information on the outcome of radiation treatment on a patient.

In another embodiment of the invention, the objective function parameter is represented by an objective function parameter value calculated using EUD, TCP, NTCP, dose and dose-volume. An embodiment of the invention may also comprise removing at least one beam angle and selecting new beam intensities for the remaining beam angles. In another embodiment of the invention, the method additionally comprises comparing the treatment plan before and after removing the at least one beam angle; and adding the removed beam angle back into the treatment plan if the selected new beam intensities result in a total objective function value greater than a previous total objective function value. Additionally, the expert system may comprise one patient, at least 5 patients, at least 10 patients, at least 50 patients, at least 100 patients, at least 150 patients, at least 200 patients, at least 300 patients, at least 400 patients, at least 500 patients, at least 1000 patients, at least 1500 patients, or at least 2000 patients. Many different numbers of beam angles may be selected in a specific embodiment of the invention, such as at least 5, 6, 7, 8, 9, 10, 11, 12, 13, 14, 15, 16, 17, 18, or 19 beams or one or two arc angles are selected. In a specific embodiment of the invention, the selected beam angles are a mix of both coplanar and non-coplanar angles, the selected beam angles are arc angles, the selected beam angles are coplanar, or the selected beam angles are non-coplanar. In a further embodiment of the invention, the selected beam angles are the beam angles used to treat the tumor location in a patient in the expert system with the closest tumor location to the tumor position. The selected beam angles may also be selected from beam angles with the highest frequency distribution in a set of patients in the expert system with tumor locations in the general organ location of the tumor position, in one embodiment.

In a specific embodiment of the invention, the general organ location is the same side of the organ the tumor position is located in. In another embodiment of the invention, the general organ location is the same quadrant of the organ the tumor position is located in. The treatment plan may also comprise multiple treatments, in an embodiment of the invention. In a further embodiment of the invention, after a treatment within the multiple treatments, new information corresponding to the tumor position is received and new beam angles selected from the expert system. In another embodiment of the invention after a treatment within the multiple treatments, new information corresponding to the tumor position is received and new objective functional parameters are selected. In another embodiment, the tumor position is a lung tumor, a brain tumor, a prostate tumor, a gynecological tumor, a head and neck tumor a gastrointestinal tumor, an esophagus tumor, an anal tumor, a mesothelioma tumor, or a breast tumor.

In a further embodiment, the tumor positions are represented by integrated target volume. In an additional embodiment of the invention, the method additionally comprises: estimating the mean organ dose based on the tumor size and overlapping between tumor and normal organ; determining if the mean organ dose is above or below a set value; using integrated target volume tumor positions to select the functional parameters if the mean organ dose is above the set value. In an embodiment of the invention, the regions of interest are selected from a group consisting of the tumor location, any organ located near the tumor location, and any combination thereof. In another embodiment of the invention, the radiation therapy is selected from the group consisting of intensity modulated radiation treatment, intensity modulated proton therapy treatment, and volumetric modulated arc therapy.

In certain embodiments of the invention, the objective function parameters are selected from the group consisting of planning target volume minimum dose, planning target volume uniform dose, planning target volume maximum dose, minimum planning target dose volume, maximum planning target dose volume, organ avoidance maximum dose, maximum organ avoidance dose volume, and any combination thereof. In further embodiments of the invention, constrained objection function parameters are selected from the group consisting of planning target volume minimum dose, planning target volume maximum dose, planning target volume dose, maximum normal tissue dose, maximum cord dose volume, and any combination thereof. In other embodiments of the invention, organ avoidance maximum doses are selected from the group consisting of maximum lung avoidance EUD, maximum heart avoidance dose volume, maximum heart avoidance EUD, contra-lateral lung dose volume, maximum esophagus avoidance dose volume, maximum esophagus avoidance EUD and any combination thereof. In specific embodiments of the invention, non-constrained objection function parameters are selected from the group consisting of planning target volume minimum dose, planning target volume uniform dose, planning target volume maximum dose, minimum planning target volume dose-volume, maximum normal tissue dose, maximum cord dose volume, maximum lung avoidance EUD, maximum heart avoidance dose volume, maximum contra-lateral lung dose volume, maximum esophagus avoidance dose volume, and any combination thereof. In an additional embodiment of the invention, selecting new unconstrained objective function parameters comprises: calculating the objective function parameter value; comparing the objective function parameter value to a maximum sub-objective function value; and adjusting the value of the objective functional parameter to be less or greater than the current objective function parameter if the sub-objective function parameter value is less than the maximum sub-objective function value. In specific embodiments of the invention, an objective function parameter is represented by the parameters: EUD0, dose, dose-volume, weight, and alpha. In an embodiment of the invention, the objective function parameter value is calculated from the EUD, dose, dose-volume, weight and alpha parameters. In a further embodiment of the invention, the method is repeated until a total objective value calculated from the sum of the individual objective function parameters is the same as or greater than a previous total objective value. In another embodiment of the invention, multiple treatment plans are generated by weighing each objective functional parameter differently. An additional embodiment of the invention comprises a tool for navigation and selection of a final plan based on multiple plans. In a further embodiment of the invention, the multiple treatment plans are IMRT plans and a final treatment plan is a VMAT plan. In a specific embodiment of the invention, at least two of the multiple treatment plans are combined to produce a final treatment plan. In another embodiment of the invention, a final treatment plan is an IMRT plan or a VMAT plan. In a further embodiment of the invention, multiple treatment plans are generated by testing the competition of individual objectives.

A general embodiment of the invention is a method for selecting an orientation of a treatment beam in radiation therapy, the method comprising: receiving information corresponding to a tumor position; selecting at least one beam angle based on the tumor position using an expert system; and treating a patient with the at least one selected beam angle. In a specific embodiment of the invention, the selected beam angles are a mix of both coplanar and non-coplanar, the selected beam angles are coplanar, the selected beam angles are non-coplanar, or the selected beams are arc angles. In another embodiment of the invention, the expert system includes information on a plurality of patients' tumor position, tumor size, general tumor site and beam angles used to treat the tumor location. In an embodiment of the invention, the selected beam angles are the beam angles used to treat the tumor location in a patient in the expert system with the closest tumor location to the tumor position. In a further embodiment of the invention, the selected beam angles are selected from beam angles with the highest frequency distribution in a set of patients in the expert system with tumor locations in the general organ location of the tumor position.

Another general embodiment of the invention a system for generating treatment plans for radiation therapy, the system comprising a processor in communication with a memory, where the memory stores processor-executable program code and the processor is configured to be operative in conjunction with the processor-executable program code to: receive information specifying a tumor position; interface to an expert database to receive therefrom a plurality of treated tumor positions and beam angles used to treat the respective treated tumor position; select a plurality of beam angles based on the tumor position using the expert database; receive a plurality of constrained and unconstrained objective function parameters related to a radiation dosage to at least one region of interest; select beam intensities for each of the selected beam angles from the beam selection module based, in part, on the objective function parameters; modify the unconstrained objective function parameters; send the plurality of beam angles and beam intensities to a radiation treatment system. The embodiment may further comprise a treatment plan navigation module configured to display multiple treatment plans. In another embodiment of the invention comprises a treatment plan navigation module configured to for selecting a best compromised plan based on multiple plans.

A general embodiment of the invention is a computer readable medium comprising computer-usable program code executable to perform operations comprising: receiving information corresponding to a tumor position; selecting a plurality of beam angles based on the tumor position using an expert system; receiving information corresponding to a plurality of constrained and unconstrained objective function parameters related to at least one of a minimum and maximum radiation dosage to a specific region of interest; selecting each of the selected beam angle's intensities based, in part, on the objective function parameters; selecting new unconstrained objective function parameters; and selecting new beam intensities based, in part, on the new unconstrained objective function parameters.

General embodiments of the invention are to a method of forming a treatment plan for treating a patient with radiation therapy and/or a computer readable medium comprising computer-usable program code executable to perform operations, the method comprising and computer readable medium comprising: receiving information corresponding to a tumor position in the patient determined using an imaging device; selecting a plurality of beam angles for a respective plurality of beams based on the tumor position; receiving information corresponding to a plurality of constrained and unconstrained objective function parameters related to at least one of a minimum and maximum radiation dosage to a specific region of interest; selecting an intensity for each beam based, in part, on the objective function parameters; selecting new unconstrained objective function parameters based, in part, on the previous unconstrained objective function parameters; and selecting new beam intensities based, in part, on the new unconstrained objective function parameters. This general embodiment of the invention may also be a system for generating treatment plans for radiation therapy, the system comprising a processor in communication with a memory, where the memory stores processor-executable program code and the processor is configured to be operative in conjunction with the processor-executable program code to perform the steps listed above.

The plurality of beam angles may be selected using an expert system. The expert system may include information on a plurality of patients' tumor position, tumor size, general tumor site and beam angles used to treat the tumor position. The tumor position may be the relative coordinate between the marked iso-center of a tumor and the center of a planning target volume. The expert database may include information on the outcome of radiation treatment on a patient. The objective function parameter may be represented by an objective function parameter value calculated using EUD, TCP, NTCP, dose and dose-volume. The method may additionally comprise removing at least one beam and selecting new beam intensities for the remaining beams. The method may additionally comprise comparing the treatment plan before and after removing the at least one beam angle; and adding the removed beam angle back into the treatment plan if the selected new beam intensities results in a total objective function value greater than a previous total objective function value. The beam angles may be selected using expert system beam angles used to treat a tumor location in a patient in the expert system who has the closest tumor location to the tumor position. The selected beam angles may be selected from beam angles with the highest frequency distribution in a set of patients in the expert system with tumor locations in the general organ location of the tumor position.

Additionally, embodiments of the invention include that the treatment plan comprises multiple treatments. In certain embodiments, after a treatment within the multiple treatments, new information corresponding to the tumor position is received and new beam angles selected from the expert system. In another embodiment, after a treatment within the multiple treatments, new information corresponding to the tumor position is received and new objective functional parameters are selected. The new beam intensities may be selected more than twice. The plurality of beams may be used to treat the patient.

In embodiments of the invention, the tumor positions are represented by integrated target volume. The method may additionally comprise estimating the mean organ dose based on the tumor size and overlapping between tumor and normal organ; determining if the mean organ dose is above or below a set value; using integrated target volume tumor positions to select the functional parameters if the mean organ dose is above the set value.

In embodiments of the invention, The objective function parameters are selected from the group consisting of planning target volume minimum dose, planning target volume uniform dose, planning target volume maximum dose, minimum planning target dose volume, maximum planning target dose volume, organ avoidance maximum dose, maximum organ avoidance dose volume, and any combination thereof. The constrained objection function parameters may be selected from the group consisting of planning target volume minimum dose, planning target volume maximum dose, planning target volume dose, maximum normal tissue dose, maximum cord dose volume, and any combination thereof. The regions of interest may be selected from a group consisting of the tumor location, any organ located near the tumor location, and any combination thereof. The radiation therapy may be selected from the group consisting of intensity modulated radiation treatment, intensity modulated proton therapy treatment, and volumetric modulated arc therapy. The selecting new unconstrained objective function parameters may comprises: calculating the objective function parameter value; comparing the objective function parameter value to a maximum sub-objective function value; and adjusting the value of the objective functional parameter to be less or greater than the current objective function parameter if the sub-objective function parameter value is less than the maximum sub-objective function value. An objective function parameter may be represented by the parameters: EUD0, dose, dose-volume, weight, and alpha. The method may be repeated until a total objective value calculated from the sum of the individual objective function parameters is the same as or greater than a previous total objective value.

In additional embodiments of the invention, multiple treatment plans are generated by weighing each objective functional parameter differently. An embodiment of the invention may additionally comprise a tool for navigation and selection of a final plan based on multiple plans. In other embodiments of the invention, the multiple treatment plans are IMRT plans and a final treatment plan is a VMAT plan. At least two of the multiple treatment plans may be combined to produce a final treatment plan. The final treatment plan may be an IMRT plan or a VMAT plan. An embodiment may additionally comprise selecting a best compromised plan based on multiple plans.

An embodiment of the invention is also a computer readable medium comprising computer-usable program code executable to perform operations comprising: receiving information corresponding to a tumor position in the patient determined using an imaging device; selecting a plurality of beam angles for a respective plurality of beams based on the tumor position; receiving information corresponding to a plurality of constrained and unconstrained objective function parameters related to at least one of a minimum and maximum radiation dosage to a specific region of interest; selecting an intensity for each beam based, in part, on the objective function parameters; selecting new unconstrained objective function parameters based, in part, on the previous unconstrained objective function parameters; and selecting new beam intensities based, in part, on the new unconstrained objective function parameters.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings, in which:

FIGS. 5A and 5B are flowcharts of an embodiment of the objective function parameter automation (OFPA) algorithm.

FIG. 8 is a screen shot of the planning structures and initial objective function parameters used in some embodiments of lung plans for the AutoPlan System. The columns from left to right represent region of interest, type of objective functional parameter, whether the objective function parameter is constrained, the EUD/Dose value, Volume, value if dose volume objective function is used, the weight applied to the objective function parameter, the objective value, and the parameter alpha if EUD objective function is used.

FIG. 9 is a screen shot of the planning structures and initial objective function parameters used in some embodiments of lung plans for the AutoPlan System.

FIG. 10 is a screen shot of the planning structures and initial objective function parameters used in some embodiments of prostate plans for the AutoPlan System.

FIG. 13 is a screenshot of the parameters used to calculate the TCP and NTCP values for cancer patients in AutoPlan.

FIG. 19 shows comparison of iso-dose distributions of the plans generated with/without some planning structures. Iso-dose of the plan with (a) and without (b) FS-CordRing structures. The FS-CordRing was shown with Pink colorwash. Iso-dose-distribution of the plans with (c) and without (d) FS-ClungAvoid structure.

FIG. 31 illustrates dose distributions represented by iso-dose lines form clinical fixed beam IMRT plan (a) and autoplan using VMAT technologies (b). (c) illustrates the DVHs comparisons between clinical fixed beam IMRT plan (solid line) and autoplan using VMAT technologies (c).

FIG. 32 illustrates dose distributions represented by iso-dose lines from SBRT autoplans using VMAT technologies (a); clinical SBRT plans (b) and SBRT plan designed by an experienced medical physicist (c).

FIG. 44 is the p values for the differences between doses delivered by the VMAT plans and those delivered by the various IMRT plans.

DETAILED DESCRIPTION OF THE INVENTION

I. Definitions

Figure 1:
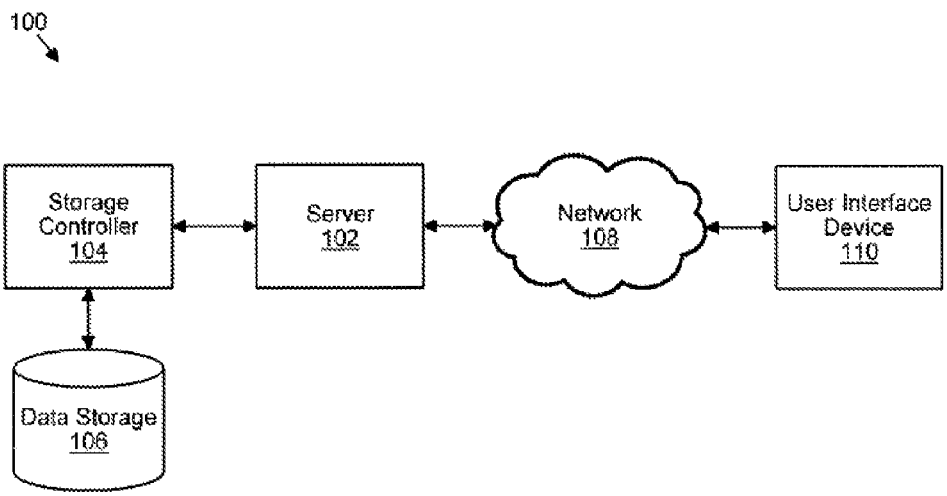
FIG. 1 is a schematic block diagram illustrating one embodiment of a system for generating radiation oncology treatment plans.

"Tumor position" or "tumor location" as used herein refers to the area of the body that the tumor is located in. Generally, the tumor position may relate to an organ area. More specifically, the tumor position may be given by an imaging contour. The tumor position may also be given by the relative coordinate between marked iso-center of a tumor and a planning target volume (PTV), or an integrated target volume (ITV).

"Beam angles" as used herein relates to the angles that the external beams are set within a tumor plan to converge on a tumor position. The beam angles may be coplanar or non-coplanar. Non-coplanar beam angles include both the angle of the beams and the angle of the couch that the patient is positioned on. For volumetric arc therapy, the beam angles refer to arc angles.

"Expert system" as used herein refers to a database that contains information of previously treated tumors. The expert system may contain information on the tumor position, the beam angles and intensities used to treat the tumor position, patient information, and treatment results, for example. The expert system is generated by saving patient treatment data into the database, thereby creating a large collection of patient treatment information. The expert system may be reviewed by one of skill in the art to remove entries in the database that contain inconsistencies, redundancies or other such information that the person of skill in the art deems unnecessary to the expert system. In an embodiment of the invention, the expert system is used to automatically select beam angles. In an embodiment of the invention, the expert system contains one entry, greater than five entries, greater than ten entries, greater than 20 entries, greater than 50 entries, greater than 100 entries, greater than 150 entries, or greater than 200 entries of beam angles. The expert system may contain beam angles for one location of tumor, such as lung tumors, or may contain beam angles for a plurality of tumor locations and types.

"Objective function parameters" as used herein refers to the designed goals of radiotherapy treatment which are defined and achieved by the selection of objective function parameters (OFPs). These OFPs may include dose levels (D0) and percent of volume exceeding/under (Max DVH/Min DVH type) these levels; maximum, or minimum doses; maximum or minimum equivalent uniform doses (EUD0) and the parameters specifying EUDs; and the parameters specifying relative importance of the various objectives. For example, for lung tumor treatment the objective function parameters may be EUD0=10 Gy, weight=100, a=1 with objective parameter type Max EUD, which may be specified as maximum EUD value with EUD parameter a=1 of lung which may not exceed EUD0(10 Gy) with importance weight=100 for lung.

"Objective function value" is a number or equation that represents an objective function parameter. For example, the objective function value may be calculated from EUD, dose based and dose volume based.

"Constrained parameter" refers to an objective function parameter that may not be modified.

"Unconstrained parameter" refers to an objective function parameter that may be modified.

"Eobj" refers to a user adjustable objective function value used by the AutoPlan system to control the convergence of the objective function parameter optimization algorithm. Eobj=0.2 may be used for most non-constrained objectives. It was found that when an objective function value exceed Eobj=0.2 it may lead to the degradation of other objectives. In some embodiments of the invention, Eobj is about equal to 0.2. In embodiments of the invention, the Eobj is between 0.1 and 0.3, or 0.15 and 0.25.

"Radiation dosage" as used herein refers to the amount of radiation that is delivered to a patient. A radiation dosage may be given for multiple regions of interest, such as a prescribed radiation dosage to a tumor, or a max radiation dosage may be given for surrounding normal tissue.

"Region of interest" as used herein refers to a specific region of interest within a patient. For example, the region of interest may refer to the tumor location, or the region of interest may refer to surrounding normal tissue and organs.

"Beam intensities" as used herein refers to the varying intensity maps from the beam angles to modulate the dose to the patient.

"AutoPlan" as used herein refers to the AutoPlan program, system and method that is described herein to generate radiation therapy treatment plans. AutoPlan may include both beam angle selection and/or functional parameter optimization.

An "autoplan treatment plan" or "autoplan" as used herein refers to radiation therapy treatment plans that are developed using the AutoPlan program.

EUD as used herein refers to an equivalent uniform dose. EUD was designed to summarize and report nonhomogeneous dose distributions. Two doses are considered to be equivalent if they cause the same radiobiological effect, regardless of the actual structure of the dose itself.

"Alpha" as used herein refers to one of the parameters used to define the EUD. When alpha is equal to infinity, EUD is the maximal dose to the tissue area; when alpha is equal to negative infinity, EUD is the minimal dose; when alpha is equal to 1, EUD is the arithmetic mean dose.

"Planning target volume" (PTV) as used herein refers to principal tumor volume or primary treatment volume, which is the fixed subset of voxels determined by a clinician to contain a cancerous tumor for treatment. This subset is chosen to account for possible uncertainties which the treatment may incur; including internal organ shifting, patient movement during treatment, and inaccuracies in detection. The PTV should have a high probability of containing the tumor for the entire treatment.

"Integrated target volume" or "internal target volume" (ITV) as used herein is the envelope needed to enclose the target as it moves throughout the breathing cycle. Clinical target volume (CTV) may also be used for this representation. The gross target volume (GTV) is the subset of voxels containing the highest density of tumor cells, and can be thought of as the main body of the tumor. However, since this may not account for some cancerous cells outside of the high density regions, clinicians typically add a margin of error to the GTV to create the CTV, which would most likely contain all cancerous cells which require treatment.

"Competitive objective" as used herein refers to an instance of improving one objective only to degrade another objective. These two objectives are considered competitive objectives. Otherwise, these two objectives are considered non-competitive objectives.

"Selecting" comprises calculating in some embodiments, and may be characterized as 'determining.'

Certain units described in this specification have been labeled as modules, in order to more particularly emphasize their implementation independence. A module is "[a] self-contained hardware or software component that interacts with a larger system." Alan Freedman, "The Computer Glossary" 268 (8th ed. 1998). A module comprises a machine or machines executable instructions. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also include software-defined units or instructions, that when executed by a processing machine or device, transform data stored on a data storage device from a first state to a second state. An identified module of executable code may, for instance, comprise one or more physical or logical blocks of computer instructions which may be organized as an object, procedure, or function. Nevertheless, the executables of an identified module need not be physically located together, but may comprise disparate instructions stored in different locations which, when joined logically together, comprise the module, and when executed by the processor, achieve the stated data transformation.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices.

In the following description, numerous specific details are provided, such as examples of programming, software modules, user selections, network transactions, database queries, database structures, hardware modules, hardware circuits, hardware chips, etc., to provide a thorough understanding of the present embodiments. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

FIG. 1 illustrates one embodiment of a system 100 for generating radiation therapy treatment plans. The system 100 may include a server 102, a data storage device 104, a network 108, and a user interface device 110. In a further embodiment, the system 100 may include a storage controller 106, or storage server configured to manage data communications between the data storage device 104, and the server 102 or other components in communication with the network 108. In an alternative embodiment, the storage controller 106 may be coupled to the network 108.

In one embodiment, the user interface device 110 is referred to broadly and is intended to encompass a suitable processor-based device such as a desktop computer, a laptop computer, a Personal Digital Assistant (PDA), a mobile communication device or organizer device having access to the network 108. In a further embodiment, the user interface device 110 may access the Internet to access a web application or web service hosted by the server 102 and provide a user interface for enabling a user to enter or receive information.

The network 108 may facilitate communications of data between the server 102 and the user interface device 110. The network 108 may include any type of communications network including, but not limited to, a direct PC to PC connection, a local area network (LAN), a wide area network (WAN), a modem to modem connection, the Internet, a combination of the above, or any other communications network now known or later developed within the networking arts which permits two or more computers to communicate, one with another.

In one embodiment, the server 102 is configured to generate a radiation therapy treatment plan for an individual, retrieve a tumor position for review, and display a graphical representation of the tumor position. The server may also retrieve information from an expert system. Additionally, the server may access data stored in the data storage device 104 via a Storage Area Network (SAN) connection, a LAN, a data bus, or the like.

The data storage device 104 may include a hard disk, including hard disks arranged in an Redundant Array of Independent Disks (RAID) array, a tape storage drive comprising a magnetic tape data storage device, an optical storage device, or the like. In one embodiment, the data storage device 104 may store patient information, such as tumor location, contour maps, dosages, and may also store historical data such as data on patients who have already received treatment including their tumor position, treatment history, dosages, beam angles used to treat the patient, beam intensities used to treat the patients, and the outcome of the treatment. The data may be arranged in a database and accessible through Structured Query Language (SQL) queries, or other data base query languages or operations.

Figure 2:
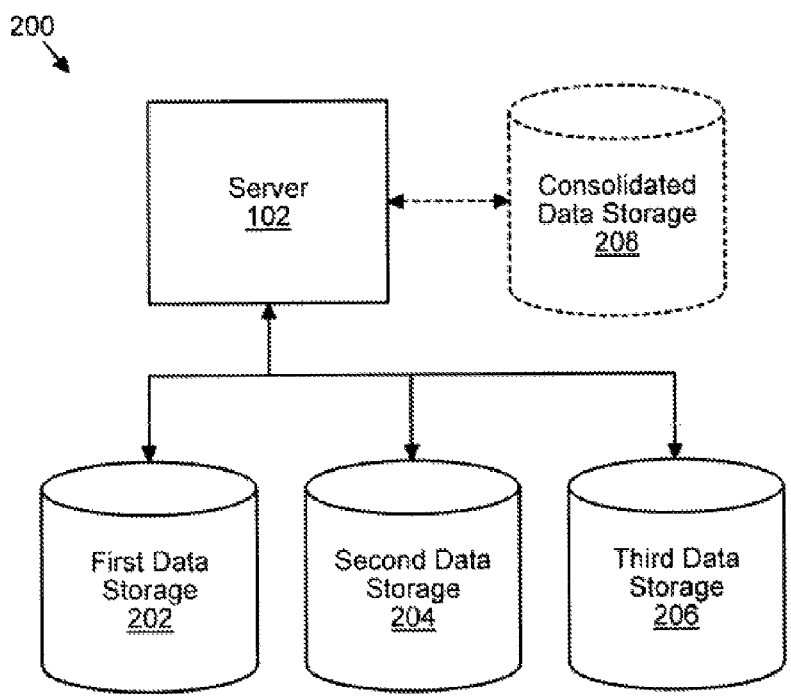
FIG. 2 is a schematic block diagram illustrating one embodiment of a database system for storing information used to generate radiation oncology treatment plans.

FIG. 2 illustrates one embodiment of a data management system 200 configured to store and manage data for the generation of radiation treatment plans. In one embodiment, the system 200 may include a server 102. The server 102 may be coupled to a data-bus 202. In one embodiment, the system 200 may also include a first data storage device 204, a second data storage device 206 and/or a third data storage device 208. In further embodiments, the system 200 may include additional data storage devices (not shown). In such an embodiment, each data storage device 204-208 may host a separate database of current patients and past patients. The patient information in each database may be keyed to a common field or identifier, such as an individual's name, social security number, hospital identification, date of birth, or the like. Alternatively, the storage devices 204-208 may be arranged in a RAID configuration for storing redundant copies of the database or databases through either synchronous or asynchronous redundancy updates.

In one embodiment, the server 102 may submit a query to selected data storage devices 204-206 to collect a consolidated set of data elements associated with an individual or group of individuals. The server 102 may store the consolidated data set in a consolidated data storage device 210. In such an embodiment, the server 102 may refer back to the consolidated data storage device 210 to obtain a set of data elements associated with a specified individual. Alternatively, the server 102 may query each of the data storage device's 204-208 independently or in a distributed query to obtain the set of data elements associated with a specified individual. In another alternative embodiment, multiple databases may be stored on a single consolidated data storage device 210.

In various embodiments, the server 102 may communicate with the data storage devices 204-210 over the data-bus 202. The data-bus 202 may comprise a SAN, a LAN, or the like. The communication infrastructure may include Ethernet, Fibre-Chanel Arbitrated Loop (FC-AL), Small Computer System Interface (SCSI), and/or other similar data communication schemes associated with data storage and communication. For example, there server 102 may communicate indirectly with the data storage devices 204-210; the server first communicating with a storage server or storage controller 106.

The server 102 may host a software application configured for generating radiation treatment plans. The software application may further include modules for interfacing with the data storage devices 204-210, interfacing a network 108, interfacing with a user, and the like. In a further embodiment, the server 102 may host an engine, application plug-in, or application programming interface (API). In another embodiment, the server 102 may host a web service or web accessible software application.

Figure 3:
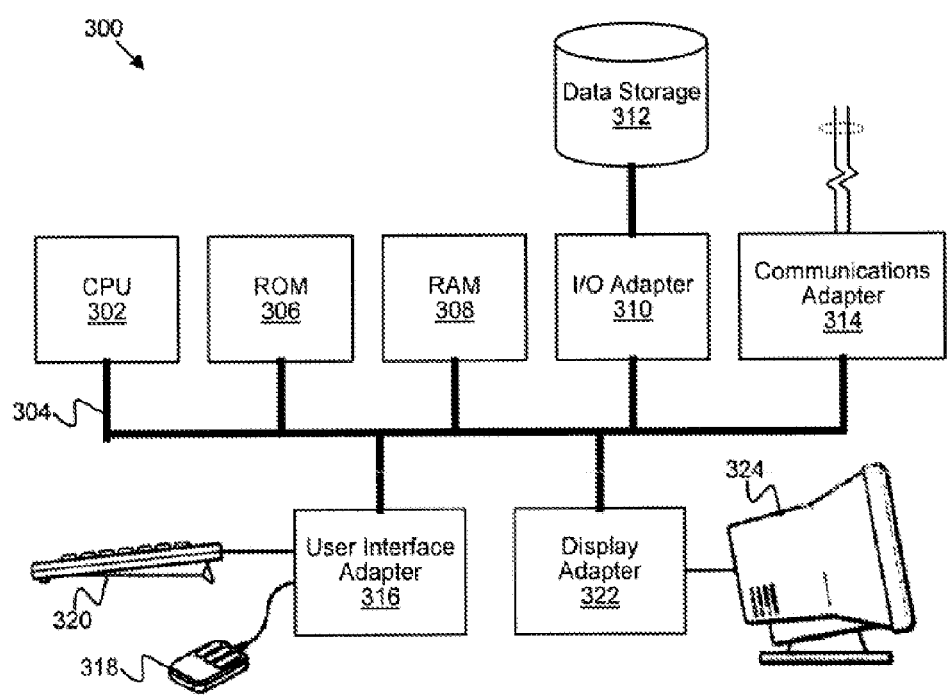
FIG. 3 is a schematic block diagram illustrating one embodiment of a computer system that may be used in accordance with certain embodiments of the system for generating radiation oncology treatment plans.

FIG. 3 illustrates a computer system 300 adapted according to certain embodiments of the server 102 and/or the user interface device 110. The central processing unit (CPU) 302 is coupled to the system bus 304. The CPU 302 may be a general purpose CPU or microprocessor. The present embodiments are not restricted by the architecture of the CPU 302, so long as the CPU 302 supports the modules and operations as described herein. The CPU 302 may execute the various logical instructions according to the present embodiments. For example, the CPU 302 may execute machine-level instructions according to the exemplary operations described below with reference to FIGS. 4 and 5.

The computer system 300 also may include Random Access Memory (RAM) 308, which may be SRAM, DRAM, SDRAM, or the like. The computer system 300 may utilize RAM 308 to store the various data structures used by a software application configured to generate radiation treatment plans. The computer system 300 may also include Read Only Memory (ROM) 306 which may be PROM, EPROM, EEPROM, optical storage, or the like. The ROM may store configuration information for booting the computer system 300. The RAM 308 and the ROM 306 hold user and system 100 data.

The computer system 300 may also include an input/output (I/O) adapter 310, a communications adapter 314, a user interface adapter 316, and a display adapter 322. The I/O adapter 310 and/or user the interface adapter 316 may, in certain embodiments, enable a user to interact with the computer system 300 in order to input information for patient identification, objective function parameters, dosages, and the like. In a further embodiment, the display adapter 322 may display a graphical user interface associated with a software or web-based application.

The I/O adapter 310 may connect to one or more storage devices 312, such as one or more of a hard drive, a Compact Disk (CD) drive, a floppy disk drive, a tape drive, to the computer system 300. The communications adapter 314 may be adapted to couple the computer system 300 to the network 106, which may be one or more of a LAN and/or WAN, and/or the Internet. The user interface adapter 316 couples user input devices, such as a keyboard 320 and a pointing device 318, to the computer system 300. The display adapter 322 may be driven by the CPU 302 to control the display on the display device 324. Additionally, the I/O adapter 310 may be connected to radiation treatment machinery that administers the treatment plan.

The present embodiments are not limited to the architecture of system 300. Rather the computer system 300 is provided as an example of one type of a machine to perform the functions of a server 102 and/or the user interface device 110. For example, any suitable processor-based device may be utilized including without limitation, for example, personal data assistants (PDAs), computer game consoles, and multi-processor servers. Moreover, the present embodiments may be implemented on application specific integrated circuits (ASIC) or very large scale integrated (VLSI) circuits.

The schematic flow chart diagrams that are provided are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

II. External Beam Radiation Therapy (Radiotherapy) and Treatment Planning

External beam radiation therapy is a well-known treatment option available to the radiation oncology and neurosurgery communities for treating and controlling certain lesions, such as arteriovenous malformations, metastatic lesions, acoustic neuromas, pituitary tumors, malignant gliomas, intracranial tumors, and tumors in various parts of the body (e.g., lung, breast, prostate, pancreas, etc.). As the name implies, the procedure involves the use of external beams of radiation directed into the patient at the lesion using either a gamma unit (referred to as a Gamma Knife), a linear accelerator, or similar beam delivery apparatus. Although treating the lesions with the radiation provides the potential for curing the related disorder, the proximity of critical normal structures and surrounding normal tissue to the lesions makes external beam radiation therapy an inherently high risk procedure that can cause severe complications. Hence, the primary objective of external beam radiation therapy is the precise delivery of the desired radiation dose to the target area defining the lesion, while minimizing the radiation dose to surrounding normal tissue and critical structures.

Thus, the basic strategy of external beam radiation therapy is to utilize multiple beams of radiation from multiple directions to "cross-fire" at the target volume. In that way, radiation exposure to normal tissue is kept at relatively low levels, while the dose to the tumor cells is escalated. Thus, the main objective of the treatment planning process involves designing a beam profile, for example, a collection of beams, that delivers a necrotic dose of radiation to the tumor volume, while the aggregate dose to nearby critical structures and surrounding normal tissue is kept below established tolerance levels.

One existing method for treatment planning in external beam radiation therapy is standard manual planning. This method is referred to as forward planning because the physician solves the direct problem of determining the appropriate dose distribution given a known set of beam characteristics and beam delivery parameters. In other words, standard manual planning involves a trial-and-error approach performed by an experienced physician. The physician attempts to create a plan that is neither complex nor difficult to implement in the treatment delivery process, while approximating the desired dose distribution to the greatest extent possible. For instance, the physician may choose how many isocenters to use, as well as the location in three dimensions, the collimator size, and the weighting to be used for each isocenter. A treatment planning computer may calculate the dose distribution resulting from this preliminary plan. Prospective plans are evaluated by viewing isodose contours superimposed on anatomical images and/or with the use of quantitative tools such as cumulative dose-volume histograms (DVH's).

Standard manual planning has many disadvantages. This iterative technique of plan creation and evaluation is very cumbersome, time-consuming, and far from optimal. Thus, manual planning results in much higher costs for patients and insurers. The physician or other experienced planner can evaluate only a handful of plans before settling on one. Therefore, standard planning has very limited success in improving local tumor control or reducing complications to normal tissue and critical structures, and as a result, greatly limits the quality-of-life for patients.

Another method for treatment planning in external beam radiation therapy employs computer systems to optimize the dose distributions specified by physicians based on a set of preselected variables. This approach is known as inverse planning in the medical community because the computer system is used to calculate beam delivery parameters that best approximate the predetermined dose, given a set of required doses, anatomical data on the patient's body and the target volume, and a set of preselected or fixed beam orientation parameters and beam characteristics. In order to solve the complex problem of arriving at an optimal treatment plan for the domain of possible variables, all existing methods of inverse treatment planning fix at least a subset of the set of variables. For example, a particular modality of external beam radiation therapy may include the following domain of possible variables: (1) number of beams, (2) configuration of beams, (3) beam intensity, (4) initial gantry angle, (5) end gantry angle, (6) initial couch angle, (7) end couch angles, (8) prescription dose, (9) target volume, and (10) set of target points.

A. Intensity-Modulated Radiation Therapy (IMRT)

IMRT is a method of treating cancer using radiation therapy that attempts to deliver a high dose to the tumor region while minimizing radiation to healthy tissues. Instead of using one beam of radiation, IMRT breaks the treatment up into multiple beams at different angles that intersect at the tumor site. In this way, low doses of radiation go to healthy tissues, while the tumor site gets overlapping radiation from multiple angles.

IMRT has been one of the hallmarks efforts to make radiotherapy treatment better, faster and more cost effective. In 2009, Liao et al., (Liao, Cox et al. 2007) demonstrated that radiation treatment with 4D CT and IMRT was as beneficial as 3D CRT in terms of the rates of freedom from locoregional progress and distal metastasis. They also saw a significant reduction in toxicity and a significant improvement in overall survival from non-small-cell lung cancer.

IMRT has made it possible to increase radiation dosage while reducing radiation-induced toxicity, yet IMRT treatment planning is still a complex process that is strongly dependent on the practitioner's experience. For instance, in IMRT treatment planning, the planner specifies beam directions based upon past experience and trial-and-error. The planner then specifies objectives for dose distribution using single-dose values, a few dose-volume points, or fully flexible DVHs. Objectives may be weighted based upon importance. The planning system represents these objectives in a cost function, which must be maximized or minimized using an optimization algorithm. The cost function numerically attempts to represent the tradeoffs that are incorporated into clinical judgment. If the planner wishes to change the outcome, he or she alters the objectives and re-optimizes. It is difficult to translate clinical requirements into a cost function and "steer" the optimization toward the best result. As a result, IMRT planning can be a time-consuming and frustrating task, and the quality of treatment plans, with similar target prescriptions and normal tissue constraints, will vary between different treatment planners and different institutions.

In IMRT, the beam intensity is varied across the treatment field. Rather than being treated with a single large, uniform beam, the patient is treated with many very small beams, each of which may be configured with a different intensity. Intensity modulation allows more intense treatment of the tumor, while limiting the radiation dose to adjacent healthy tissue. Appropriate data variables such as user input, constraints (e.g., dosimetric, beam geometry, etc.), clinical objectives, etc. are used to determine the corresponding treatment plan optimization model(s) and optimization mathematics, as well as determine the globally optimal solutions for the IMRT treatment plan. An embodiment of the invention is the use of AutoPlan to create IMRT treatment plans.

B. Proton Therapy (Particle Therapy)

Proton therapy has emerged as a particularly efficacious treatment for a variety of conditions. In proton therapy, positively charged proton subatomic particles are accelerated, collimated into a tightly focused beam, and directed towards a designated target region within the patient. Protons exhibit less lateral dispersion upon impact with patient tissue than electromagnetic radiation or low mass electron charged particles and can thus be more precisely aimed and delivered along a beam axis. Also, upon impact with patient tissue, protons exhibit a characteristic Bragg peak wherein a significant portion of the kinetic energy of the accelerated mass is deposited within a relatively narrow penetration depth within the patient. This offers the significant advantage of reducing delivery of energy from the accelerated proton particles to healthy tissue interposed between the target region and the delivery nozzle of a proton therapy machine as well as to "downrange" tissue lying beyond the designated target region. Depending on the indications for a particular patient and their condition, delivery of the therapeutic proton beam may preferably take place from a plurality of directions in multiple treatment fractions to maintain a total dose delivered to the target region while reducing collateral exposure of interposed desired/healthy tissue. An embodiment of the invention is the use of AutoPlan to create proton therapy treatment plans.

C. Volumetric Modulated Arc Therapy or VMAT

VMAT is similar to 3D-CRT and IMRT in that it follows the same idea of delivering beams of various intensity to the tumor through apertures which are conformed to the silhouette of the tumor from the beam's-eye-view, or of approximating the IMRT intensity maps. However VMAT differs from these methods in that it strives to deliver its dose in continuous arcs around the patient's body, rather than in discrete angles. That is, whereas most methods of delivery simply position the device (called the gantry) around the body, select a position, choose an aperture, and activate their radiation dose, VMAT delivers a continual dose as the gantry rotates. It is estimated that more than half of modulated photon radiotherapy will be delivered by VMAT technologies. An embodiment of the invention is the use of AutoPlan to create VMAT plans.

D. Stereotactic Body Radiation Therapy or SBRT

SBRT is a treatment procedure similar to central nervous system (CNS) stereotactic radiosurgery, except that it deals with tumors outside of the CNS. A stereotactic radiation treatment for the body means that a specially designed coordinate-system is used for the exact localization of the tumors in the body in order to treat it with limited but highly precise treatment fields. SBRT involves the delivery of a single high dose radiation treatment or a few fractionated radiation treatments (usually up to 5 treatments). A high potent biological dose of radiation is delivered to the tumor, improving the cure rates for the tumor, in a manner previously not achievable by standard conventional radiation therapy. SBRT treatment could be delivered using intensity modulated photon beam, particle beam or arc beams. Similarly, because this specialized form of radiation involves the use of multiple radiation beam angles, expert Radiation Oncologists specialized in this technique are able to safely deliver high doses of radiation, with very sharp dose gradient outside the tumor and into the surrounding normal tissue. Creating intensity modulated and volumetric arc modulated SBRT plans is almost identical to creating IMRT and VMAT plans. In an embodiment of the invention, AutoPlan is used to create SBRT plans.

E. Adaptive Radiation Therapy (ART)

ART is considered mainly to be technology in which repeated measurements of the patient's geometry during the treatment period is carried out and used to improve treatment so that a more patient-specific treatment can be performed. Today, radiation treatment is based on the patient's anatomy at the time the CT scans were taken. In fact, the patient's outer contours and inner organs change both position and form on a daily basis during treatment. These geometrical variations can be handled by adaptive radiation therapy. The complicated planning process—requiring a great deal of trial-and-error—is often the most time-consuming part of RT treatment. Several cycles are typically needed for review of patient progress, consultation between the radiation oncologist and dosimetrist, and subsequent reassessment of the treatment plan, making the IMRT plan expensive. ART may require even more repetition of treatment plan review, making them prohibitively expensive. An embodiment of the invention is the use of autoplan algorithm to reduce the cost of ART. Therefore it is possible to adopt ART in routine clinical practice. An embodiment of the invention is using AutoPlan to create ART treatment plans.

III. Treatment Planning

Figure 4:
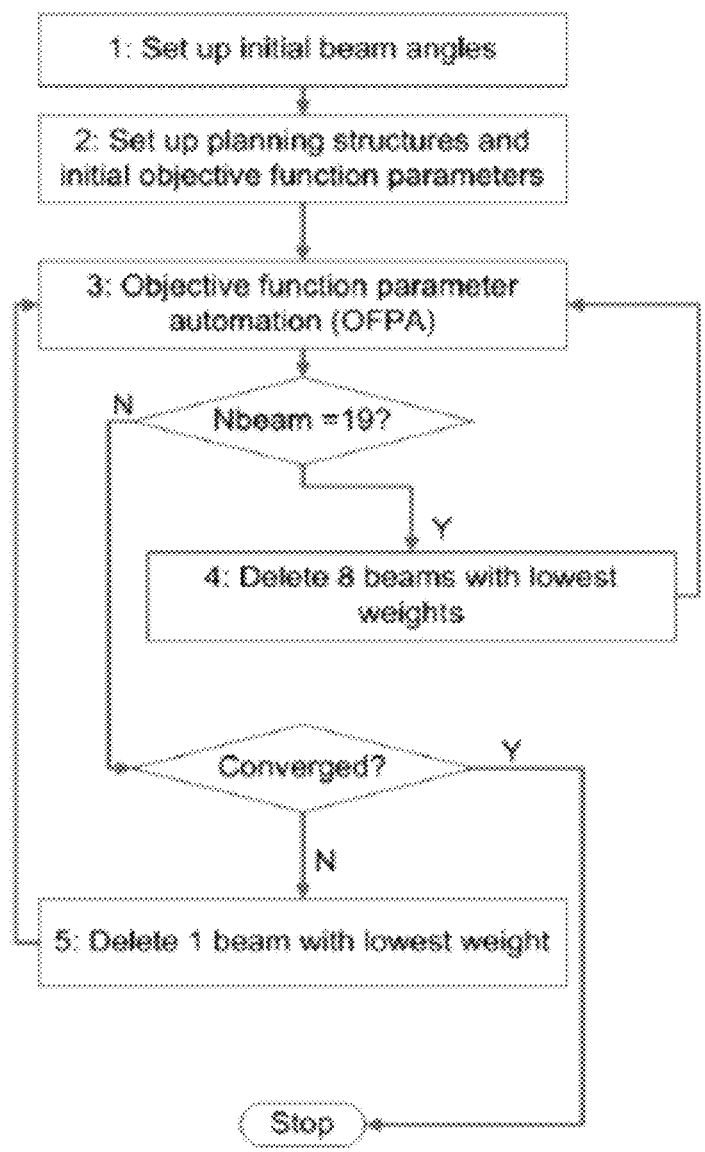
FIG. 4 is a flowchart for one embodiment of the AutoPlan system.

FIG. 4 illustrates the flow, architecture, operation and/or functionality of one embodiment of the present invention for developing a radiation treatment plan for external beam radiation therapy. At block 1 the initial beam angles are set up. The beam angles may be set up by an expert system. At block 2 the planning structures and initial objective function parameters are configured. The objective function parameters may be input from outside of the system, or may be default values found within the system. At block 3 the objective function parameters are adjusted. At block 4 a plurality of beams with the lowest weights are deleted from the treatment plan and unconstrained objective function parameters are re-adjusted based on the remaining beams in the treatment plan. At block 5, additional beams in the treatment plan are deleted and the unconstrained objective function parameters are re-adjusted based on the remaining beams. Once the objective function parameters have converged, the treatment plan may be output to the user or to treatment machinery.

FIG. 5A illustrates the flow, architecture, operation, and/or functionality of one embodiment of the present invention for developing a radiation treatment plan for external beam radiation therapy. Given the overlapping volume of PTV, total lung the mean lung dose (MLD), for example, or equivalent mean dose (MD) for the specific organ under treatment is estimated. If the mean dose is less than a set value the PTV is used. If the mean dose is greater than or equal to the set value, the ITV is used. The objective function values are then adjusted to account for the treatment volume. The set values are generally set by the institution at which the treatment is being performed. For example, MDACC sets the MLD maximum at 22 Gy.

FIG. 5B illustrates the flow, architecture, operation, and/or functionality of one embodiment of the present invention for developing a radiation treatment plan for external beam radiation therapy. Each objective function parameter is given a sequence number, i. For example, the first objective function parameter i is 1, for the second i=2, and so on until the last objective function value, i=number of objectives (Nobj). Each objective function parameter (i) is checked to see if it is constrained or unconstrained. If the objective function parameter is constrained, no modification or adjustment to the objective function parameter is made and the next objective function parameter is reviewed (i=i+1). If the objective function parameter is unconstrained the objective function parameter value is compared to Eobj. Eobj is a parameter which is used to determine the maximum sub-objective function value. If Eobj is larger, more weight is given to the objective. In one embodiment of the invention, Eobj=0.2 for all objective function parameters. If the objective function parameter value is less than Eobj, the objective function parameter is adjusted. In an embodiment of the invention, the objection function parameter is adjusted by modifying the objective function parameter value, or by modifying a variable used to calculate the objective function parameter value, such as EUD, weight, and/or alpha. In a specific embodiment of the invention, the modification is that the EUD variable of the objective function parameter is divided by two. If the objective function parameter is modified, the objective value is re-calculated. Once the objective function value is greater than or equal to Eobj the beam intensities are optimized and all functional parameter values are re-evaluated. The loop continues until no objectives are adjusted.

FIGS. 6(a) and (b) illustrate the flow, architecture, operation, and/or functionality of one embodiment of the present invention for developing a radiation treatment plan for external beam radiation therapy. This algorithm only adopted non-constrained objectives. This algorithm is very similar to the one described in FIGS. 4, 5(a) and 5(b). Since this non-constrained algorithm is may used for generating multiple autoplans in the multi-criteria optimization method, an example of which is described in FIG. 12, a brief description of this method is presented. First, the algorithm automatically generates planning ROI structures based on physician-drawn contours; the newly generated structures involve modifications to the original contours in order to improve the planning quality and efficiency. Tumor size and location information is automatically extracted and matched with the closest case in an expert system and then initial beam angles are configured based on the best match from the expert system. Inverse planning objectives with pre-defined parameters are then loaded into a planning system, such as Pinnacle3. The index of inverse planning iterations (i) is now set to the initial value 1 and AutoPlan calls the optimization process to execute for the first round, after which AutoPlan automatically adjusts the objective parameters (illustrated in FIG. 6(b)), resets the beams, and executes the second round of optimization. Then, a plurality of beams, for example 8 beams, with the lowest weight among the initial beams are deleted; the rest of the beams are reset and optimized for the last time. The inverse planning is finished and the plan obtained at this point is saved as the final plan.

FIGS. 7A and 7B display a flowchart of an embodiment of objective function parameter optimization that may be used in generating autoplans. In an embodiment of the invention, the method is used generating plans for prostate cancer treatment. The functionality of this algorithm is very similar to the one described in FIG. 4 and FIGS. 5A and 5B and FIGS. 6A and 6B. First, the algorithm automatically generates planning ROI structures based on physician-drawn contours; the newly generated structures involve modifications to the original contours in order to improve the planning quality and efficiency. Radiation beams with pre-selected angles are then automatically configured and the inverse planning objectives with pre-defined parameters are loaded into a planning system, such as the Pinnacle3 planning system. The index of inverse planning iterations (i) is now set to the initial value 1 and the AutoPlan calls the optimization process to execute. After the optimization of the objective functions is finished, AutoPlan checks if the maximum number of iterations has been reached—if yes, stop the planning procedure and if no, check if the PTV D95 has reached its lower bound threshold (DT). If it has exceeded the threshold, stop the planning procedure; otherwise, adjust the inverse planning objective parameters, increase the number of iterations (i), and continue optimization for the next round without resetting the beams. Repeat steps 3 to 4 until either the maximum number of iterations has been reached or the PTV D95 has exceeded the threshold. The plan generated at this point is saved; intermediate plans are also saved after step 3 at iterations 3 and higher. In another embodiment of the invention, this method is used to VMAT technologies.

FIG. 7(b) illustrates the work flow of step 4 in FIG. 7(a). In the initially loaded objective list, all objectives are non-constrained type; therefore, each objective is assigned a weight between 0 and 100. In this figure, i represents the index of the current objective and NTargetObj represents the total number of objectives corresponding to the PTV or the PTV-Ring structures, which are located on top of the list. These objectives (indexed between 1 and NTargetObj) are adjusted by multiplying their weight by a pre-defined factor (F); the weight of the PTVRing objective is not to exceed 50. The objectives after such parameter adjustment serve as the starting point of the next round of optimization.

This algorithm only contains non-constrained objective function and was thoroughly tested for generating autoplan for prostate cancer. One important feature of this algorithm is that it continues optimization for the next round without resetting the beams after objective function parameters was adjusted. This algorithm is also the major algorithm used for generating autoplan for VMAT technologies for all type of cancers such as lung cancer.

A. Types of Cancer

In certain embodiments of the invention, AutoPlan is used to generate treatment plans for tumors located throughout the body. In specific embodiments of the invention, AutoPlan generates treatment plans for lung, prostate, esophageal, brain, mesothelinoma, head and neck, central nervous system, GU, gynecological tumors, and gastrointestinal tumors.

B. Objective Functional Parameters

The following are examples of objective functional parameters used in the treatment of various cancers.

1. Lung

Figure 6:
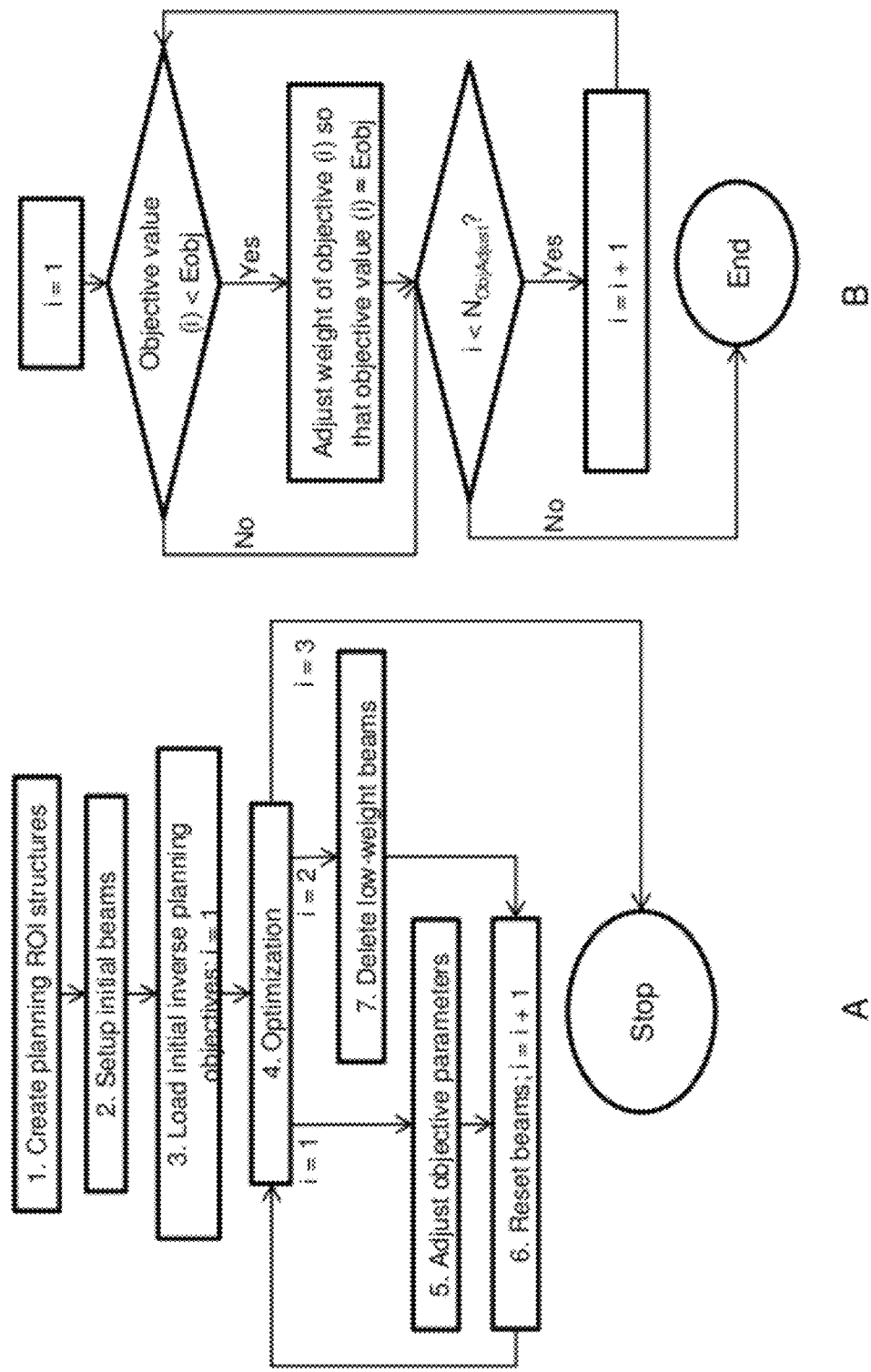
FIGS. 6A and 6B display alternative flowcharts of an embodiment of beam angle automation and objective function parameter automation algorithm.
Figure 7:
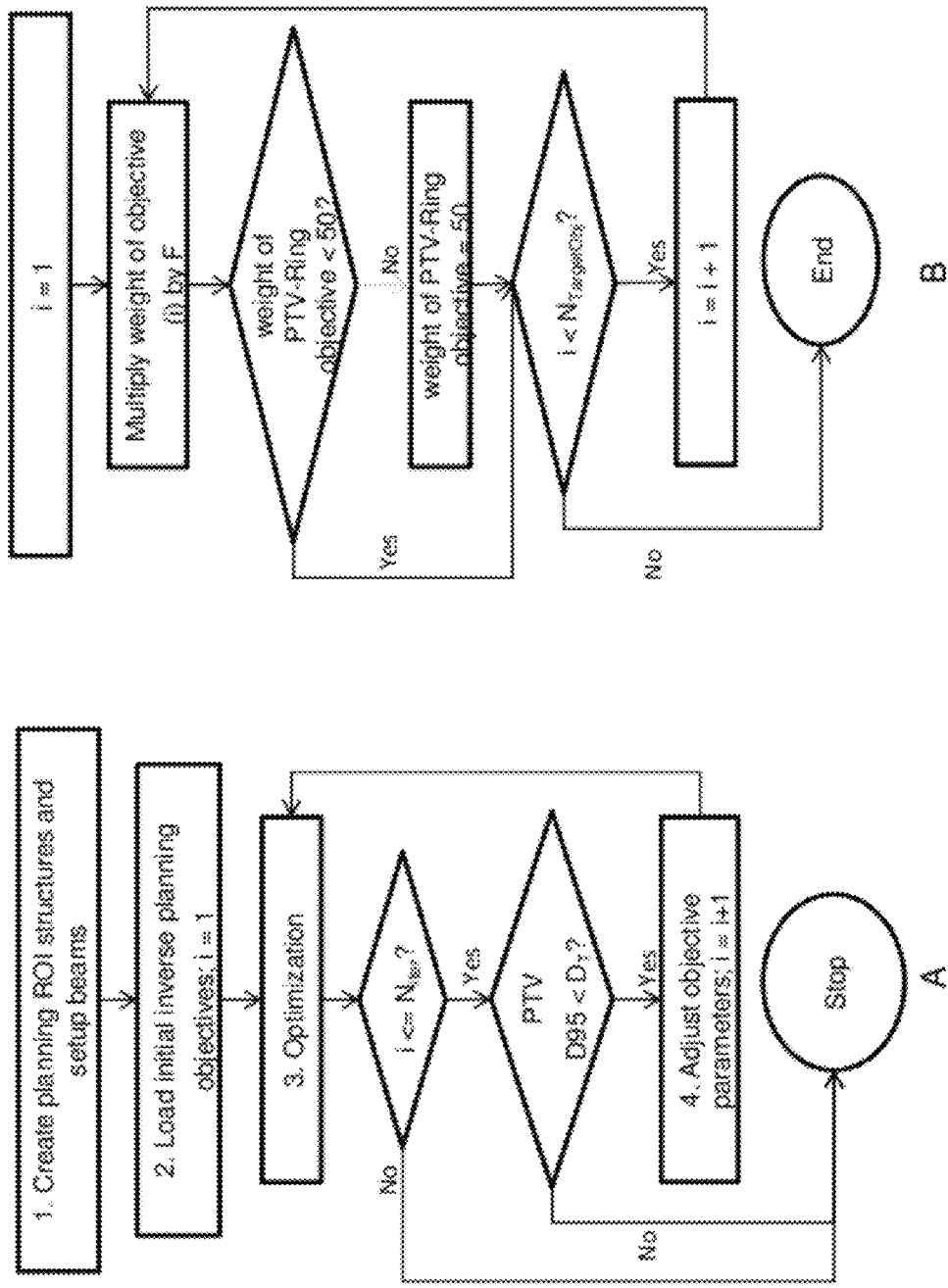
FIGS. 7A and 7B display a flowchart of an embodiment of objective function parameter optimization. In a specific embodiment of the invention, the flowchart is used to create an autoplan for the treatment of prostate cancer.

FIG. 8 and FIG. 9 displayed the planning structures (ROIs), objective function parameters used in the AutoPlan method described in FIGS. 5 and 6 for lung cancers respectively. In both FIGS. 8 and 9, the objective function values in a random run of the method is also displayed. Those planning structures and initial objective function parameters are used for all the lung patients. The planning structures are created as follows:

FS-PlanPTV: a copy of the physician-drawn PTV structure

FS-NTAvoid: entire normal tissue extracting 1 cm-expansion of the PTV

FS-LungAvoid: the physician-drawn lung structure extracting 1 cm-expansion of the PTV FS-CLungAvoid: the contra-lateral part of the FS-LungAvoid structure FS-ILungAvoid: the ipsi-lateral part of the FS-LungAvoid structure FS-HeartAvoid: the physician-drawn heart structure extracting 1 cm-expansion of the PTV FS-PrvCord: 0.5 cm-expansion of the physician-drawn cord structure FS-PrvCordRing: 3 cm wide partial ring structure surrounding the FS-PryCord toward the posterior and the contra-lateral directions FS-PlanEsoph: a copy of the physician-drawn esophagus structure 2. Prostate FIG. 10 lists the planning structures (ROIs), objective function parameters used in the AutoPlan method described in FIG. 7 for prostate cancers. The planning structures are created as follows:

plan-PTV: a copy of the physician-drawn PTV structure plan-PTVRing: 0.8 cm wide ring structure surrounding 0.2 cm expansion of the PTV FS-Ring: 3 cm ring structure within the external body FS-NormalTissue: entire normal tissue extracting 1 cm-expansion of the PTV FS-BladderAvoid: the physician-drawn bladder structure extracting 0.3 cm-expansion of the PTV FS-RectumAvoid: the physician-drawn rectum structure extracting 0.3 cm-expansion of the PTV FS-FHAvoid: the physician-drawn femoral heads structure extracting 0.3 cm-expansion of the PTV 3. Head and Neck FIG. 11 lists the planning structures (ROIs), and objective function parameters used in the autoplan algorithms for head neck cancers. The planning structures are created as follows:

FS-PTV62: a copy of the physician-drawn PTV structure prescribed to 62 Gy

FS-PTV60: the physician-drawn PTV structure prescribed to 60 Gy extracting 0.2 cm-expansion of the higher prescription PTVs FS-PTV59: the physician-drawn PTV structure prescribed to 59 Gy extracting 0.2 cm-expansion of the higher prescription PTVs FS-PTV56: the physician-drawn PTV structure prescribed to 56 Gy extracting 0.2 cm-expansion of the higher prescription PTVs FS-NormalTissue: entire normal tissue extracting 1 cm-expansion of the PTV FS-InsideRing: 1 cm wide ring structure surrounding 1 cm expansion of the PTV FS-OutRing: FS-NormTissue extracting FS-InsideRing FS-cord expanded: the physician-drawn cord expanded structure extracting 0.5 cm-expansion of the PTV FS-brainstem expanded: the physician-drawn brainstem expanded structure extracting 0.5 cm-expansion of the PTV FS-LT Parotid: the physician-drawn left parotid structure extracting 0.5 cm-expansion of the PTV FS-RT Parotid: the physician-drawn right parotid structure extracting 0.5 cm-expansion of the PTV FS-larynx: the physician-drawn larynx structure extracting 0.5 cm-expansion of the PTV C. Beam Angle Selection In IMRT treatment planning the angles at which radiation is delivered to the treatment site in the patient's body, commonly called gantry angles and couch angles in the case of non-coplanar beams, are usually pre-selected based on experience and intuition of the operator. The corresponding beam intensity profiles are then optimized under the guidance of an objective function using inverse treatment planning methods. General information on these methods is provided by S. Webb, "Optimizing the Planning of Intensity-Modulated Radiotherapy", Physics in Medicine and Biology, Vol. 39, 1994, pp. 2229-2246; S. V. Spirou and C. S. Chui, "A Gradient Inverse Planning Algorithm with Dose-Volume Constraints", Medical Physics, Vol. 25, 1998, pp. 321-333; R. Mohan, et al., "The Potential and Limitations of the Inverse Radiotherapy Techniques", Radiotherapy & Oncology, Vol. 32, 1994, pp. 232-248; L. Xing, et al., "Fast Iterative Algorithms for 3D Inverse Treatment Planning", Medical Physics, Vol. 25, 1998, pp. 1845-1849; and L. Xing and G. T. Y. Chen, "Iterative Methods for Inverse Treatment Planning", Physics in Medicine and Biology, Vol. 41, 1996, pp. 2107-2123.

D. Expert System

An expert system may be used to select beam angles. From a technologically point of view, automating the treatment planning process is a difficult problem. One problem which must be overcome in developing automated treatment planning is the selection of optimal beam angles, which are currently chosen by experienced planners. Since the beginning of IMRT, beam angle optimization algorithms (BAOs) have been a subject of intense research (Stein, Mohan et al. 1997; Pugachev and Xing 2002; Meedt, Alber et al. 2003; Wang, Zhang et al. 2004; Wang, Zhang et al. 2005; Liu, Jauregui et al. 2006; D'Souza, Zhang et al. 2008; Potrebko, McCurdy et al. 2008) in the radiotherapy community. However, BAO algorithms have not been adopted in routine clinical practice. One reason is that the optimal beam angle is strongly dependent on the cost function used to obtain that angle. However, the optimal cost function for a particular patient is not known. The weights and objectives—also dependent on the beam angles initially selected—used in the cost function to achieve the best possible treatment plan must be optimized. Choosing initial angles from an expert system is a new approach. First, the initial angles already take advantage of clinical dosimetrists' previous experiences to eliminate some angles which are usually never chosen to design the plan for a tumor in some geometrical location. Second, choosing non-coplanar angle is also a very difficult problem since the search space of non-coplanar angles is very large. Several non-coplanar angles may be picked which are frequently used by dosimetrists if the tumor was located in some particular position. Using non-coplanar angles indeed can improve the plan quality. The added advantage of this approach is that those non-coplanar beams automatically avoid the gantry collision problem since all initial non-coplanar beams have been used before to treat the patients. Most importantly, although an expert database was used to aid in selecting the beam angles, the database need not be relied on to chose the optimal angles.

In one embodiment of the invention, the database chooses initial angles which will be optimized further to select the optimal angles. This approach normally yield plans which are better than the plan manually designed by clinical dosimetrists. Even the beam angles selected are more optimal than some manually selected by experienced dosimetrists.

The Expert System or Database may include the tumor position, beam angles (gantry, couch, collimator angles), tumor sizes, and treatment results for each plan. In one embodiment of the invention, the expert database serves as the base for the beam angle selections. In another embodiment, the beam angles in the expert system are unchanged after selection from the expert system. In a further embodiment, the beam angles are unchanged, but the number of beams is reduced. In another embodiment of the invention, the expert system does not include actual patient data, but is a conglomeration of patient data done by an expert. The prostate beam angles used in the Examples are as follows: 8, 225, 260, 295, 330, 30, 65, 100, 135.

E. Beam Intensity Optimization and/or Adjustment

Any available software may be used to optimize the beam intensities in AutoPlan. For example, HELIOS (Varian Associates, Palo Alto, Calif.) and Pinnacle (Philips, Milpitas, Calif.) are both available software packages used to optimize beam intensities. While an example of IMRT beam intensity optimization is described below, proton therapy planning also involved beam optimization, and such optimization may be used in combination with the current invention. Any of the following IMRT beam intensity optimizations may be used to select the beam intensities in AutoPlan.

1. Optimization of IMRT Beam Intensities

The potential of IMRT to improve outcome has spurred continued interest in improving optimization techniques. Many optimization algorithms for determining the optimized intensity profiles have been utilized. These include linear programming (Wu et al., 2000; Rosen et al, 1991) mixed-integer programming (Langer et al, 1996; Lee at al, 2000) gradient algorithms (Bortfeld et al, 1990; Bortfeld, 1999; Cho et al., 1998; Holmes et al., 1991; Hristov et al., 2002; Starkschall et al., 2001; Wu and Mohan, 2000), simulated dynamics (Wu and Mohan, 2001; Hou et al., 2003), and stochastic algorithms (Morrill et al., 2001; Rosen et al., 1995; Webb, 1991; Wu et al., 2000). Each of these methods has advantages and disadvantages. Gradient algorithms are normally fast but they may get trapped in local minima far from good solutions. Although stochastic algorithms, such as simulated annealing and genetic algorithms, have the advantages of avoiding getting trapped in local minima in principle, they are slow and may also get trapped in local minima if, for example, the thermal cooling process is too fast in the case of simulated annealing, or if the population evolution is not realistic in the case of genetic algorithms. For stochastic and gradient algorithms, the value of an objective function (called the score) is used to drive the optimization process to an extremum. The commonly used objective functions are dose based (Wu and Mohan, 2000; Bortfeld et al., 1996), dose volume-based (Wu and Mohan, 2000; Bortfeld et al., 1996; Langer et al., 1990) and biology based (Wu et al., 2000; Langer et al., 1990). Each objective function is composed of subobjectives corresponding to individual anatomic structures. The subobjectives are assigned relative weights, or penalties, reflecting the relative importance of the end point. Normally, the penalty parameters are chosen subjectively and determined by trial and error. Their values are not intuitively obvious to the treatment planner.

Linear programming approaches, including mixed integer programming approaches, on the other hand, normally use hard constraints (but can accommodate soft constraints as well) on tumors and organs at risk (OARs) to perform optimization without the need to use artificially defined objective functions. The application of the linear programming approach in radiotherapy has recently attracted the attention of the operations research community (Holder, 2000; Holder 2002). However, the linear programming techniques require large numbers of iterations and are slow. The simulated dynamics approach, recently developed by Hou et al. (Hou et al., 2003), combines the advantages of gradient algorithms and the constraint approach in the IMRT treatment planning. Its extensive application in routine radiation treatment planning is still to be evaluated.

Because gradient algorithms need fewer iterations to obtain a reasonable solution, they represent the most commonly implemented algorithms in the commercial planning systems, for example HELIOS (Varian Associates, Palo Alto, Calif.) and Pinnacle (Philips, Milpitas, Calif.). The Newton's (Bortfeld et al., 1990; Wu and Mohan, 2000) and conjugate gradient (CG) (Spirou and Chui, 1998) algorithms are the two most prevalent gradient methods. Newton's algorithm and the steepest descent (SD) algorithm use the gradient of the objective function to choose the direction of optimization. The SD method is not efficient in theory because the optimization directions between the first and next iterations are not orthogonal. The results of optimization in the next iteration may partially spoil the results of optimization achieved in the previous iteration. The CG algorithm avoids this problem by producing a sequence of orthogonal directions by combining the current gradient of the objective function with the previous directions of optimization. Theoretically, the CG algorithm is more efficient. However, the CG algorithm requires a line minimization to determine the step size after the search direction has been determined. The line minimization process is very slow and can considerably reduce the overall speed of the CG algorithm. Intelligent ways to avoid line minimization have been devised. For example, Spirou and Chui) (Spirou and Chui, 1998) have suggested an exact value for the step size for the quadratic cost function. However, this value is specific to the simple dose and dose-volume cost functions and cannot be applied to more general objective functions such as biologybased objective functions. The need for avoiding line minimization for CG algorithm is of interest in IMRT as well as in other fields. Moller (Moller, 1993), for example, proposed a variation of the CG algorithm, called the "scaled conjugate gradient" (CG) algorithm, which avoids the time consuming line search to determine the step size during optimization. This algorithm is widely applied in the field of neutral networks and can be used with any type of objective function.

The IMRT may be integrated into the Pinnacle treatment planning system (Philips, Milpitas, Calif.). Pinnacle may be used for patient contouring, beam setup, dose-volume or EUD parameter input, dose computations for intensity-modulated fields, and some of the analyses of optimized intensity-modulated dose distributions. The details of this optimization system are described elsewhere (Wu and Mohan, 2000; Wu et al., 2002). AutoPlan may use such a treatment planning system as Pinnacle to input patient contouring, parameter input, optimization of beam intensities based on dose distributions. AutoPlan will generate the beam angles based on an expert system and optimize or select new objective functional parameters to further enhance the treatment plan. A program such as Pinnacle may be used to adjust and/or optimize the beam intensities within the AutoPlan method or system. Additional description of optimization techniques for IMRT may be found in Zhang et al., Med. Phys. 31(5), May 2004, incorporated herein in its entirety.

F. Multi-Criteria Optimization (MCO) Algorithm

Figure 12A:
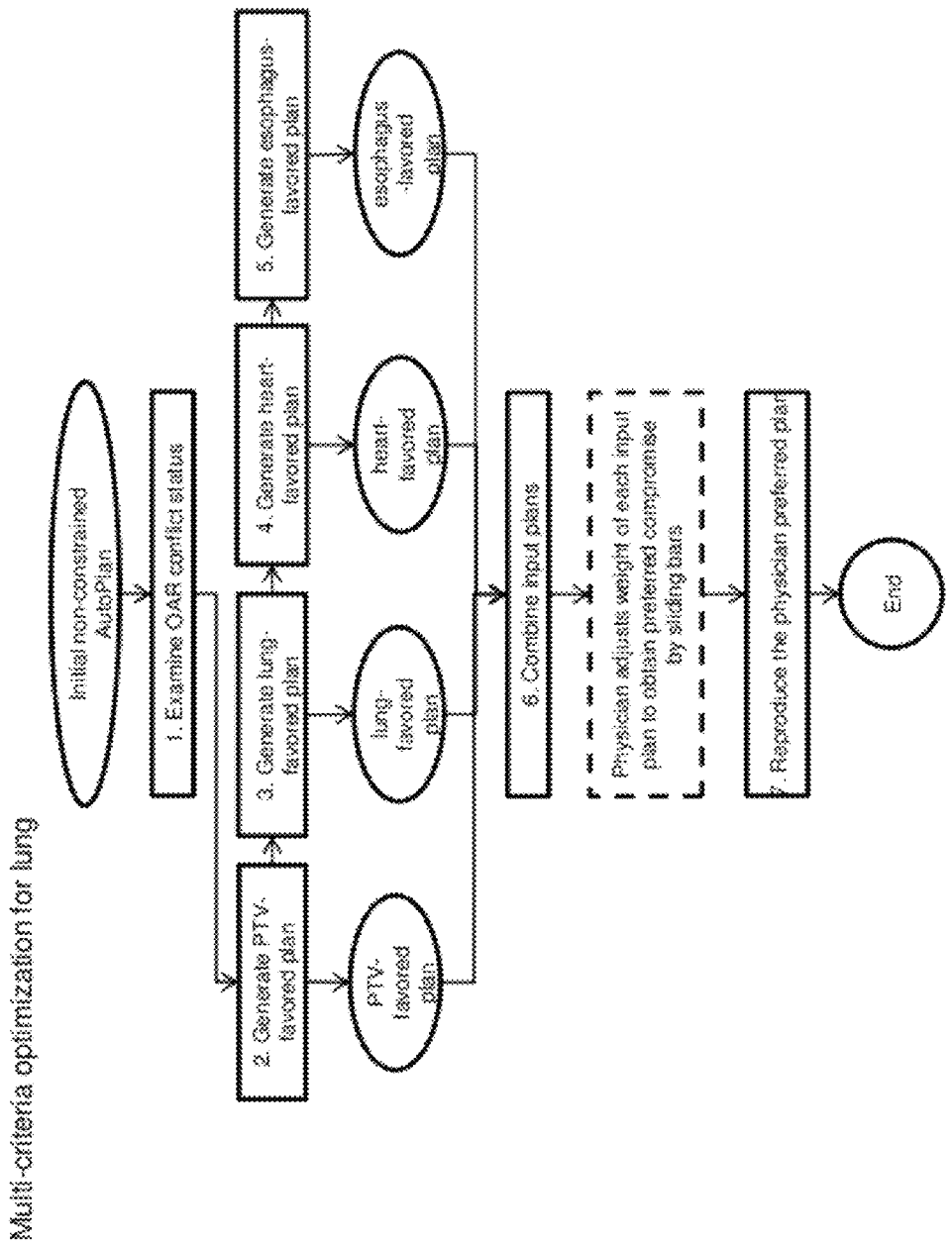
FIG. 12(a-e and g) illustrate the algorithm used for the multi-criteria optimization (MCO) in the autoplan system.
FIG. 12(f) illustrates a graphical user interface (GUI) of treatment plan explorer implementation with five autoplans (LungBase, HeartBase, EsoBase, PTVbase, CordBase) automatically generated by the autoplan algorithm. The treatment plan explorer allowed clinicians interactively adjust the DVH as well iso-dose distributions.
Figure 12:
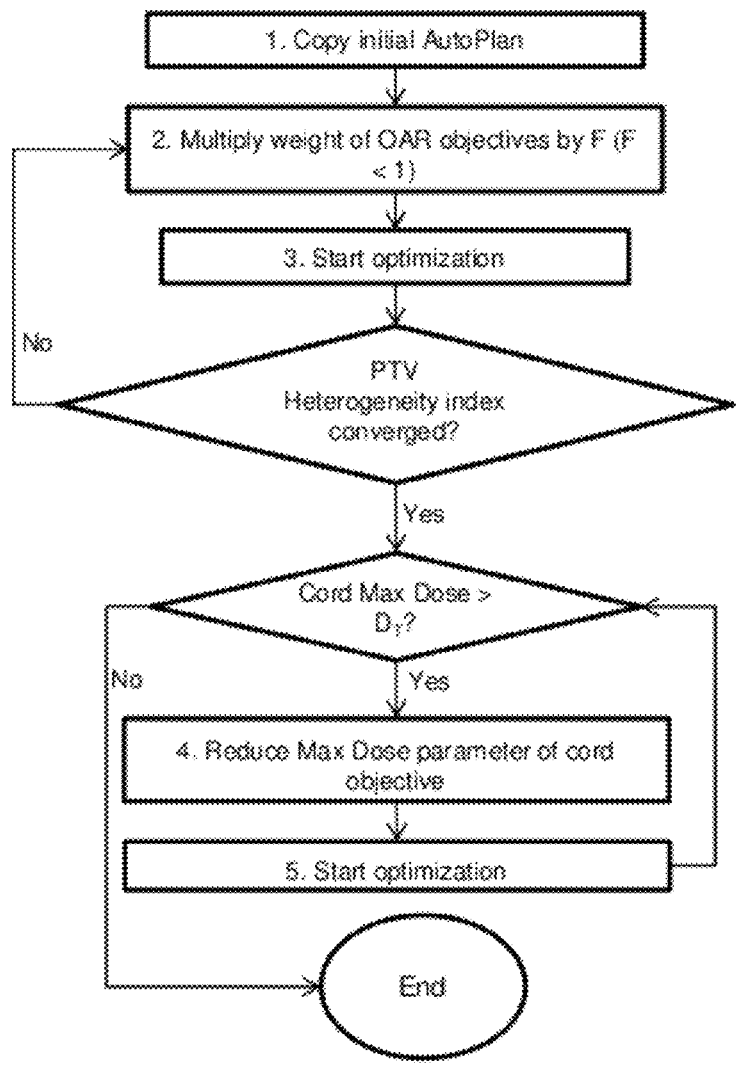
Figure 12:
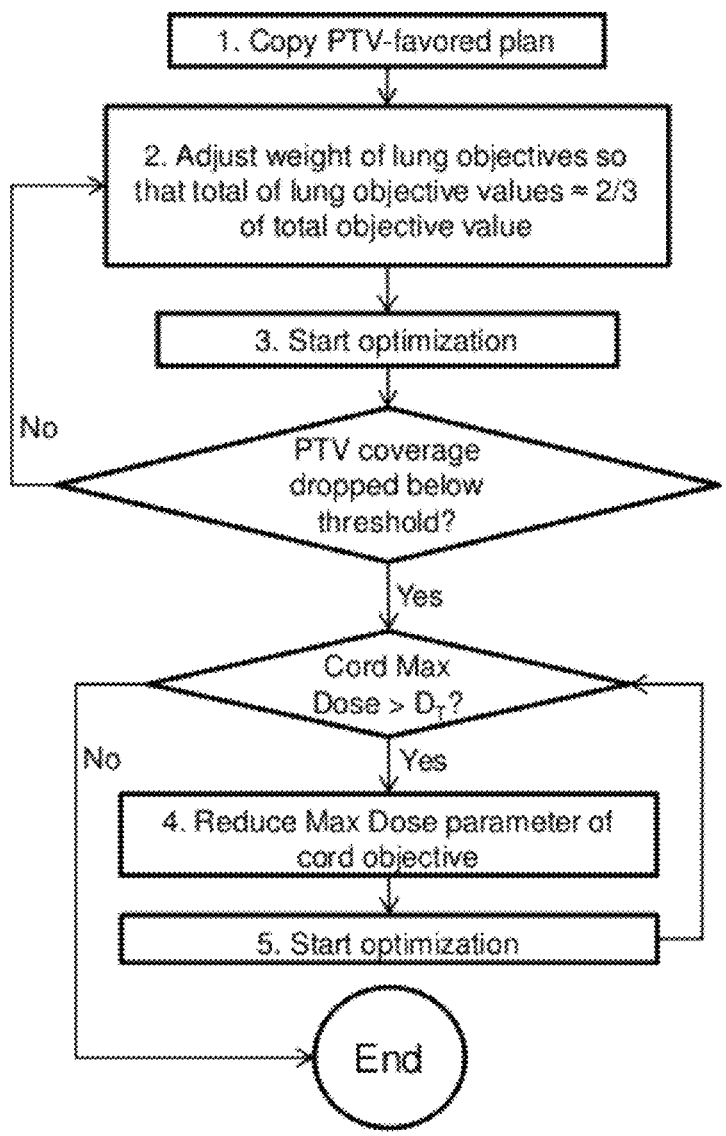
Figure 12:
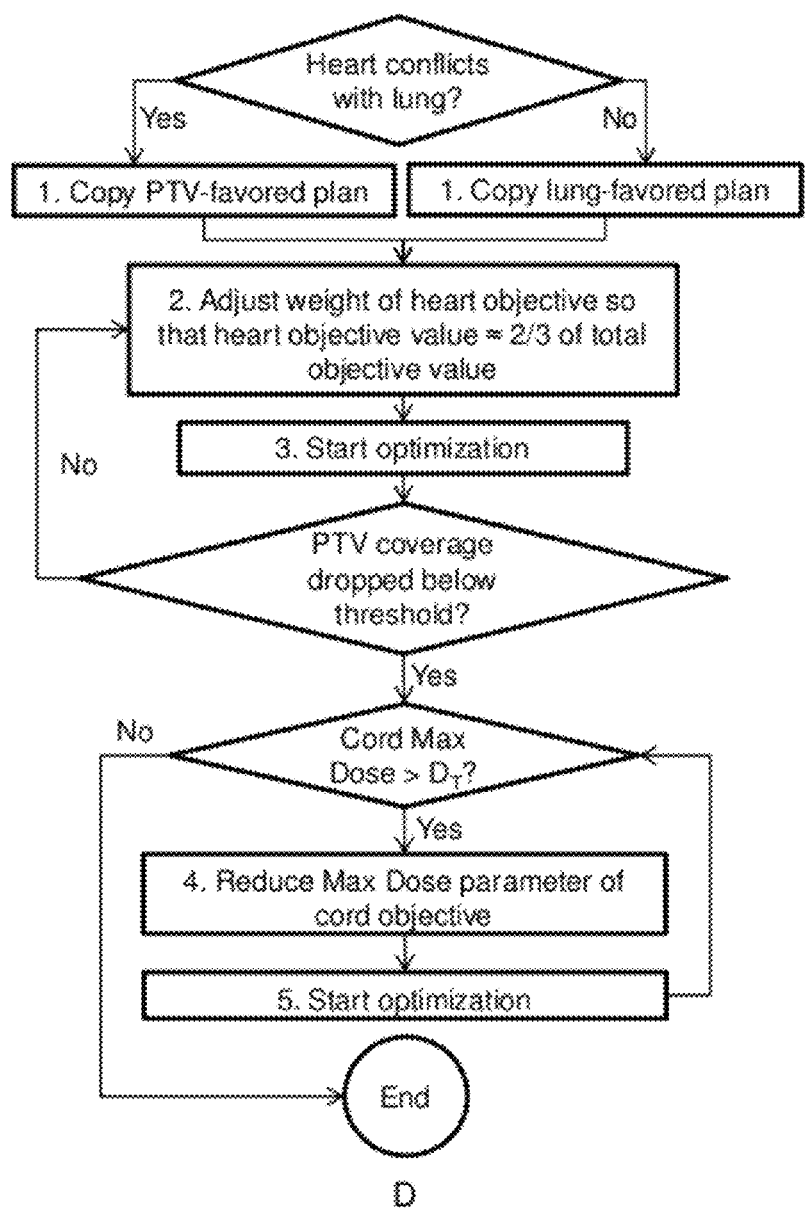
Figure 12:
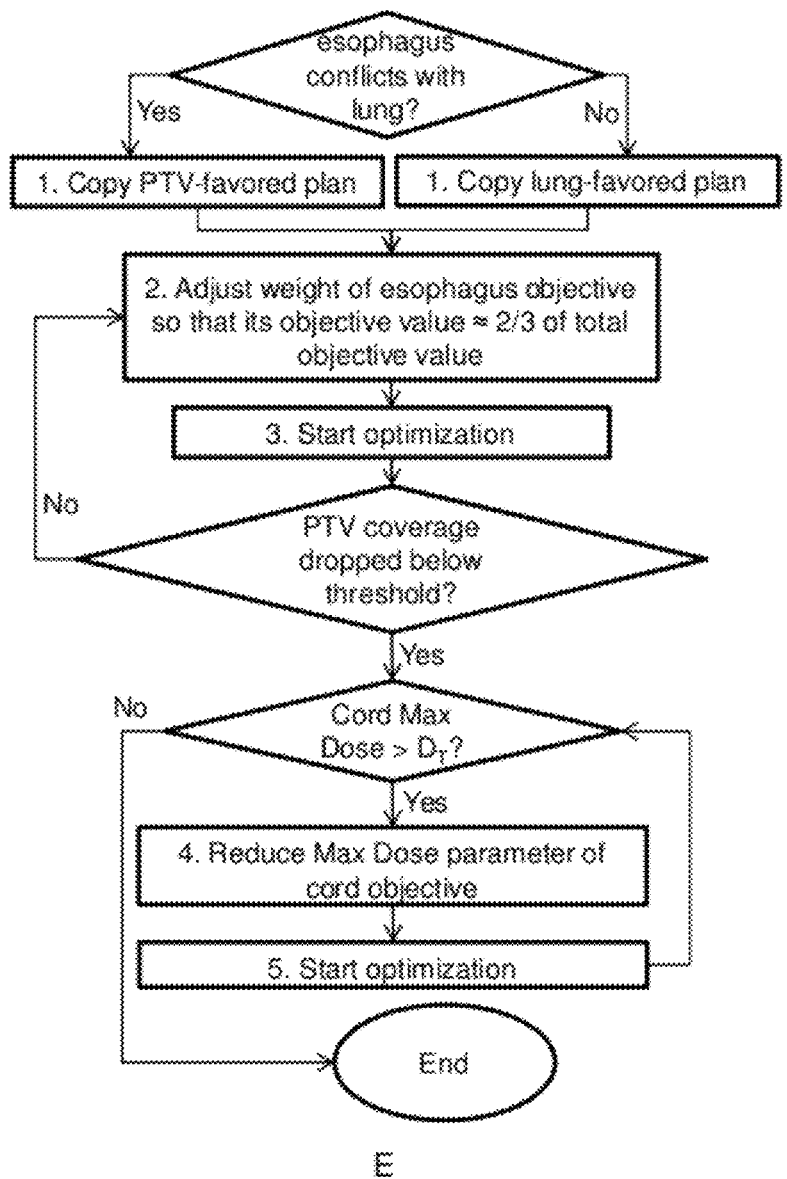
Figure 12F:
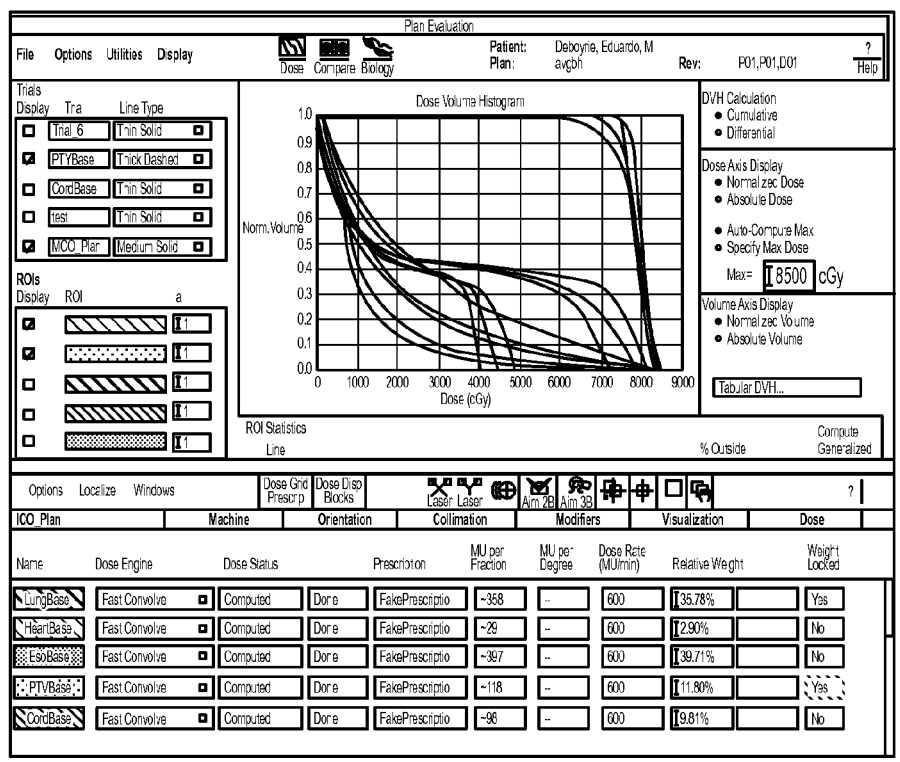
Figure 12:
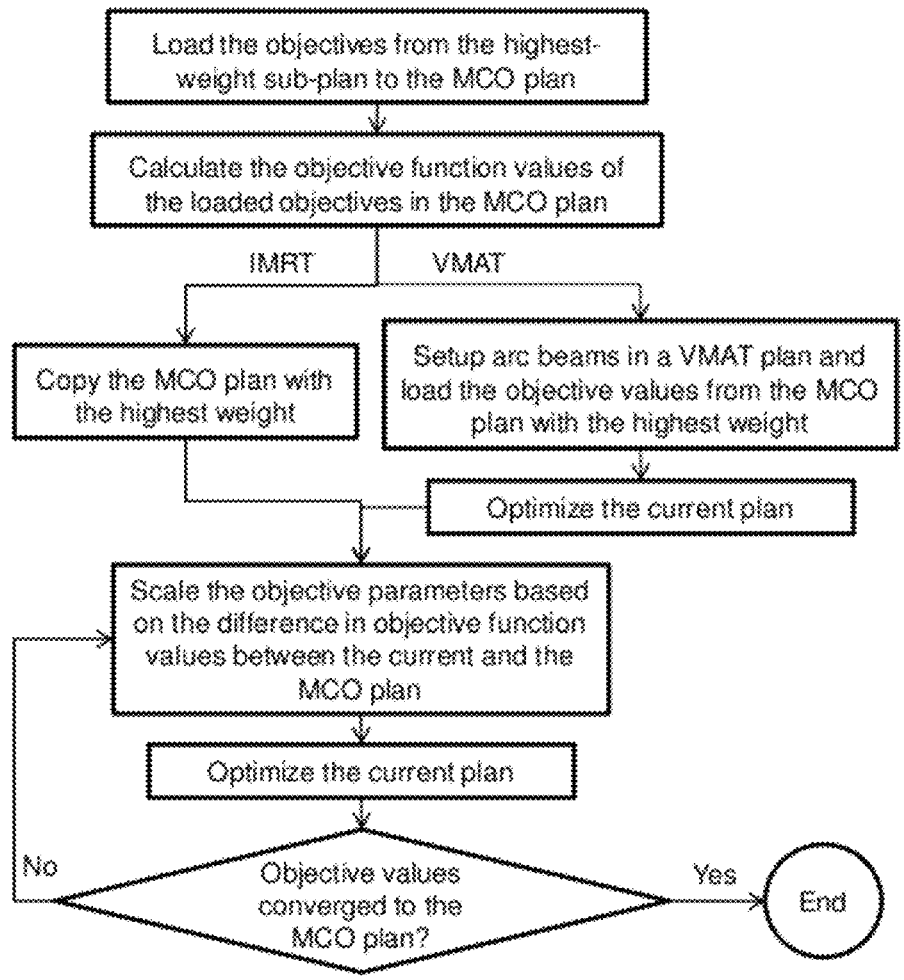

The AutoPlan multi-criteria optimization (MCO) method generates a few different plans, each which favor of a target organ or an organ-at-risk (OAR) based on the initial input plan which is generated from the non-constrained AutoPlan method. The purpose of the MCO algorithm is to explore multiple possibilities in the PTV coverage and/or different OAR sparing options. The MCO algorithm works on the basis of the initially generated autoplan and produces a couple of different PTV/OAR-favored plans, each of which provides the best possible coverage or sparing of the PTV or an OAR while maintaining the overall quality of the plan acceptable. FIG. 12(a) illustrates the work flow of the MCO algorithm for lung cancer with non-constrained objectives, as an example. First, the MCO algorithm examines the OARs to determine if the heart and the esophagus sparing conflicts with the lung sparing when trying to improve the plan quality. Then, MCO generates the PTV-favored plan based on the initial autoplan and the lung-favored plan is generated based on the PTV-favored plan. Next, the PTV-favored plan (if the lung sparing conflicts with the heart sparing) or the lung-favored plan (if the lung sparing does not conflict with the heart sparing) is used as the basis for generating the heart-favored plan. Similarly, the esophagus-favored is generated based on either the PTV-favored plan (if the lung sparing conflicts with the esophagus sparing) or the lung-favored plan (if the lung sparing does not conflict with the esophagus sparing). The resulted plans from above steps are then combined to produce a composite plan, which can be reviewed and adjusted by the physician. If a different compromise is preferred, the physician can easily change the weight of each input plan by sliding bars and observe the adjusted plan immediately. After the physician has come to a satisfied plan, the MCO can reproduce the final plan based on the weight settings adjusted by the physician. In such way, a plan with the physician's desired compromise is generated.

FIGS. 12(b)-(e) illustrates the work flows of steps 2-5 shown in FIG. 12(a). The PTV-favored plan is generated based on the final plan from the non-constrained AutoPlan method. First, the objective weight of each non-PTV objective is multiplied by a scaling factor (F) which is less than 1, for example, and then optimize the plan without resetting the beams. These two steps are repeated if the heterogeneity index (HI) of the PTV has not converged. Finally, examine the maximum dose in the cord; if it has exceeded the threshold (DT), reduce the dose value of the cord objective and re-optimize the plan; repeat this procedure until the criteria is satisfied and the final plan is saved as the PTV-favored plan.

The lung-, heart-, and esophagus-favored plans are generated in a similar way. The major difference lies in the initial plan on which it based on, as described above. The total objective value of corresponding OAR in each plan is adjusted to ⅔, for example, of the total objective value by scaling the objective weight and then optimization is executed. Such procedure is repeated until the PTV HI drops below a given threshold. The final plan is saved as the OAR-favored plan after the cord maximum dose is pushed to below the cord maximum dose criteria.

FIG. 12(e) illustrates a screenshot of the GUI which is currently implemented inside the Philips Pinnacle system. When clinician/planner adjusted the weights of relative weight of base plans interactively, the DVH and dose distributions can be adjust in real time. The decision of picking the best plans can be made at this stage.

After the decision was made, it is possible to deliver the 5 different plans in one fraction or deliver one of the plan in one fraction. Here, another method is used generate only one plan based on the final DVHs. In the plan explorer process, all the base plans were generated using fixed beam IMRT technology, however, final plan can be either IMRT plan or VMAT plan. The algorithm to generate one plan based on the MCO_plan is described in FIG. 12(g).

G. Automated Adaptive Planning (AAP) Method for ART

Large inter-fractional anatomical change may occur during fractional radiation treatment. Adaptive techniques such as isocenter re-positioning are effective when tumor only exhibits translational shift. To fully take advantages of the image-guided techniques, the ideal adaptive planning strategy is to perform the replanning based on the daily CTs. However, The complete replan for daily CT is impractical with the manual recontouring and trial-and-error replanning process. In an embodiment of the invention, an automated adaptive planning (AAP) method, i.e. automated contouring and automated plan optimization is done without any manual intervention.

The AAP method involves two key steps: automated contouring, which maps the contours in planning CT to those in daily CT and automatic planning, which performs the inverse fixed beam IMRT and VMAT plan based on propagated contours in planning CT without manual intervention. In the automatic contouring process, for each daily CT, the demons deformable image registration algorithm (DIR) implemented in Insight Toolkit (ITK) was adopted to generate the voxel-to-voxel correspondences between the planning/simulation CT and daily CT. The contours on simulation CTs were mapped to the daily CT by the deformation vectors. In an embodiment of the invention, this method works well if no large gas bubbles exist in rectum. When the method detected the large gas bubbles existed in the target and rectum region, a post contour adaption process that excluded the gas from the target and added the gas as a part of rectum's contour was performed. In the automatic planning process, AutoPlan as described in FIGS. 4-6 were used to generate autoplans without human intervention.

H. Evaluation of Autoplans

Evaluation of autoplans may be done by a physician or by evaluation of the following: Equivalent Uniform Dose (EUD), Tumor Control Probability (TCP), Normal Tissue Complication Probability (NTCP), dose volume data for example mean lung dose, lung v5, V10, V20. Heterogeneity Index (HI), Conformality Index (CI), complication free tumor control probability (P+). These parameters from an autoplan may be evaluated against a dosimetrist created plan parameters to determine the quality of the autoplan.

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

AutoPlan for Use in Generating Treatment Plans for Lung Cancer Tumors

A. Treatment Plan Expert Database

A treatment plan expert database was created from 150 lung cancer cases previously designed by dosimetrists. In this database, the tumor position, beam angles (gantry, couch, collimator angles), and tumor sizes were recorded for each plan. The expert database served as the base for the beam angle selections of the beam angle algorithm.

B. Beam Angle Selection Based on Expert's Experience

Figure 14:
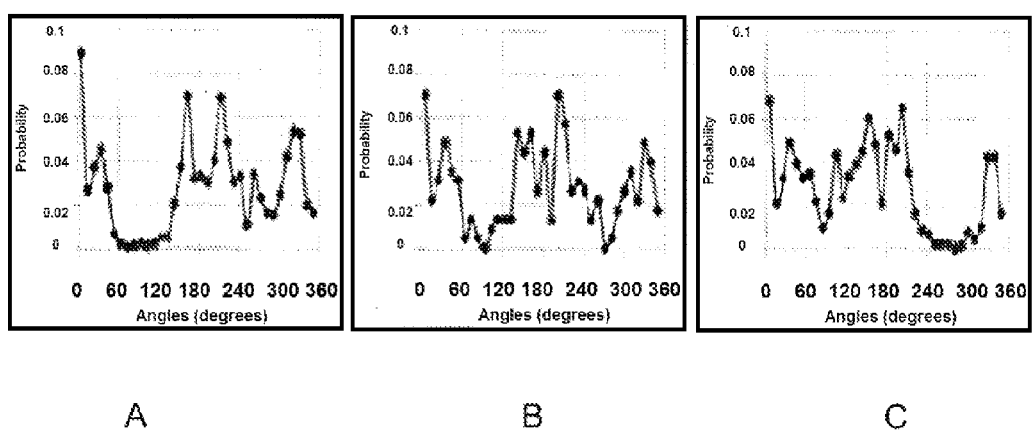
FIG. 14 illustrates the frequency distribution of beam angles used by dosimetrists in lung cancer IMRT plans from the expert system, categorized by tumor position (left (A), middle (B), and right (C)).

Step 1 in FIG. 4 mainly involves the selection of coplanar and non-coplanar beam angles for each plan. The tumor position was defined in left, middle and right position of the lung. In FIG. 14, shows the frequency distribution of coplanar beam angles selected by the expert dosimetrists for treatment of lung cancer. The angle distribution for tumors located at the left side of lung is different from that used on the right side of the lung. For example, if the tumor is located on the left side of lung, gantry angles 60, 120 are never selected by the expert dosimetrists. The tumor location was first determined (left, middle, or right), and 14 coplanar beams were sampled using the distribution in FIG. 14, from the expert system, to select the initial coplanar angles. Selecting non-coplanar beam angles is difficult and requires a great deal of treatment-planning experience. It is also a difficult problem for the computer algorithm since the combination of gantry and couch is much larger than the number of gantry alone. Adopting a brute force approach and selecting all possible gantry and couch combinations as the initial set of beam angles creates an intractable problem in terms of computer speed and memory use. In addition, some combinations of gantry and couch beam angles will cause the gantry to collide with the patient or couch. As such, instead of using the brute force method, heuristic knowledge gained from an expert database is used to select the non-coplanar beam angles. By examining the database it is observed that: only one or two non-coplanar angles are used by the dosimetrists in the expert system. Non-coplanar angles are used mainly in difficult clinical plans and these non-coplanar angles used the dosimetrists are appropriate and do not cause gantry-couch collision. To select non-coplanar angles, the tumor location was first determined and suitable previous patient matches from the database based on tumor location were identified. The five most commonly used non-coplanar angles from these matched patients were then sampled. In total; 19 angles were selected (14 coplanar and 5 non-coplanar) as the initial angles.

Additionally, initial beam angles may be selected from a method that directly assigns the beam angles to a new patient based on the best matching the tumor position of the new patient with that of the patient in the expert database. This method may design the plan faster than the one using 19 initial angles selected from the frequency distribution of like patients. This method will perform better if the expert database is comprehensive and contains all possible scenarios encountered in clinical practice.

C. Initial Objective Function

In step 2 of FIG. 4, the objective-function parameters are determined. FIG. 8 and table 1 lists the structures used for optimization and their initial values. Those structures and initial values are used for all lung cancer cases in this example. The FS-PTV is defined as the PTV. FS-LungAvoid, FS-CLungAvoid, FS-PrVCord, FSEsphogausAvoid, FS-HeartAvoid, FS-NTAvoid are defined as the lung, contralateral lung, cord, esophagus, heart, body minus the FS-PTVexp1 cm (PTV expanded isotropically 1 cm). Taking organ at risk (OAR) lung as an example, although the goal is to optimize the lung dose, FS-LungAvoid was used to achieve this goal. For most cases the lung will be overlapped with PTV and cause the conflicting objective if lung were used for optimization. FS-LungAvoid was used to avoid having conflicting objectives in the optimization algorithm. These initial objectives were the same for all of the lung patients in this Example. In one embodiment, standard objectives may used to automate the lung IMRT design. Equivalent uniform dose based objective function was adapted for the optimization. The maximum dose and minimum dose objective essentially corresponds to the EUD objective with parameter a approaches to positive and negative infinity. In one embodiment, an advantage of EUD based objective function compared with dose volume based objective function is that essentially only one parameter (target EUD) is adjusted in the objective function parameter automation (OFPA) loop, which makes the OFPA efficient and easy. EUD based objective function is a convex objective function, which makes the optimization algorithm well behaved and optimizing one EUD value will simultaneously optimize whole curve of dose volume histogram. Table 1 below lists the structures used for optimization and their initial values, which are used for all the lung cancer cases.

TABLE 1

| ROI | Type | Constraint | Target (cGy) | Volume (%) | Weight | a |
|---|---|---|---|---|---|---|
| FS-PlanPTV/FS-PlanITV | Min dose | Y | 7500 | | | |
| FS-PlanPTV | Uniform dose | N | 7500 | | 100 | |
| FS-PlanPTV/FS-PlanITV | Max dose | Y | 7500 | | | |
| FS-NTAvoid | Max DVH | N | 4000 | 0 | 10 | |
| FS-LungAvoid | MaxEUD | N | 4000 | | 1 | 1 |
| FS-CLungAvoid | MaxEUD | N | 240 | | 1 | 1 |
| FS-ILungAvoid | MaxEUD | N | 1000 | | 1 | 1 |
| FS-LungAvoid | Max DVH | N | 500 | 15 | 1 | |
| FS-HeartAvoid | Max DVH | N | 500 | 0 | 1 | |
| FS-PrvCord | Max DVH | Y | 4000 | 0 | | |
| FS-PrvCordRing | Max DVH | N | 4500 | 0 | 1 | |
| FS-PlanEsoph | Max DVH | N | 4000 | 0 | 1 | |
| FS-NTAvoid | Max Dose | Y | 5700 | | | |

Objective Function Parameter Automation

Figure 15A:
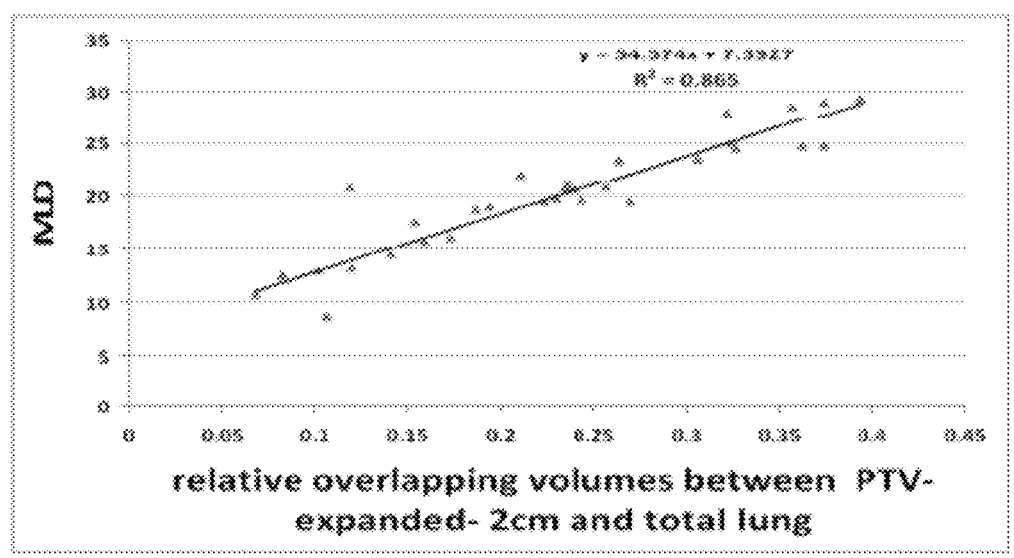
FIG. 15a shows the correlation between mean lung dose (MLD) and relative overlapping volumes between PTV expanded 2 cm and total lung for the clinical plans designed by clinical dosimetrists.
Figure 15B:
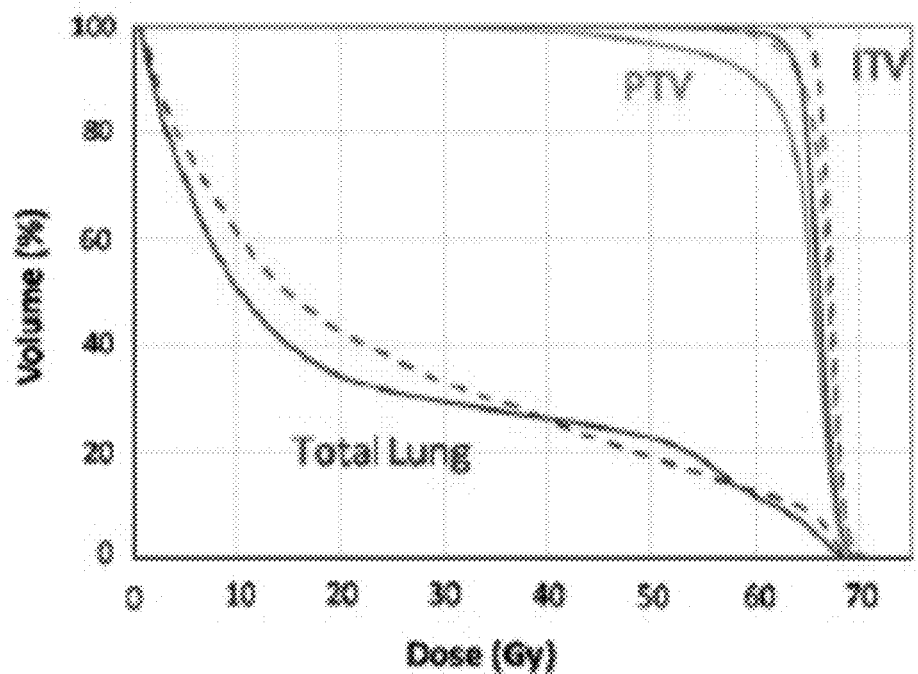
FIG. 15b is the DVH's of the plans designed using the PTV objectives (dashed lines) and ITV objectives (solid lines).

In step 3 of FIG. 4, the objective-function parameter is automatically adjusted using the flowchart displayed in FIG. 5. This work was performed at the mean lung dose (MLD) is constrained to 22 Gy. If a plan cannot achieve MLD less than or equal to 22 Gy, the PTV coverage has to be sacrificed to force MLD<22 Gy. In step 3, it is predicted whether MLD will likely exceed 22 Gy or not before choosing the initial target objective for the optimization. The MLD estimator is based on the volume (Lung-PTVexp2 cm-Volume) of overlap between lung and PTV isotropically expanded to 2 cm. FIG. 15a shows the MLD as a function of Lung-PTVexp2 cm-Volume for 100 patient cases which were planned by clinical medical dosimetrists. FIG. 15b shows the DVHs of the plans designed using the PTV objectives (dashed lines) and the ITV objectives (solid lines). A linear relation with correlation between MLD and Lung-PTVexp2 cm-Volume was determined. For a new patient case, the Lung-PTVexp2 cm-Volume is first calculated and the MLD for the case is then predicted based on the curve shown in FIG. 15. If the MLD is predicted to bigger than 24 Gy, the final plan's MLD is very likely to exceed 22 Gy. In this case, the ITV objective is chosen which is required to be uniform around a prescription dose. Below, it is seen that the choosing ITV based objective will naturally lead to the plan which has higher ITV/GTV coverage while sacrificing PTV coverage to satisfy the MLD constrains. This kind of plan is essentially the concomitant boost plan which is currently adopted to treat those very difficult cases. Choosing PTV based objective plan often leads to a plan with high PTV coverage.

FIG. 5b) displays the major workflow of the OFPO. For each functional objective parameter i, there are three parameters $EUD0_i$, weight (wi), ai parameter, and one objective function value fi. The constraint optimization available in Pinnacle planning system was highly adapted for use here. The FS-PTV/ITV was given maximum and minimum dose constrain to ensure the good target coverage and uniformity. The FS-NTAvoid was given constrained to ensure there is no hot region outside of the target. The cord was also given a hard constraint. There is no need to adjust objective function parameters if the objective is constrained. The uniform dose objective was also not adjusted for FS-PTV since this objective was given the highest weight possible, and is considered a constrained objective function parameter. For all other objectives, the OFPO using the approach called adjusting the objective value based on objective function value. A threshold objective function value Eobj was defined. Eobj can be considered as a user adjustable objective function value used by AutoPlan to control the convergence of the OFPO algorithm. In one embodiment, Eobj=0.2 was used for most non-constrained objectives and it was found that when objective function value exceeded Eobj=0.2 this lead to the degradation of other objectives. If a sub-objective function value fi is less than Eobj, the parameter $EUD0_i$ or $D_{0i}$ is reduced to make the fi value larger than Eobj by a binary search algorithm shown in FIG. 2b. In this example, the f0_low and the f0_high were set to Eobj−0.1 and Eobj+0.1.

D. Beam Angle Automation

Steps 4 and 5 in FIG. 4 comprise the beam-angle automation (BAA) loop. The underlying principle for this algorithm is that an IMRT plan with more beams should not be inferior to an IMRT plan with fewer beams if the optimization algorithm is well implemented. If fewer beams are better, the optimization algorithm should then turn off the extra beams automatically. However, most optimization algorithms made it difficult for the optimizer to turn off a beam completely. This problem can probably be solved using the regulation technique, which is commonly used in the optimization community. In this Example, two approaches are used to overcome this problem: 1) the initial angles, based on the expert database, had already eliminated many beam directions; and 2) steps 4 and 5 were used to delete beams with lower weights and the beam intensities were re-calculated to determine whether eliminating the beams with lowest weights deteriorates the plan quality.

E. Patient Selection and Study Design

In this example, AutoPlan was implemented as a research plug-in to Pinnacle and all plans generated from AutoPlan are deliverable plans which could directly be used to treat patients.

Five stage III non-small cell lung cancer (NSCLC) cases were re-planned using the AutoPlan system and compared with the plans created by dosimetrists and used to treat the patients. Those five cases were the same five cases adopted in previous work comparing the passive scattered proton plan and IMRT plans (Chang, Zhang et al. 2006). Dose volume data and conformality index (CI) were used to compare autoplan and clinical plan. The CI is defined as the volume enclosed by the prescription line divided by volume of PTV.

One stage III non-small cell lung cancer (NSCLC) case was re-planned using different strategies: 1) autoplan using the AutoPlan system; 2) autoplan-cop using the parameter optimization method but with 19 coplanar initial beam angles; 3) autoplan-db using the parameter optimization method but with beam angles selected using the angles best matched in the beam angle database; and 4) autoplan-cb using the parameter optimization algorithm but with the beam angles selected by an experienced dosimetrists.

To demonstrate a rational behind the BOA algorithm the plan was also studied for the above patients using 19, 18, 17, 16, . . . , 5 beams. For plans optimized using n (n<19) beams, the beams for the plan optimized using n+1 beams with the lowest weights were deleted. The total score of the objective function, CI, HI, lung V5, P+ was computed for the plans with the different number of beams.

F. Impact of Number of Beam Angles on the Plan Quality

Table 2 used various metrics to compare the plan quality among plans using different number of beam angles. The corresponding value of the clinical plan used to treat this patient is also listed. The clinical plan used 5 non-coplanar beam angles with gantry angles (345, 40, 90, 140, 190). The overall plan quality was measured using the total score, P+ and Hot-Region. This patient was prescribed 200 cGy per fractions to 93% of PTV mean dose for 30 fractions. The standard prescription dose in an institution is 63 Gy. However, for this patient, since mean lung dose (MLD) reached 21.5 Gy. It was forbidden to treat the patient with MLD>22 Gy and only 60 Gy prescription dose was given. This case was considered a very challenging case and the dosimetrists spent a significant effort to design the clinical plans. Since the prescription dose was 60 cGy, the absolute volume receiving dose>=50 Gy in the normal tissue region was used to describe the unnecessary radiation to the patient. The overall plan quality was significantly improved for the autoplans for all beam configurations ranging from 5 to 19 beams compared with the clinical plans in terms of total score, P+ and Hot-Region in the normal tissue. The total score was defined with the objective function used in the AutoPlan system which is different from the one used for the clinical plan. P+ which reflected the complication free tumor control probability improved absolutely 9.54% (7.4%-11.2%) in autoplans compared with clinical plans. The unnecessary irradiation to the normal tissue region was also reduced 332 cc (270 cc-376 cc). The autoplan with 13 beams reached the lowest total score but P+ was lowest in autoplan with 5 beams and 13 beams. The target coverage was reflected in V prescription, CI, HI, TCP. The volume covered by the prescription dose was 93.8% (92.5%-94.8%) which is about 1% lower than that of clinical plan 94.8%. CI, HI, TCP in autoplans was 1.08 (1.07-1.09), 1.16 (1.12-1.20), 78.0% (77.8%-78.3%) compared to 1.34, 1.13, 77.1% in clinical plan. When the number of beams is greater than 12, the HI index was slightly improved. When the number of beams is less than 8, the PTV receiving the prescription dose was reduced. The lung sparing was reflected in V5, MLD and NTCP. V5, MLD, NTCP were 58.1% (56.2%-60.2%), 19.2 Gy (19.0 Gy-19.5 Gy) and 10.8% (9.7%-12.9%) in autoplans compared to 63.4%, 21.5 Gy and 22.6% in clinical plans. When number of beams is less than 9, the MLD in autoplans was about 0.4 Gy higher than that in autoplans with number of beams greater than 8. The heart, cord, esophagus sparings were represented by the NTCP values. The NTCP values for heart, cord, esophagus in autoplans were 0, 0, and 30.6% (27.1%-32.3%) compared to 0, 0, 31.3% in clinical plans. For this patient, esophagus was overlapped with PTV which leading to larger NTCP value of esophagus for all plans.

TABLE 2

Table 2: Various metrics to compare the autoplan quality among plans using different number of beam angles.

| Beams/plan | Overall plan quality | | | Target coverage | | | Lung sparing | | | | Normal tissue sparing | | |
|---|---|---|---|---|---|---|---|---|---|---|---|---|---|
| | P+ (%) | Hot-R | $V_{prescription}$ (%) | CI | HI | TCP | MLD (Gy) | V5 (%) | NTCP-L (%) | Cord $D_{max}$ (Gy) | NTCP-H (%) | NTCP-Cord (%) | NTCP-Eso (%) |
| 19 | 38.9 | 1.52 | 94.4 | 1.07 | 1.16 | 78.0 | 19.2 | 60.2 | 10.3 | 40.6 | 0 | 0 | 32.0 |
| 18 | 38.9 | 1.41 | 94.5 | 1.08 | 1.12 | 78.2 | 19.1 | 59.7 | 10.1 | 40.7 | 0 | 0 | 32.0 |
| 17 | 40.1 | 1.46 | 94.7 | 1.07 | 1.12 | 78.1 | 19.1 | 59.8 | 10.1 | 40.9 | 0 | 0 | 31.0 |
| 16 | 39.9 | 1.37 | 94.8 | 1.08 | 1.12 | 78.3 | 19.1 | 59.8 | 10.5 | 41.3 | 0 | 0 | 31.0 |
| 15 | 39.5 | 1.42 | 94.6 | 1.08 | 1.12 | 78.0 | 19.1 | 59.8 | 10.1 | 40.6 | 0 | 0 | 31.5 |
| 14 | 39.6 | 1.48 | 94.1 | 1.09 | 1.13 | 78.0 | 19.1 | 56.5 | 10.9 | 40.9 | 0 | 0 | 30.7 |
| 13 | 41.0 | 1.43 | 93.6 | 1.07 | 1.13 | 77.8 | 19.0 | 56.1 | 10.5 | 39.9 | 0 | 0 | 29.3 |
| 12 | 40.2 | 1.41 | 93.8 | 1.08 | 1.18 | 77.9 | 19.0 | 56.9 | 10.5 | 40.6 | 0 | 0 | 30.2 |
| 11 | 40.8 | 1.48 | 93.8 | 1.08 | 1.18 | 78.1 | 19.1 | 57.3 | 10.6 | 40.4 | 0 | 0 | 29.8 |
| 10 | 38.9 | 1.52 | 93.6 | 1.08 | 1.18 | 78.1 | 19.0 | 57.2 | 10.2 | 41.6 | 0 | 0 | 32.3 |
| 9 | 39.9 | 1.19 | 93.6 | 1.07 | 1.18 | 78.0 | 19.0 | 58.0 | 9.7 | 39.4 | 0 | 0 | 31.3 |
| 8 | 37.6 | 1.57 | 94.1 | 1.09 | 1.17 | 78.3 | 19.4 | 58.8 | 11.7 | 41.2 | 0 | 0 | 32.8 |
| 7 | 40.3 | 1.86 | 92.4 | 1.08 | 1.20 | 78.0 | 19.4 | 57.8 | 12.1 | 40.9 | 0 | 0 | 29.1 |
| 6 | 39.1 | 1.97 | 92.5 | 1.09 | 1.20 | 77.9 | 19.5 | 56.2 | 12.9 | 44.0 | 0 | 0 | 29.6 |
| 5 | 41.4 | 1.69 | 92.5 | 1.09 | 1.19 | 77.8 | 19.5 | 57.2 | 12.6 | 43.0 | 0 | 0 | 27.1 |
| Clinical | 30.2 | 3.95 | 94.8 | 1.34 | 1.13 | 77.1 | 21.5 | 63.4 | 22.6 | 48.0 | 0 | 0.1 | 31.3 |

The corresponding value of the clinical plan used to treat this patient was also listed. P+: total complication free tumor control probability. Vprescription: relative volume enclosed by the prescription dose; CI: conformality index; HI: Heterogeneity index; TCP: tumor control proballity; MLD: mean lung dose; V5: relative volume receiving dose greater than 5Gy. NTCP: normal tissue complication probability; NTCP-L: NTCP for lung; NTCP-H: NTCP for heart; NTCP-C: NTCP for cord and NTCP-Eso: NTCP for esophagus.

Figure 16:
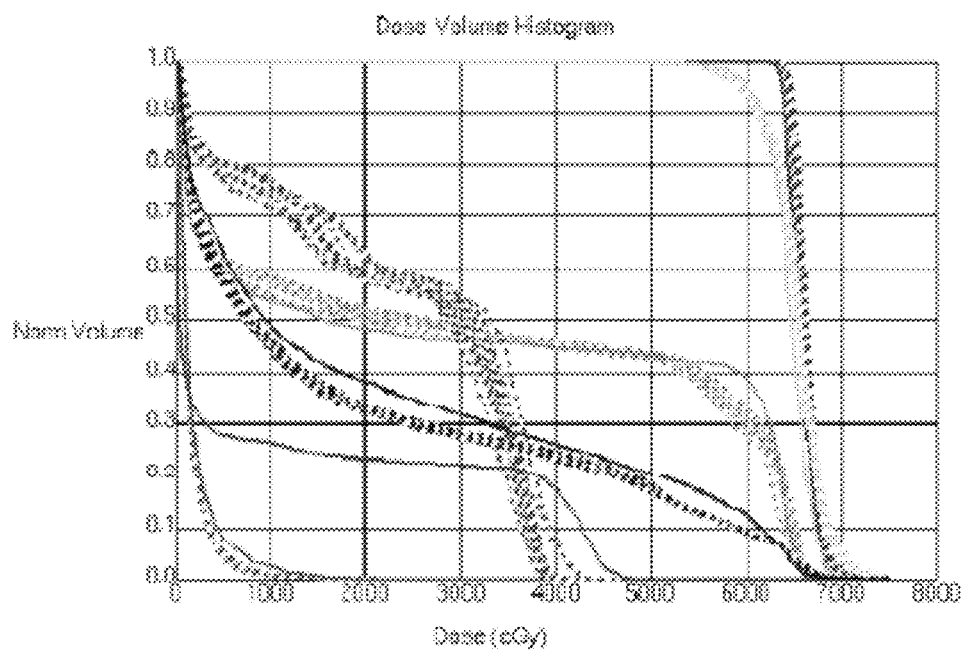
FIG. 16 is a dose volume histogram of the plans generated by AutoPlan system for a lung cancer case with 5-19 beams (dashed lines) and clinical plan (solid line)

FIG. 16 displays dose volume histograms of autoplans compared with clinical plans. Together with results shown in table 1, it is seen that difference of plan qualities among plans with different number of beams is small. However, autoplans were consistently better than clinical plans no matter how many beams were used. It was observed that plans with 11 beams were not worse than the plans greater than 11 beams.

Although the results shown in Table 1 and FIG. 16 were obtained for one patient, a similar study for other patients was done and it was found the results are quite similar among different patients.

G. AutoPlan Algorithm Yields Better Plan Compared to Other Strategies

Table 3 used various metrics to compare the plan quality among plans designed using different strategies. The automation method essentially contains beam angle selection automation (BAA) and objective function parameter selection automation (OFPA). OFPA-CB represented the scenario that a perfect match of this patient in the expert database existed. OFPA-DB represented the scenario that a perfect match did not exist but a closest match existed. Lung V5 is lower in OFPA-CB but MLD is similar. Interestingly, NTCP of plan OFPA-DB is lower than that of OFPA-CB. There are no significant differences in target coverage and critical structure sparing among these two plans. V5 is considered as one of the most important metrics for the lung sparing in the institution this study was performed in. OFPA-CB is strongly preferred and considered better plan. The difference between autoplan-5B and autoplan-coplanar is that the initial angles of former contained both coplanar and non-coplanar angles and initial angle of latter only contained 19 equal spaced coplanar angles. The MLD of autoplan-5B is about 1 Gy lower than that of autoplan-coplanar. This is considered significant for the lung plan quality. When autoplan-5B is compared with autoplan-11B (table 3), autoplan-11B is generally better than autoplan-5B in terms of target coverage and lung sparing (MLD of autoplan-11B is 0.4 Gy lower than that of autoplan-5B). Although the difference is small, clinicians normally weigh more on the plan quality than the delivery efficiency especially for the plan which was very hard to meet the plan constrains. In this implementation of the AutoPlan method, the plans were generated with a number of beams from 11 beams to 5 beams and the decision of picking the plan to treat patients was left to clinicians.

TABLE 3

Table 3: Various metrics to compare the autoplan quality among plans using different planning strategies.

| Plans | Overall plan quality | | | Target coverage | | | | Lung sparing | | | Normal tissue sparing | | | |
|---|---|---|---|---|---|---|---|---|---|---|---|---|---|---|
| | P+ (%) | Hot-R (%) | MU | $V_{prescription}$ (%) | CI | HI | TCP (%) | MLD (Gy) | V5 (%) | NTCP-L (%) | Cord $D_{max}$ (Gy) | NTCP-Cord (%) | NTCP-H (%) | NTCP-Eso (%) |
| Auto plan-cop | 34.80 | 3.94 | 599 | 93.4 | 1.14 | 1.18 | 78.1 | 20.6 | 57.1 | 18.5 | 44.1 | 0.0 | 0.0 | 30.3 |
| OFPA-DB | 33.70 | 1.66 | 633 | 93.8 | 1.06 | 1.20 | 79.1 | 20.3 | 62.7 | 14.6 | 44.5 | 0.0 | 0.0 | 36.0 |
| OFPA-CB | 35.70 | 2.14 | 659 | 93.0 | 1.03 | 1.21 | 78.8 | 20.3 | 56.2 | 15.1 | 44.8 | 0.0 | 0.0 | 32.8 |
| Autoplan-5B | 41.40 | 1.69 | 583 | 92.5 | 1.09 | 1.19 | 77.8 | 19.5 | 60.9 | 12.6 | 43.0 | 0.0 | 0.0 | 27.1 |
| Clinical | 30.20 | 3.95 | 670 | 94.8 | 1.34 | 1.13 | 77.1 | 21.5 | 63.4 | 22.6 | 48.0 | 0.1 | 0.0 | 31.3 |

Figure 11:
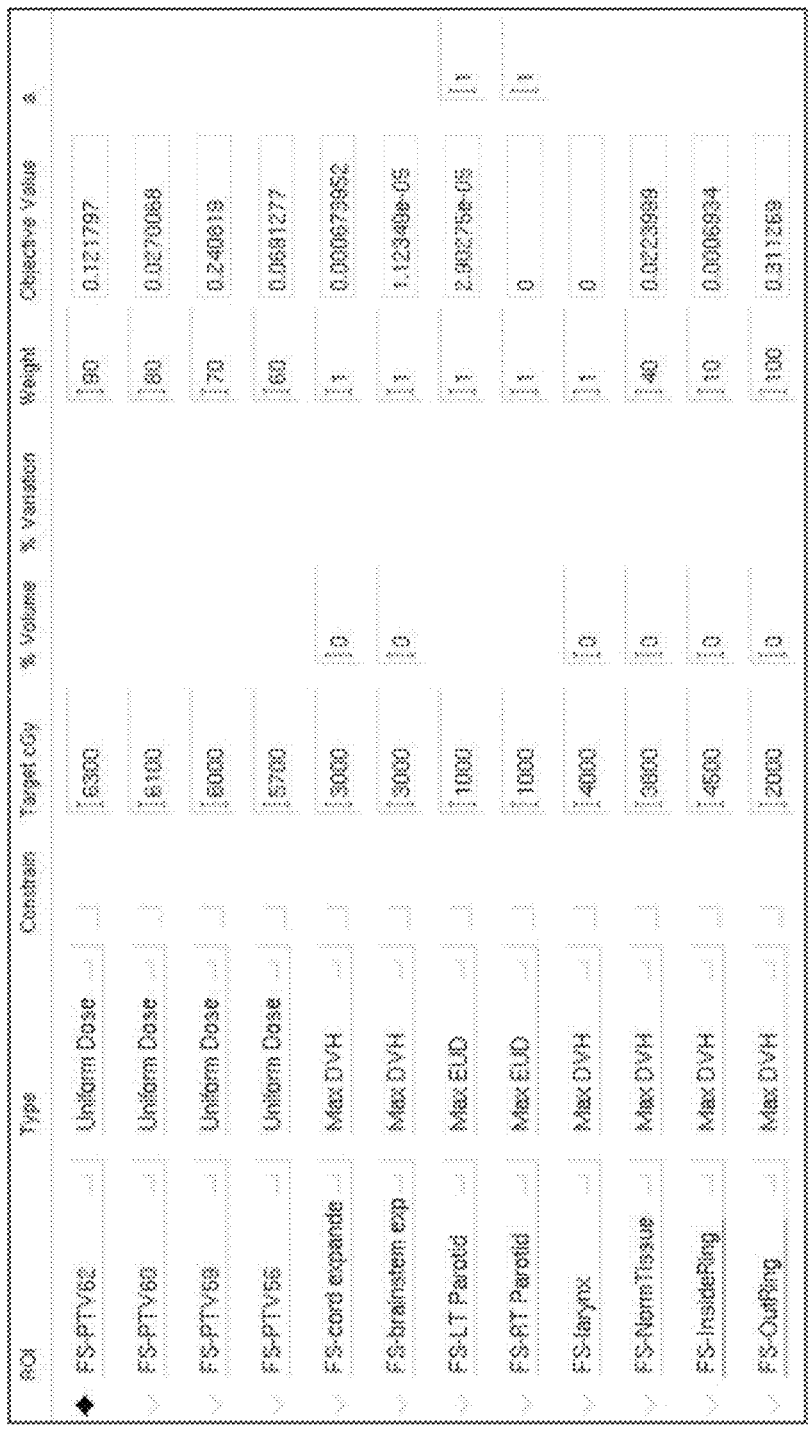
FIG. 11 is a screen shot of the planning structures and initial objective function parameters used in some embodiments of head neck plans for the AutoPlan System.

The different strategies was given in the explanation of FIG. 11. The corresponding value of the clinical plan used to treat this patient was also listed.

Figure 17:
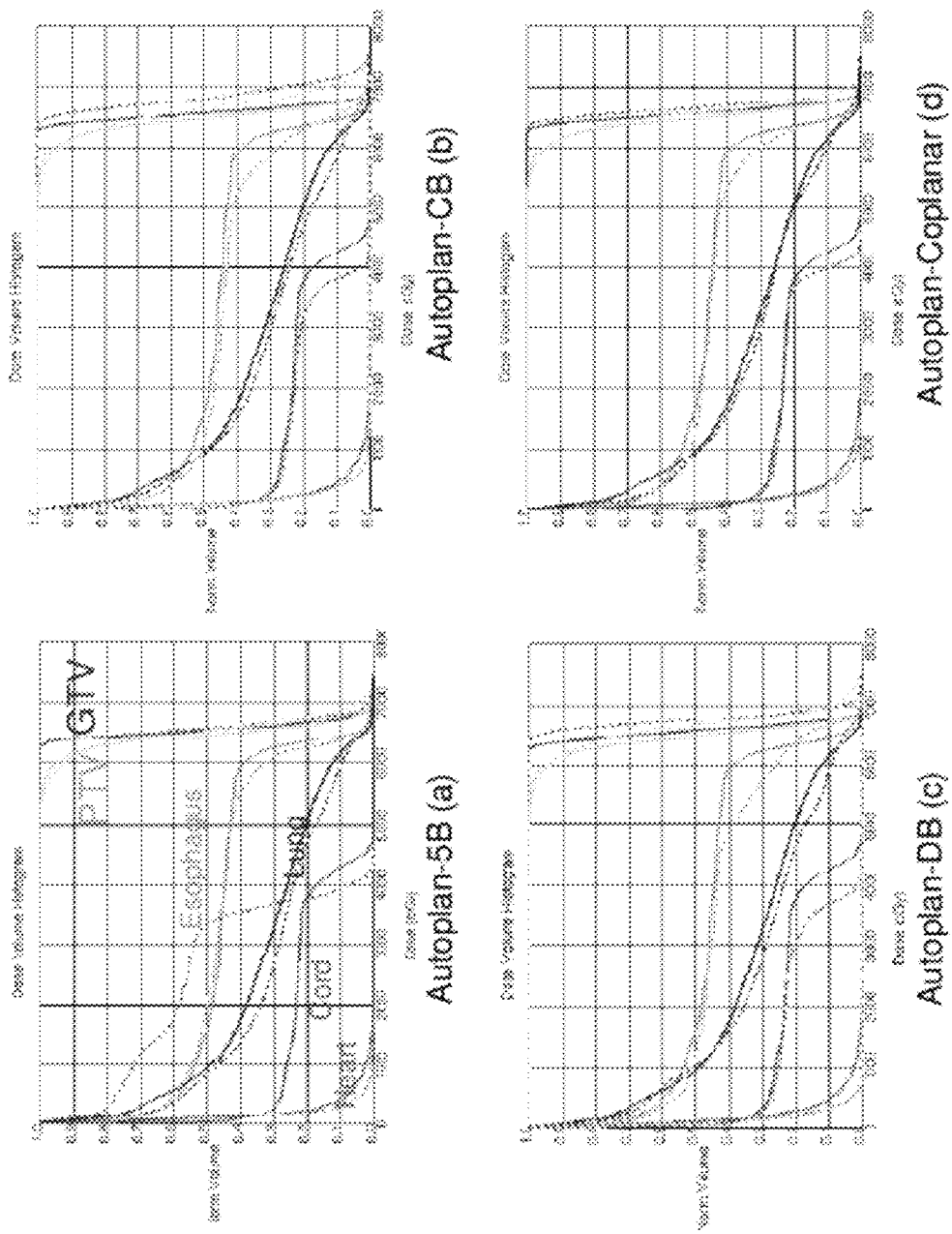
FIG. 17 shows dose volume histograms of the plans generated by AutoPlan system with different strategies. a) autoplan-5B: autoplan with 5 beams generated using simultaneous BAA and OFPA algorithms; b) autoplan-CB: autoplan with beams selected by medical dosimetrists by optimized by OFPA; c) autoplan-DB: autoplan with beams selected by best match this cases with the cases stored in the beam angle expert database by optimized OFPA; d) autoplan-Coplanar: autoplan with beam angles without non-coplanar angles optimized by BAA and objective function parameters optimized by OFPA.

FIG. 17 shows dose volume histograms (DVHs) for the plans optimized using different strategies. The DVH of clinical plan was also plotted to show the degree of improvement for each strategies. There is a tendency that the PTV is more heterogeneous in plans optimized using AutoPlan than in clinical plans. The critical structure is consistently better spared in plans optimized by AutoPlan. Since autoplan-CB, autoplan-DB and autoplan-coplanar all used coplanar beam only, the advantage of using non-coplanar beams can be seen from comparing the DVHs of those plans with those of autoplan-5B. It is seen that when using non-coplanar beams, better lung sparing was achieved by increasing the low dose region spinal cord and reducing the low dose region in lung. Since only the maximum dose of spinal cord was concerned, the better dose shaping capability by using non-coplanar beam is strongly desired.

Figure 18:
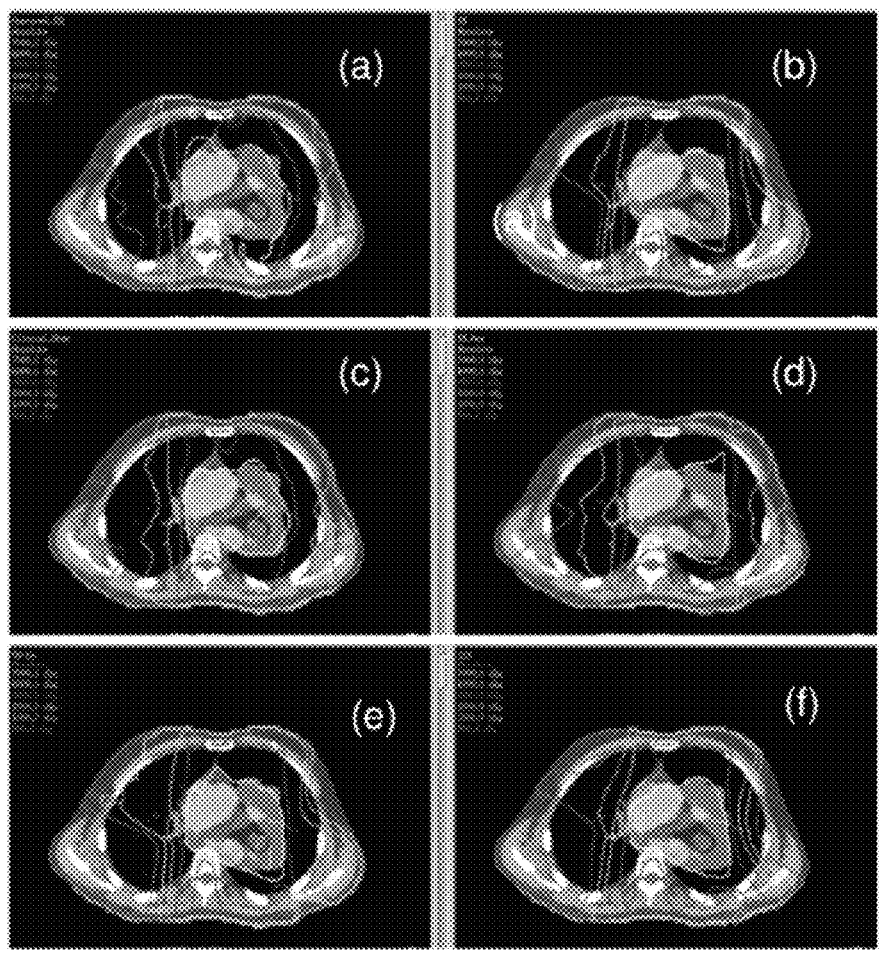
FIG. 18 shows iso-dose distributions of the plans generated by AutoPlan system with different strategies compared with clinical plans: a) clinical plans used to treat this patient; b) autoplan with 5 beams generated using simultaneous BAA and OFPA algorithms; c) autoplan with 5 beams selected by medical dosimetrists by optimized by OFPA; d) autoplan with 5 beams selected by best match this cases with the cases stored in the beam angle expert database by optimized OFPA; e) autoplan with 5 beam angles without non-coplanar angles optimized by BAA and objective function parameters optimized by OFPA; f) autoplan with 11 beams generated using simultaneous BAA and OFPA algorithms.

FIG. 18 shows the iso-dose distribution for the plans optimized using different strategies. The clinical plan, autoplan-CB, autoplan-DB showed larger portions of contra-lateral lung were exposed by low dose (5 Gy) while autoplan-coplanar, autoplan-5B and autoplan-11B showed better contra-lateral lung lose dose sparing (5 Gy). Using non-coplanar beam, autoplan-5B and autoplan-11B also displayed better 20 Gy dose sparing. Among all the plans, autoplan-11B was the most desired. The conformality was greatly improved in all autoplans compared to clinical plan.

H. Judiciously Selected Planning Structures Improved Plan Quality

FIG. 19 displayed how judiciously selected planning structures can improve plan quality. FIGS. 19a) and b) compared the iso-dose distribution for the plans with/without FS-CordRingAvoid structure. Fs-CordRingAvoid was defined as the ring structure expanded PryCord 3 cm prosperously and laterally (in the contraleral lung direction). The maximum dose of cord is not allowed to exceed 45 Gy and both plans satisfied this requirement. However, it is often desired to let the dose in the FS-CordRingAvoid region not exceeding 45 Gy if it is possible. This requirement was often more desired if the plan is very easy to satisfy all other constraints. The planning structure FS-CordRingAvoid could lead to the much desired dose distribution as shown in FIG. 19b).

FIGS. 19c) and d) compared the iso-dose distribution for the plans with/without FS-ClungAvoid structure. Fs-CLungAvoid was defined as the structure obtained by contra-lateral lung subtract the PTV. Two important observations can be revealed by FIGS. 19c) and d): 1) beam angle selection is strongly dependent on the planning objectives and 2) clinical objectives were vaguely defined in the daily clinics. MLDs are 18.9 Gy and 18.0 Gy respectively for plan shown in FIGS. 13c) and d). However, plan shown in FIG. 19c) are strongly preferred by clinicians due to much better contra-lateral lung sparing. For the plan shown in FIG. 19d), the beam direction 280 was strongly favored and was given larger weight to achieve better target conformality and total mean lung dose reduction. However, the plan with better contra-lateral lung sparing was strongly preferred. As shown in FIG. 19d), adding the FS-ClungAvoid objective automatically deleted the beam direction 280 and resulted with a plan with much better contralateral lung sparing. Preferring plans with better contra-lateral lung sparing with similar or even a little bit worse MLD and the plan with better FS-CordRingAvoid was not written in any protocols but was implicitly adopted by clinicians. Those implicit rules are one reason why designing IMRT plan is still an art. The AutoPlan approach starts to incorporate those rules into this method and is an important step to truly automate the IMRT plan design.

I. mdaccAutoPlan Algorithm Yields Better Plan than Clinical Plans

Table 4 compared the average dose volume data for the plans of five patients between autoplans and clinical plans. In a previous study, it was found that PSPT plans significantly improve lung sparing compared to the clinical IMRT plans which were used to treat the patients. With the AutoPlan system available for lung cancer patients, it was observed that IMRT plans essentially achieved similar lung sparing (in terms of MLD) as PSPT plans do in one clinical trial which randomized the photon and proton treatment for stage III lung cancer patients. The five patients were re-planned with AutoPlan and the autoplans were compared with the clinical plans. It was found that MLD of autoplan is about 2 Gy less than clinical plans and is about the same the PSPT plans. In addition to lung sparing, cord, heart, esophagus sparings are also better in autoplans than in clinical plans. The autoplans are also more conformal (CI=0.8) than the clinical plans (CI=0.7) but slightly more heterogeneous (HI=1.2 in autoplans v.s. 1.1 in clinical plans). All autoplans of the five patients were reviewed by clinicians and were considered to be ready to treat those five patients without further review.

TABLE 4

Table 4: Average dose volume data for the plans generated by AutoPlan and by experienced clinical dosimetrists for the 5 patient cases which was also used in reference Chang and Zhang 2006.

| Total Lung | V5 | V10 | V20 | V30 | Mean (Gy) |
|---|---|---|---|---|---|
| Photon | 58.5 | 45.3 | 34.5 | 29.1 | 20.1 |
| Proton | 43.1 | 37.0 | 30.8 | 25.6 | 17.5 |
| autoplan | 51.9 | 38.3 | 28.8 | 24.6 | 17.4 |

| ROI | PTV (Vprescription) | Cord (Dmax) | Esophagus (V55) | Heart (V40) | CI | HI |
|---|---|---|---|---|---|---|
| Photon | 95.4 | 43.0 | 30.4 | 9.7 | 0.7 | 1.1 |
| Proton | 95.8 | 37.1 | 30.7 | 6.4 | | |
| autoplan | 95.0 | 37.9 | 26.7 | 8.5 | 0.8 | 1.2 |

The work above describes that the AutoPlan system has been adopted in a clinical trial which randomized proton and photon treatments for stage III lung patients to compare the clinical benefit of proton therapy. For that trial, initially, all photon IMRT plans were designed by both the AutoPlan system and experienced clinical dosimetrists. Plans designed by the AutoPlan system were consistently better or no worse than the plans designed by clinical dosimetrists. Since it was realized that AutoPlan consistently produced the IMRT plan which was hardly improved by manual intervention, the protocol was modified so that all the photon clinical plans were initially designed by the AutoPlan system. Randomization of the patients will be decided by the initial autoplans. If the plan was randomized to photon IMRT treatment, clinical dosimetrists will adjust the autoplan based on the radiation oncologist's preference if it is necessary. To all knowledge, the AutoPlan system is the first system which can essentially perform the IMRT design using one-button click and has started to be adopted in the real clinic practice.

Further, autoplans significantly improve lung sparing compared to the clinical IMRT plans which were used to treat the patients. It was also noticed that lung plan quality manually designed by medical dosimetrists was improved if they realized that the same plan was also being designed by AutoPlan system simultaneously.

Once beam angle selection was automated, the next important optimization process is objective function definition and objective function parameter automation. The planning structures were judicially selected so that every lung cancer cases were optimized by those planning structures. The AutoPlan method was tested on more than 100 lung cancer cases using the same initial planning structures (objective function parameters). It was shown that the planning structures also contained the implicit judgment of plan quality by radiation oncologists used in the expert system. The objective function parameter automation is striking efficient once initial beam angles and initial objective function parameters were judiciously selected. In practice, only 2-3 loops of OFPA were needed to obtain the final plan if beam angles were determined. Since the plans with 11 beams were frequently liked by radiation oncologists, the system can produce the autoplan with 11 beams in about 20 minutes automatically for a challenging stage III lung cancer case. With more powerful computers available and parallel dose calculation algorithms, it is expected that this 20 minutes may be easily reduced within 1 minute, which makes real time planning without manual intervention possible.

In the OFPA process, the total lung objective was set to (FS-LungAvoid) a value which is impossible to achieve which was reflected by the very high objective values for the optimized plan. The plan produced essentially corresponds to the lung optimal plan. It was found that this lung optimal plan is the plan which radiation oncologists most preferred especially for the challenged stage III lung cancer cases. It was also demonstrated by producing those lung optimal plans, that the target objectives and other critical structure objectives were also satisfied or even better than the plans manually designed by clinical dosimetrists. Based on this work, a system was designed with a multi-criteria approach which simultaneously produced several optimal plans and final plans which can then be evaluated and determined by a treatment plan explorer. This approach has been implemented.

Example 2

AutoPlan for Use in Generating Treatment Plans for Prostate Cancer Tumors

Eleven randomly selected prostate-cancer patients, each prescribed 76 Gy in 38 fractions, were studied. Each patient had a clinical plan that was generated by a dosimetrist using 8-beam IMRT with standard beam angles used in the treatment institution. A VMAT plan using two arcs (360-degree back and forth) was generated for each patient with autoplan algorithm. Also, a series of IMRT plans based on different numbers of beam angles were generated with the autoplan algorithm for each patient. For each patient, IMRT plan was started using autoplan with 8 beams with selected beam angles and the beam number was increased to 12, 16, and so on until the IMRT plan reach similar quality as the VMAT plan. All the autoplan-based IMRT plans used beam angles that one would consider would produce better organ-at-risk (OAR) sparing. Among the three usual OARs in prostate cancer, the femoral heads and the bladder are generally easy to spare compared to the rectum, which is usually overlapping with the PTV; reducing dose in the rectum has always been a difficult task. Therefore, in this Example, the beam-angle selection was mainly focused on better rectum dose sparing. All autoplan-based plans were optimized to the similar PTV coverage as the clinically approved plan for each patient in order to compare the plans on a fare basis. PTV coverage was assessed by the conformality index (CI), which is defined as $$CI = \frac{TV_{D_P}}{TV} \times \frac{TV_{D_P}}{V_{D_P}} \in [0, 1]$$

$TV_{D_P}$=Target volume covered by prescription dose
$TV$=Target volume
$V_{D_P}$=Volume enclosed by the prescription isodose surface
and the heterogeneity index (HI), which is defined as $$HI = \frac{D_1}{D_{95}}$$

$D_1$=Dose encompassing 1% of the target volume
$D_{95}$=Dose encompassing 95% of the target volume Average OAR volume within 30-60 Gy isodose lines and the average mean dose for the rectum and the bladder were calculated and compared for each category of plans. The average total MUs per fraction were also compared to assess the cost in dose delivery time.

Figure 20:
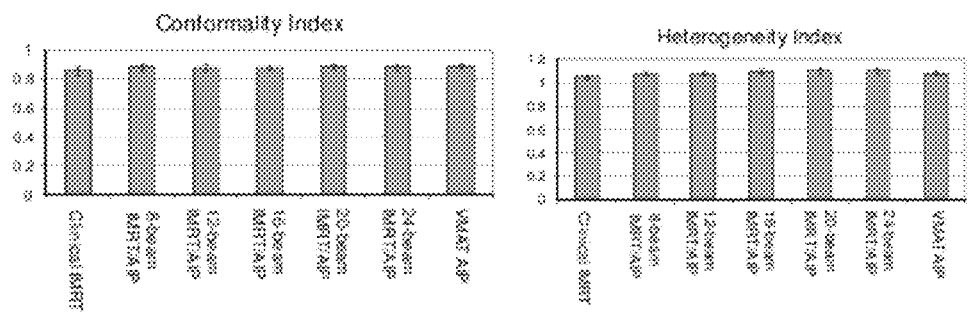
FIG. 20 shows average PTV conformality index (left) and heterogeneity index (right) of the 11 patients from each type of plan. The two plots show that all plans have reached essentially the same level of PTV coverage.
Figure 21:
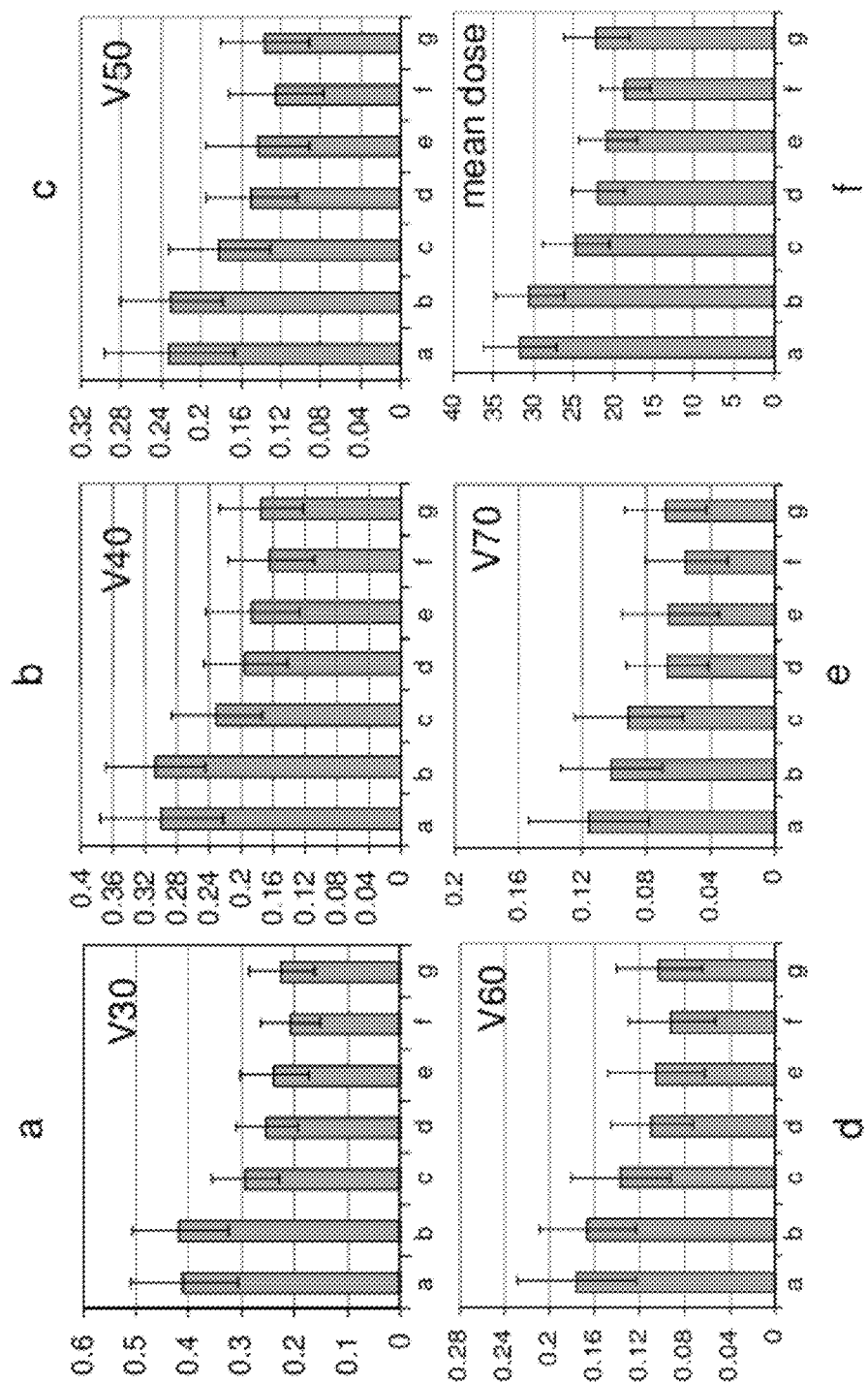
FIG. 21 show the dose statistics in the rectum for the 11 patients from the clinical plan (a), 8-beam IMRT autoplan (b), 12-beam IMRT autoplan (c), 16-beam IMRT autoplan (d), 20-beam IMRT autoplan (e), 24-beam IMRT autoplan (f), and the VMAT autoplan. Each plot corresponds to the percentage volume at respectively 30, 40, 50, 60, and 70 Gy, and the mean dose in the rectum. autoplans generally show lower dose than the clinical plans. When the number of beams in IMRT is low, IMRT plans show higher dose than the VMAT plan; as the number of beams increases, IMRT shows the trend to produce lower dose than VMAT.
Figure 22:
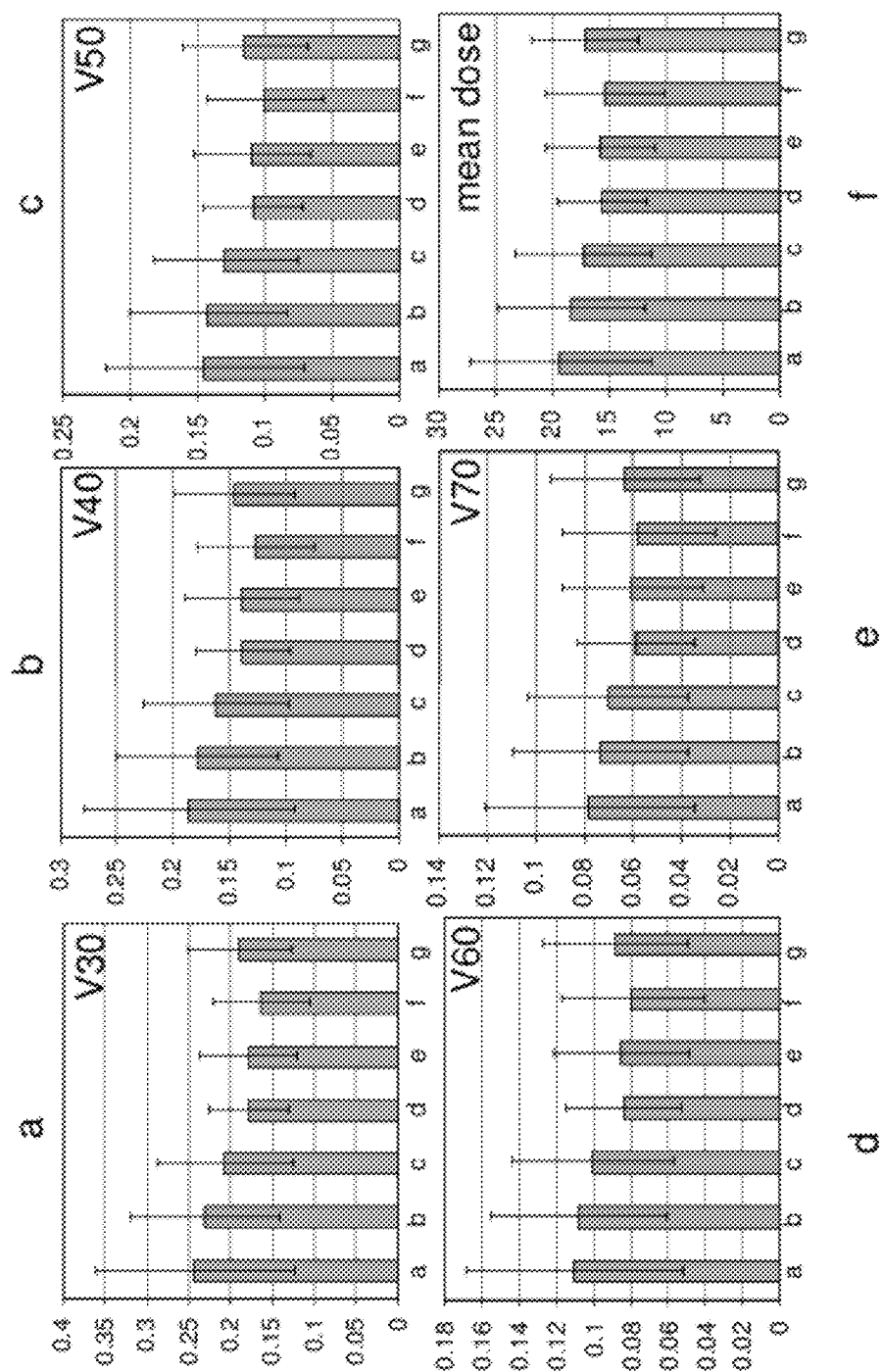
FIG. 22 shows dose statistics in the bladder for the 11 patients from the clinical plan (a), 8-beam IMRT autoplan (b), 12-beam IMRT autoplan (c), 16-beam IMRT autoplan (d), 20-beam IMRT plan (e), 24-beam IMRT autoplan (f), and the VMAT autoplan. Each plot corresponds to the percentage volume at respectively 30, 40, 50, 60, and 70 Gy, and the mean dose in the rectum. autoplans generally show lower dose than the clinical plans. When the number of beams in IMRT is low, IMRT plans show higher dose than the VMAT plan; as the number of beams increases, IMRT shows the trend to produce lower dose than VMAT.

By using the autoplan algorithm, all of the IMRT and the VMAT plans generated in this example have reached comparable PTV coverage to the clinical plans in terms of conformality and heterogeneity, as shown in FIG. 20-22. With similar PTV coverage, it was observed that all autoplan-based plans have produced at least comparable normal tissue sparing to the clinical plans. FIGS. 21 and 22 show the average percentage isodose volumes at 30-60 Gy and average mean dose in the rectum and the bladder for the 11 patients. For both OARs, autoplans generally show lower dose than the clinical plans, especially for the rectum. VMAT plans produced significant dose reduction compared to the IMRT plans when fewer beams were used; however, as the number of beams increases, IMRT shows the trend to produce even lower dose than VMAT.

Figure 23:
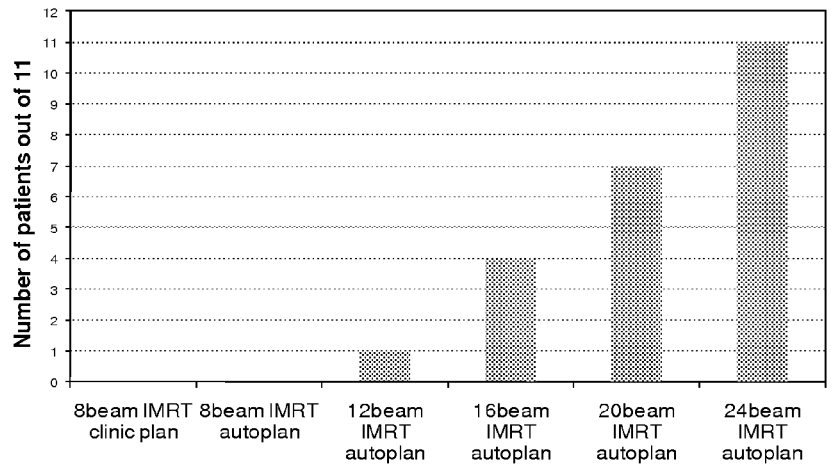
FIG. 23 shows the number of patients who received better rectum sparing from the IMRT autoplan than from the VMAT autoplan for each type of IMRT plans. Patients show great variations in terms of the number of beams required for IMRT plans to exceed VMAT.

It was also observed that different patients show great variations in terms of the number of beams required for IMRT to exceed VMAT plan quality: some patients require fewer beams, some require more. Among the 11 patients involved in this example, the minimum and maximum numbers of beams required are, respectively, 12 and 24. FIG. 23 shows the number of patients who received better plan quality from each type of autoplan-based IMRT plan than from the autoplan-based VMAT plan.

Figure 24:
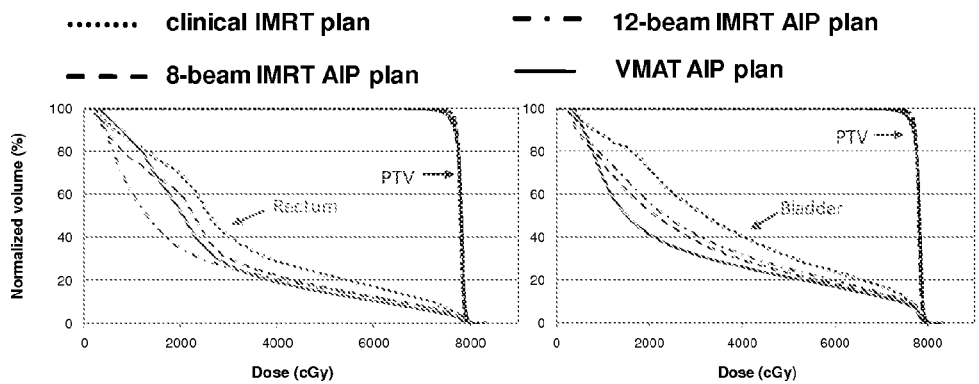
FIG. 24 shows Dose-Volume Histograms of the PTV, rectum, and the bladder from the clinical plan, 8-beam IMRT plan, 12-beam IMRT plan and the VMAT plan for one of the patients (patient 1). For this patient, 12-beam IMRT autoplan has reached similar rectum sparing to the VMAT autoplan.
Figure 25:
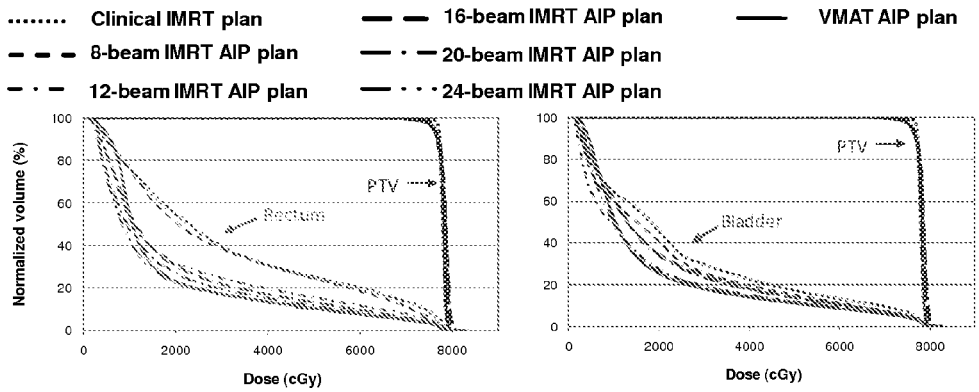
FIG. 25 Dose-Volume Histograms of the PTV, rectum, and the bladder from the clinical plan, 8-beam IMRT plan, 12-beam IMRT plan, 16-beam IMRT plan, 20-beam IMRT plan, 24-beam IMRT plan, and the VMAT plan for one of the patients (patient 2). For this patient, 24-beam IMRT autoplan has reached similar rectum sparing to the VMAT autoplan.

FIGS. 24 and 25 compare the dose-volume-histograms (DVHs) of each type of plans for two patients who require different numbers of beams in IMRT to reach similar quality of VMAT plan. For both patients, VMAT plans show significant reduction in rectum dose compared to clinical and autoplan-based 8-beam IMRT. As the number of beams used in IMRT plans increases, however, the rectum dose reduces dramatically and approaches the dose level of the VMAT plan, while keeping the PTV coverage at the same level. For patient 1 and patient 2, 12-beam IMRT plan and 24-beam IMRT has respectively produced lower rectum dose than the VMAT plan.

Figure 26:
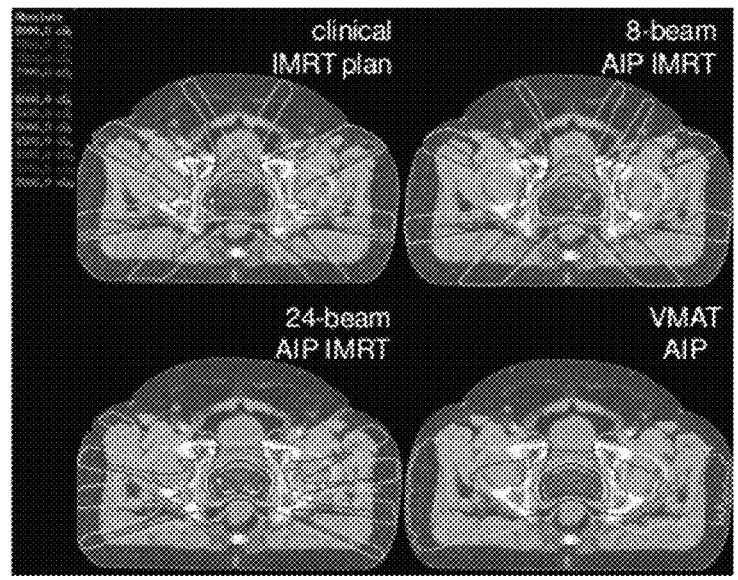
FIG. 26 shows dose distributions represented by iso-dose lines from the clinical plan, 8- and 24-beam IMRT autoplans, and the VMAT autoplan for patient 2. Purple: PTV; green: rectum; pink: femoral heads.

FIG. 26 shows the iso-dose distributions from the clinical plan, 8- and 24-beam autoplan-based IMRT plans, and the autoplan-based VMAT plan for patient 2. autoplan-based plans, especially the VMAT plan, have not only improved the dose sparing in the rectum and the bladder, but also greatly reduced the amount of hot spots near the body surface and reduced dose spreading out to normal tissue. Although the autoplan-based plans show higher dose in the femoral heads region than the clinical plan, they have all well satisfied the standard dose criteria for femoral heads.

Figure 27:
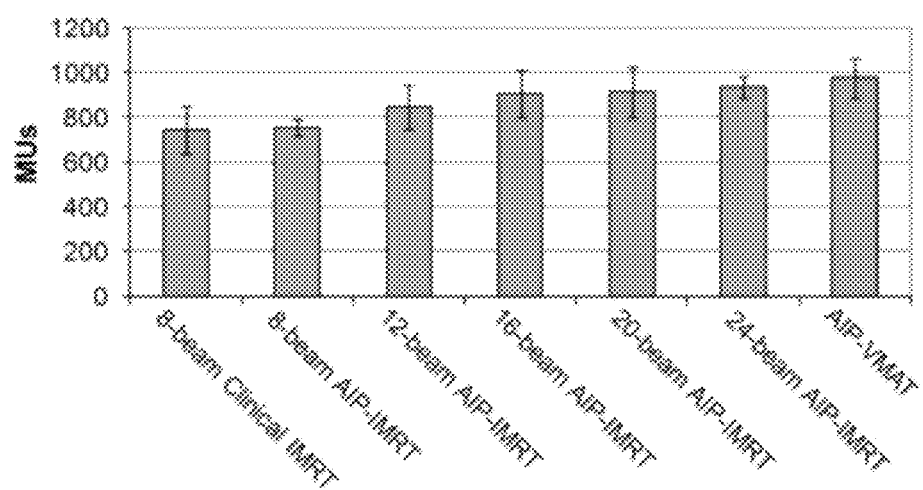
FIG. 27 shows the average total MUs of the eleven patients from the each type of plans. The total MU increases significantly with the number of beams used in IMRT. The VMAT plan used about 30% higher MUs than the clinic plan and the 8-beam IMRT plan, respectively, but comparable amount of MUs to the 24-beam IMRT plan.

Comparing the total MUs used in each type of plan, the total MU increases significantly with the number of beams used in IMRT; the VMAT plan resulted in about 30% higher MUs than the clinic plan and the 8-beam autoplan-based IMRT plan, respectively, but only slightly higher MUs than the 24-beam IMRT plan, as shown in FIG. 27.

In this example, all the autoplan-based IMRT plans have used re-selected beam angles instead of the standard 8-beam template of an institution. The principle of the angle-selection is to choose more beams that are parallel to the tangent direction of the intersection between the prostate and the rectum so that they could produce the best dose drop-off at the connection. It may be that the greatly improved dose distribution and the rectum dose sparing in AIP-based IMRT plans are partly resulted from the proper selection of beam angles. However, it was also observed that, as the number of beams increases, selection of beam angles gradually loses its impact on the plan quality.

Figure 28:
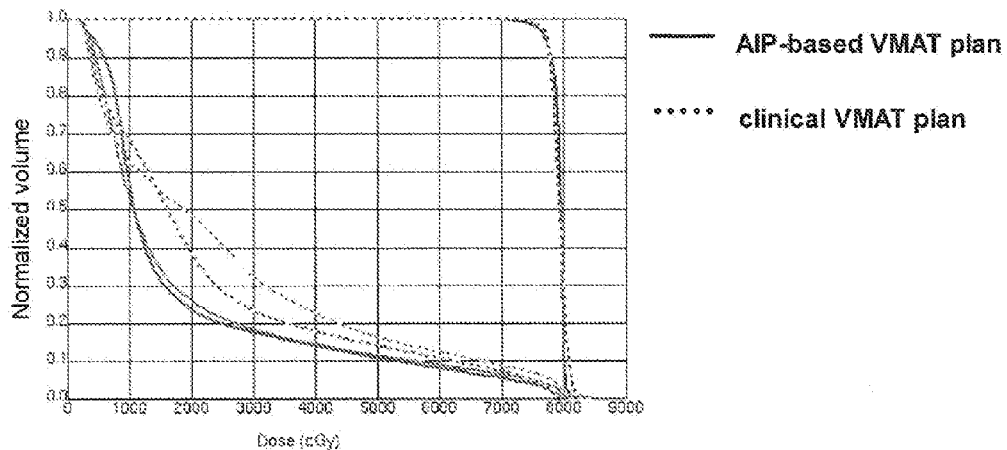
FIG. 28 shows DVHs of the clinical and the VMAT autoplans. Green: rectum; brown: bladder; blue: PTV. The VMAT autoplan shows slightly more homogeneous PTV coverage, and much better dose sparing in the rectum and the bladder than the clinical VMAT plan.

As shown above, autoplan-based VMAT plans show obvious advantage over the clinical IMRT plans, which not only reveals immense potential of the VMAT technique, but also suggests the effectiveness of the autoplan algorithm for treatment planning. Due to the limited number of clinical VMAT plans designed by the dosimetrists, the comparison between the clinical and the autoplan-based VMAT plans were not included. However, for the only two prostate patients who have available clinical VMAT plans, the autoplan-based VMAT plans produced at least comparable plan qualities to the clinical VMAT plans. The DVHs of one of the patients are shown in FIG. 28.

This demonstrates that the VMAT technique combined with the autoplan algorithm generates significantly superior plans than the clinical IMRT plans for prostate cancer treatment. However, fixed-beam IMRT using autoplan algorithm is capable of exceeding the performance of VMAT if the number of beams used in the plan is high enough. IMRT plan quality consistently improves as the number of beams increases; to a certain point, IMRT surpasses VMAT and the turning point varies largely among different patients, which ranges from 12 to 24 beams for the set of patients involved in this example. Expectedly, when even higher number of beams is applied in IMRT, more superior plans could be achieved, however, at the cost of even longer dose delivery time and total treatment time as well as even higher economic expense. Considering the superior delivery efficiency of VMAT and the fact that the current plan quality of VMAT in both DVH and conformality of dose distribution have both well exceeded clinical plans, VMAT may still be the preferable choice in treating prostate cancer.

Example 3

AutoPlan for Use in Generating Treatment Plans for Head and Neck Tumors

The AutoPlan algorithm for head-and-neck cancer follows a similar approach to that of prostate cancer. First, the algorithm automatically generates planning ROI structures based on physician-drawn contours; the newly generated structures involve modifications and additions to the original contours in order to improve the planning quality and efficiency. Radiation beams with pre-selected angles are then automatically configured and the inverse planning objectives with pre-defined parameters are loaded into the Pinnacle3 planning system. Optimization of the objectives is executed for the first round and then the PTV objective functions are evaluated. If all the PTV objectives are all well satisfied, increase the OAR objective weight or lower the OAR objective dose and continue optimization without resetting the beams; repeat this process until one or more PTV objectives are not well satisfied. In the last step, remove hot/cold spots in the normal tissue/PTV—hot/cold spot ROIs are generated from iso-dose structures and objectives for limiting the dose levels in the hot/cold spot ROIs are added to the objective list. The plan is then re-optimized without resetting the beams. The hot/cold spot removal process is repeated for a few iterations, which leads to the final plan.

Figure 29:
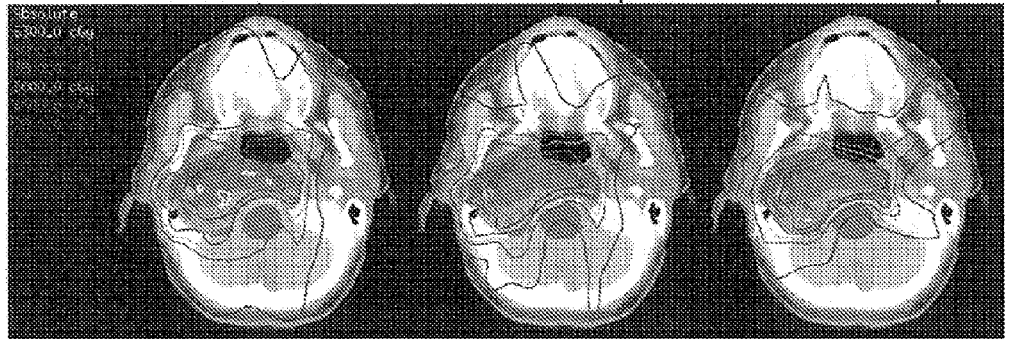
FIG. 29 illustrates dose distributions represented by iso-dose lines from the clinical plan and the 9 and 15 beam autoplan for a head and neck patient.
Figure 30:
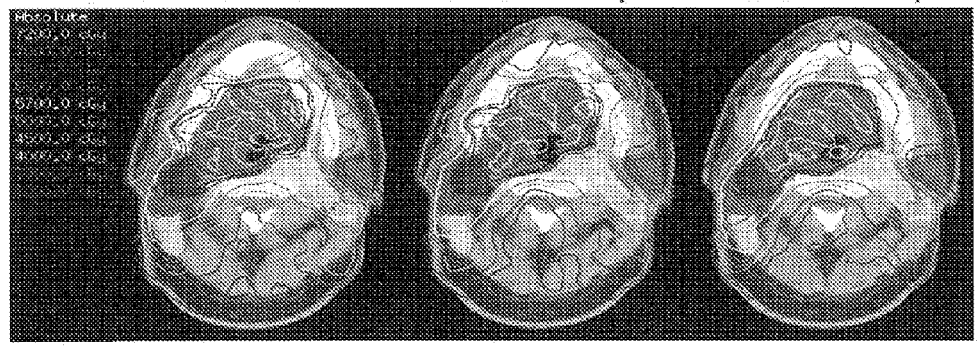
FIG. 30 illustrates dose distributions represented by iso-dose lines from the clinical plan, and the 9 and 15 beam autoplan for a head and neck patient.

FIGS. 29 and 30 show clinical and autoplan dose distributions for two head and neck patients.

Example 4

AutoPlan for Use in Generating VMAT Treatment Plans for Lung Tumors

FIGS. 31(a) and (b) show fixed beam IMRT clinical plan, and autoplan-based VMAT plans dose distributions for a lung cancer patients. FIG. 31(c) displays the DVH comparisons between fixed beam clinical IMRT plan (solid line) and autoplan-based VMAT plans (dashed line). Since autoplan-based VMAT plan essentially achieved similar plan quality to that of fixed beam IMRT plan, this example is a demonstration that autoplan algorithm is now readily to be used in VMAT radiotherapy.

Example 5

AutoPlan for Use in Generating VMAT SBRT Plans for Lung Tumors

FIGS. 32(a) and (b) show an autoplan-based VMAT SBRT plan, a fixed beam SBRT clinical plan, and dose distributions for a stage I lung cancer patients. FIG. 32(c) are DVH comparisons between fixed beam clinical SBRT plan (solid line) and autoplan-based VMAT SBRT (dashed line). Since the autoplan-based VMAT SBRT plan essentially achieved better plan quality to that of fixed beam SBRT plan, this example demonstrates that AutoPlan may be used in SBRT.

Example 6

AutoPlan for Use in Generating ART Plans for Prostate Tumors

A prostate cancer patient enrolled in an institutional review board (IRB) approved protocol was selected to evaluate the potential benefit of automated adaptive planning. 9 CT datasets (one from simulation and eight from daily treatment CT) were acquired in 2.5-mm slices using a multiple CT scanner.

The isocenter re-positioning method which is the current adaptive imaged radiotherapy (IGRT) was used to compare the benefit of AutoPlan AAP method. For isocenter re-positioning method, The planning target volume (PTV) was generated by expanded 5 mm for prostate and seminal vesicle (SV). The IMRT with a standard 8-Beams and Smart-Arc plans were designed by AutoPlan on research Pinnacle (8.1 y) to achieve the coverage of 95% prescription (i.e. 76 Gy) for PTV and minimize the doses to rectum, bladder and femoral heads. For each daily CT, the plans was recalculated using a new isocenter which was determined by the rigid image registration between planning CT and daily CT. The plans recalculated by the isocenter shift are referred to as the Rp-iso plans.

For AAP method, the PTV in daily CT was defined as the 3 mm expansion of propagated prostate and SV. A new inverse IMRT and a new SmartArc plan were generated by AutoPlan using the new PTV and propagated contours of rectum, bladder and femoral heads. The ART plans generated by AutoPlan are referred to as Adaptplans.

The final treatment plan evaluation was based on physician-drawn contours on simulation CT and each daily CT. The cumulative dose-volume-histograms (DVHs) of the target and the normal tissues were acquired by averaging the DVHs based on the physician-drawn contours of each daily CT and compared to those of the initial plans recalculated just by shifting the isocenter.

Figure 33:
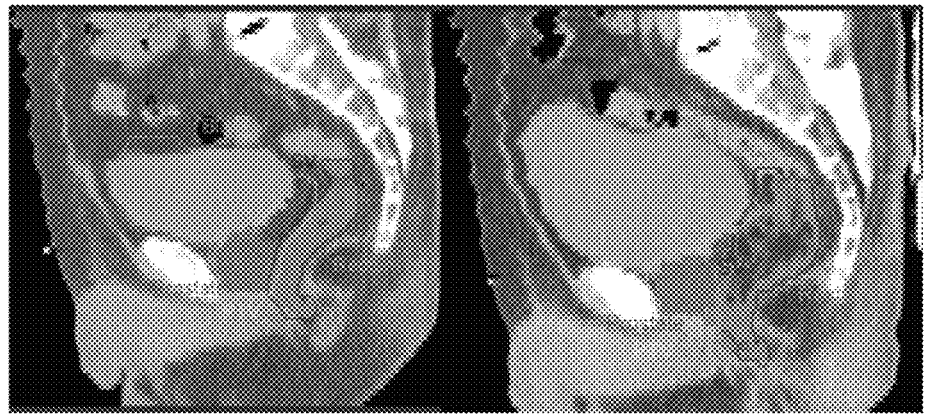
FIG. 33 shows a comparison between automatically generated contours (denoted by lines) for treatment plan and physician drawn contours (color wash) of anatomic change during daily treatments in two different scenarios: (a) without gas bubbles and (b) with gas bubbles in rectum.

FIG. 33 displays the comparison between automatically generated contours (denoted by lines) for treatment plan and physician drawn contours (color wash) of anatomic change during daily treatments in two different scenarios: (a) without gas bubbles and (b) with gas bubbles in rectum. For scenario a) and b), the contours were generated by, respectively, Demons deformable image registration (DIR) algorithm and DIR plus post contour adaption closely match with those drawn by the physicians. It should also be noticed that automatically generated contours were not perfect. However, the replan PTV generated by 3 mm expansion of propagated prostate and SV enclosed the physician drawn prostate and SV in both scenarios. The most errors caused by automatically generated rectum and bladder were outside the target region.

Figure 34:
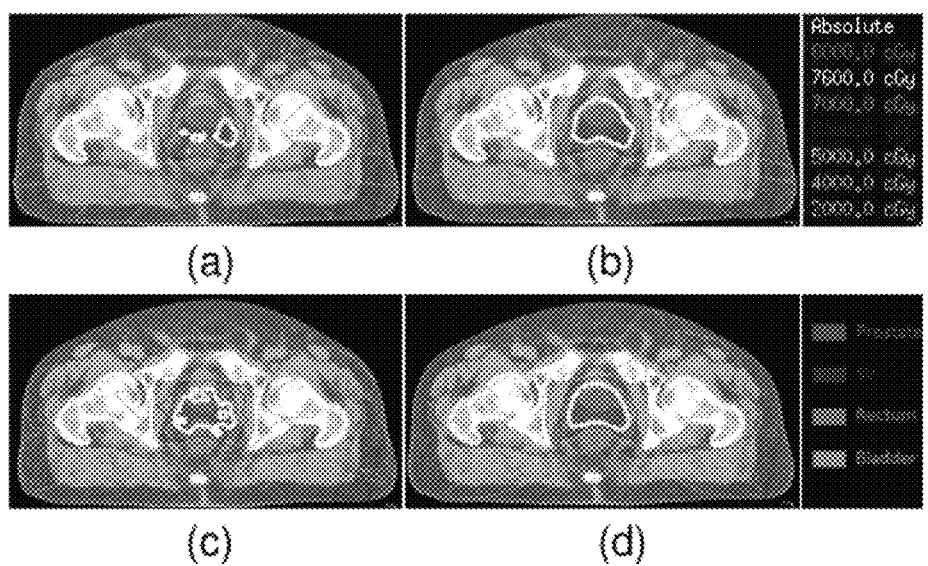
FIG. 34 shows a comparison of iso-dose distributions of the adaptive plan (Adaptplan) using AutoPlan and iso-shift plan (Rp-iso plan) for both fixed beam IMRT technique (a and b) and VMAT technique (c and d) on a daily CT: a) Rp-iso IMRT plan, (b) IMRT adaptive plan, (c) Rp-iso Arc plan and (d) Arc adaptive plan on a daily CT. The contours shown on this CT were drawn by physician.
Figure 35:
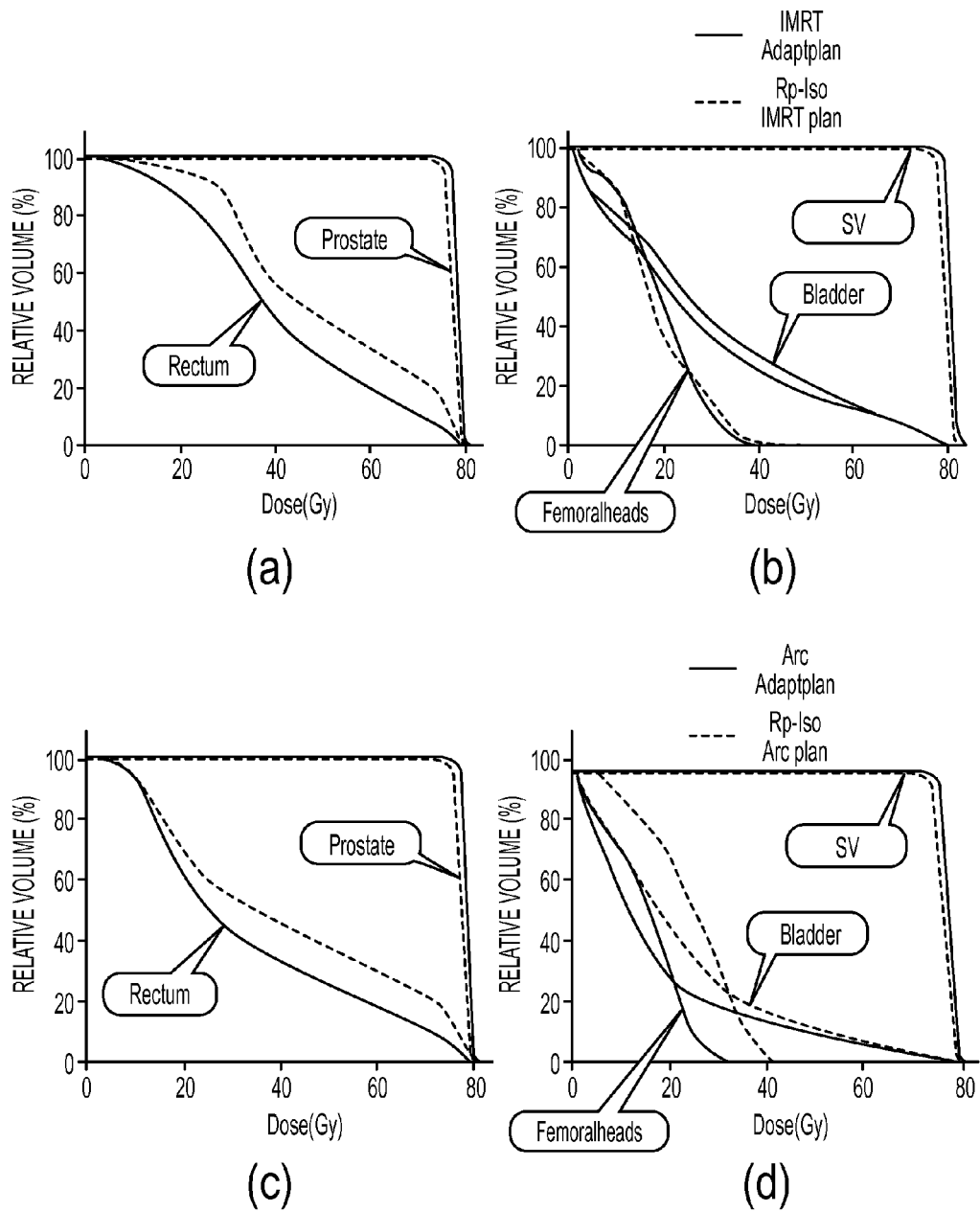
FIG. 35 shows a comparison of DVHs of the adaptive plan (Adaptplan) using AutoPlan adaptive planning and iso-shift plan (Rp-iso plan) for both fixed beam IMRT technique (a and b) and SmartArc technique (c and d).

FIGS. 34 and 35 demonstrate the degree of improvement by the AAP method compared to isocenter re-positioning method. FIG. 34 displayed the comparison of iso-dose distributions of the adaptive plan (Adaptplan) using the AAP method and iso-shift plan (Rp-iso plan) for both fixed beam IMRT technique (a and b) and VMAT technique (c and d) on a daily CT. It can be seen the under dosing during the fractional treatment to the target (shown in FIGS. 34(a) and (c)) was corrected by the AAP method. FIG. 35 illustrates the comparison of DVHs of the adaptive plan (Adaptplan) using the AAP method and iso-shift plan (Rp-iso plan) for both fixed beam IMRT technique (a and b) and VMAT technique (c and d). Each of the DVHs shown is the average of 8 DVHs calculated based on physician drawn contours on 8 daily CTs. Cumulative DVHs comparisons between the adaptive IMRT plan (IMRT Adaptplan) and the Rp-iso IMRT plan (a, b) and between the adaptive Arc plan (Arc Adaptplan) and the Rp-iso Arc plan (c, d). The under dose of prostate and SV and overdose of rectum by the commonly used iso-shift method were clearly indicated by DVHs denoted by the dashed lines. Using the AAP method, the deficit of under dose of target and overdose of rectum were corrected. The sparing of bladder in Rp-iso plan for Arc Plan was better than that in Adaptplan. The reason is that large anatomical change (bladder filling) during daily treatment caused SV close to rectum and far away to bladder. Thus, the iso-shift method spared more bladder with a cost of under dosing SV.

In particular, the percentage volume covered by prescription dose for prostate and SV reached 98.8% and 96.7% for IMRT, and 97.2% and 95.5% for VMAT, which was an absolute increase of respectively 10.8% and 15.3% for IMRT, and 5.4% and 10.9% for VMAT plan compared to shifting-iso method. The V70 and mean dose for rectum were 10.7% and 40.5 Gy for IMRT, and 10.3% and 33.3 Gy for VMAT plan, an absolute reduction of 10.3% and 8.5 Gy for IMRT, and 10.8% and 6.8 Gy for VMAT, compared to shifting-iso method.

Example 7

AutoPlan for Use in Generating ARC Plans for Prostate Tumors

Eleven patients with prostate cancer previously treated were randomly selected for this example. For each patient, a VMAT plan and a series of IMRT plans using an increasing number of beams (8, 12, 16, 20, and 24 beams) were examined. All plans were generated using an in-house-developed automatic inverse planning (AIP) algorithm. An existing 8-beam clinical IMRT plan, which was used to treat the patient, was used as the reference plan. For each patient, all AIP-generated plans were optimized to achieve the same level of planning target volume (PTV) coverage as the reference plan. Plan quality was evaluated by measuring mean dose to and dose-volume statistics of the organs-at-risk, especially the rectum, from each type of plan.

For the same PTV coverage, the AIP-generated VMAT plans had significantly better plan quality in terms of rectum sparing than the 8-beam clinical and AIP-generated IMRT plans ($p<0.0001$). However, the differences between the IMRT and VMAT plans in all the dosimetric indices decreased as the number of beams used in IMRT increased. IMRT plan quality was similar or superior to that of VMAT when the number of beams in IMRT was increased to a certain number, which ranged from 12 to 24 for the set of patients studied. The superior VMAT plan quality resulted in approximately 30% more monitor units than the 8-beam IMRT plans, but the delivery time was still less than 3 minutes.

Considering the superior plan quality as well as the delivery efficiency of VMAT compared with that of IMRT, VMAT may be the preferred modality for treating prostate cancer.

Example 8

Patients

Computed tomography data sets of 11 patients with prostate cancer who were treated with IMRT between 2009 and 2010 were randomly selected for this institutional review board approved study. The planning target volume (PTV) was defined as the prostate and the proximal seminal vesicles (n=8), or the prostate and the entire seminal vesicle (n=3) with a margin of 5 mm posterior and 7 mm in other directions. For all patients, the prescribed dose was 76 Gy delivered in 38 fractions. The rectum tolerance is 70 Gy covering less than 25% of the volume, the 90% isodose line falls within the half width of rectum, and the 50% isodose line falls within the full width of the rectum. For the bladder, 65 Gy and 40 Gy have to cover less than 25% and 50% of the volume, respectively. The femoral heads are limited to receive 50 Gy in less than 10% of the volume (24).

Automatic Inverse Planning (AIP) Algorithm

To generate VMAT and IMRT plans for each patient, the AIP algorithm which was implemented in the Pinnacle[3] v9.0 treatment planning system was used (Philips Nuclear Medicine, Fitchburg, Wis.) (25, 26). The AIP algorithm makes use of Pinnacle's scripting language. It efficiently and automatically generates IMRT or VMAT plans by performing the following steps.

1. Planning structure generations. A set of planning structures is generated based on the physician-drawn PTV, OARs and normal tissue in order to facilitate the inverse planning. A brief description to each structure is listed in Table 5. In addition to the basic structures, AIP creates two ring structures, FS-PTVRing and FS-Ring, which help to shape the isodose distribution and to reduce the appearance of hot spots in the corresponding areas.

TABLE 5

| | |
|---|---|
| FS-PTV | A copy of the physician-draw PTV structure |
| FS-PTVRing | 8 mm thick ring structure surrounding 2 mm expansion of the PTV |
| FS-Ring | 3 cm thick ring structure along the outer contour of the body |
| FS-NormalTissue | Entire body excluding the 10 mm expansion of the PTV |
| FS-BladderAvoid | The bladder structure avoiding 3 mm expansion of the PTV |
| FS-RectumAvoid | The rectum structure avoiding 3 mm expansion of the PTV |
| FS-FHAvoid | The femoral heads structure avoiding 3 mm expansion of the PTV |

2. Initial objective function setup. An initial set of objective functions, which applies to all prostate IMRT/VMAT patients, were determined based on previous experience in prostate treatment planning and serves as the starting point of the optimization in AIP. The initial set of objective functions, as shown in table 6, gives tight dose constraints to the OARs and normal tissue but loose constraints to the PTV such that the initial optimization results in a plan with the best OAR sparing.

TABLE 6

| ROI | Type | Con-strain | Target cGy | Volume (%) | Weight | a |
|---|---|---|---|---|---|---|
| FS-PTV | Uniform Dose | N | 7900 | | 0.01 | |
| FS-PTV | Max Dose | N | 7900 | | 0.01 | |
| FS-PTV | Min Dose | N | 7900 | | 0.01 | |
| FS-PTVRing | Max Dose | N | 7000 | | 0.005 | |
| FS-Ring | Max DVH | N | 4000 | 0 | 0.002 | |
| FS-NormalTissue | Max DVH | N | 4000 | 0 | 0.01 | |
| FS-BladderAvoid | Max EUD | N | 1600 | | 0.01 | 2 |
| FS-RectumAvoid | Max EUD | N | 1600 | | 0.01 | 5 |
| FS-FHAvoid | Max EUD | N | 3500 | | 0.01 | 50 |

Figure 36:
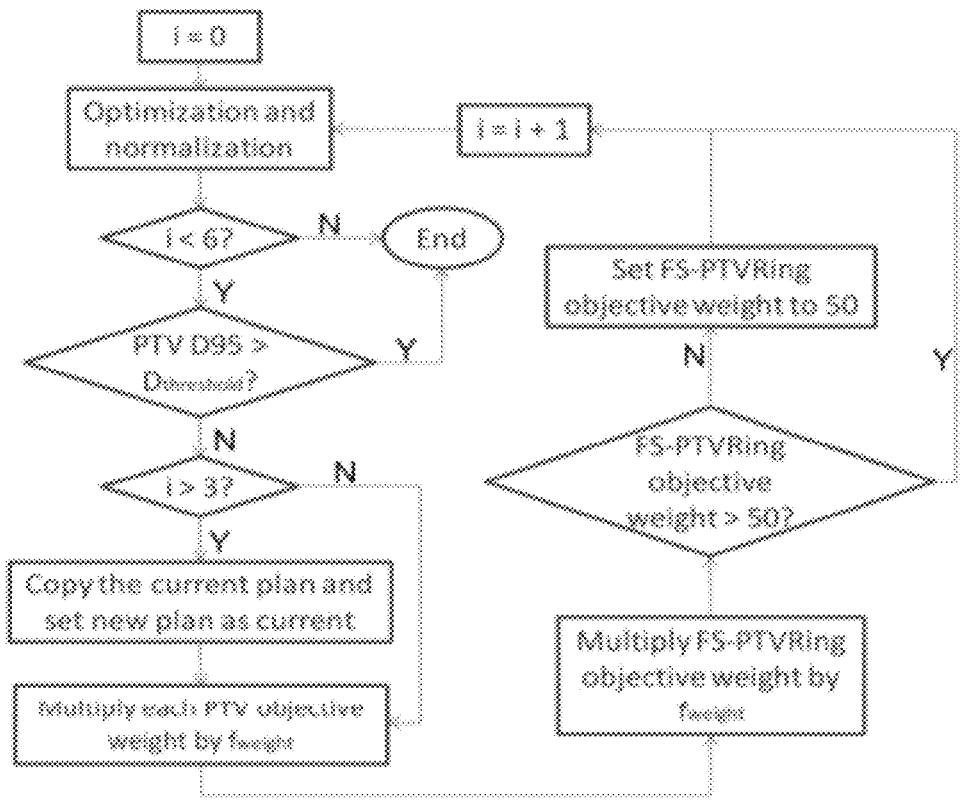
FIG. 36 is a flowchart of the OFPA algorithm for prostate IMRT and VMAT, where i is the index of the optimization cycle, which has an upper limit of 6. Dthreshold and fweight are arbitrarily chosen to be 76.4 Gy and 5, respectively, based on experience.
Figure 37:
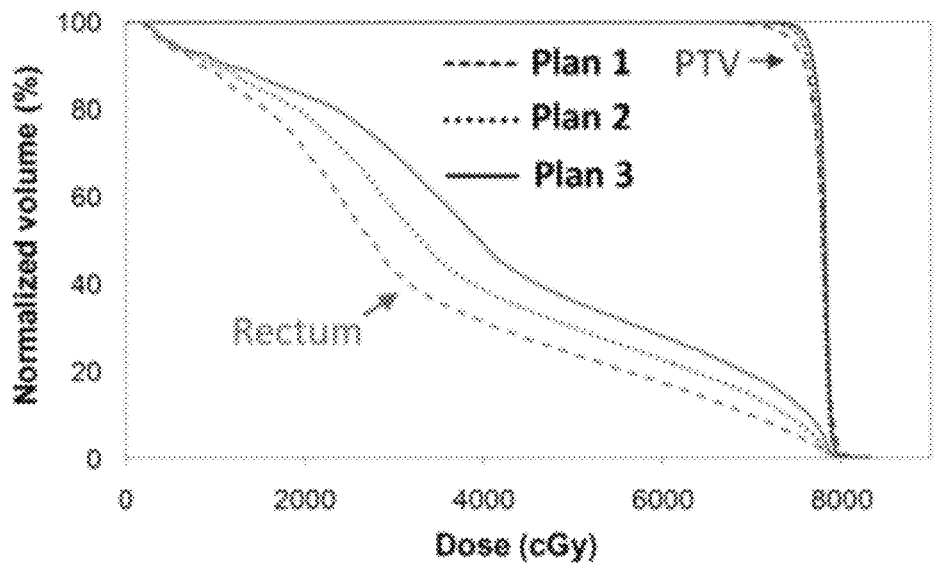
FIG. 37 is dose-volume histograms of three plans resulted from one AIP execution with different trade-offs between PTV coverage and rectum sparing.

3. Objective function parameter optimization (OFPO). The flowchart of the OFPO process is shown in FIG. 36. Three to six rounds of optimizations were applied for each patient, depending on the PTV coverage resulted from each round of optimization. Once the PTV D95 exceeded a pre-defined threshold (Dthreshold), OFPO terminated. In each round of optimization after the initial one, the weights of the PTV objectives were increased and optimization was continued. Hence, a plan with improved PTV coverage and therefore reduced OAR sparing resulted. Beyond 3 rounds of optimizations, a copy of each resulted plan was saved and, finally, 1 to 4 plans resulted, each with a different PTV/OAR compromise. An example is shown in FIG. 37. The physician can choose the most preferable plan from them.

Note that the AIP program is not a treatment planning system but rather an inverse planning technique built in conjunction with the Pinnacle³ treatment planning system. The MP program utilizes Pinnacle³'s built-in functions, which include its dose calculation and optimization plug-ins. In this example, all AIP-generated VMAT plans were optimized using the SmartArc module in Pinnacle³, which uses an optimization algorithm described by Bzdusek et al. (27). All AIP-generated IMRT plans in this example were optimized with the direct machine parameter optimization (DMPO) module (28), which directly optimizes MLC leaf positions and segment weights so that there is no need for fluence conversion and the plan quality will not degrade during delivery. When the same beam configuration is used, the AIP algorithm has been shown to consistently generate plans that are superior or comparable to those developed manually by experienced dosimetrists (25, 26).

Planning Study Design

For each patient, the clinically utilized IMRT plan, which was generated by an experienced dosimetrist prior to this example, was used as the reference plan. These plans utilized an 8-beam configuration, standard for prostate cancer treatment.

In this example, a VMAT plan was generated using the AIP algorithm for each patient. The AIP-generated VMAT plans used two 360° arcs (one rotating clockwise and the other rotating counter-clockwise), which produces better plan quality than using a single 360° arc. A comparison between using 1 and 2 arcs can be found in the Discussions section. A total of 91 control points were created through each arc using 4° spacing, which is Pinnacle's default value and exhibited good dose calculation accuracy (29). It was found that a denser spacing of 2° is not necessary because it brings little improvement in plan quality but much prolonged optimization time. All VMAT plans were generated with variable dose rate as well as variable gantry rotation speed.

Also, a series of IMRT plans was generated using 8, 12, 16, 20, and 24 beam angles with the AIP algorithm for each patient. The 8-beam configuration is used in MDACC's standard template. For the 12-, 16-, 20-, and 24-beam IMRT configurations, beam angles were more densely selected near the tangent direction along the intersection between the rectum and the PTV and sparsely selected at other directions. Such a beam angle distribution produces a sharp dose fall-off at the rectum. Selected beam angles varied among patients, but most of the beams angles were the same. For the 24-beam IMRT plans, however, uniformly distributed beam angles were found to yield a better plan quality than beam angles selected using the approach mentioned above. Therefore, a uniform beam angle distribution was used for the 24-beam IMRT plans. In this example, an AIP-generated plan with a higher number of beams was not simply calculated from the same set of objectives as the other plans nor was it built upon the plan with a lower number of beams. Instead, the AIP algorithm was executed independently for each beam configuration, which resulted in a different set of objective parameters. Of the generated IMRT plans with different PTV/OAR compromises after each AIP execution, the IMRT plan was selected that had the same level of PTV coverage as the clinical IMRT plan to directly compare OAR sparing among the plans.

More details on the inverse planning parameter settings for IMRT and VMAT are listed in table 6. The maximum number of segments for IMRT and the maximum delivery time in seconds for VMAT were both set to 100 because further increasing the limits does not help to improve the plan quality. All IMRT plans in this example used the step-and-shoot technique and all plans deliver 6-MV photons.

TABLE 7

| | |
|---|---|
| minimum segment area (cm²) | 2 |
| minimum segment Mus | 1 |
| minimum number of leaf pairs | 2 |
| minimum leaf end separation (cm) | 1.5 |
| maximum number of iterations | 25 |
| convolution dose iteration | 5 |
| maximum number of segments (IMRT) | 100 |
| maximum delivery time (second) (VMAT) | 100 |
| dose engine | CC Convolution |

PTV coverage was evaluated using the conformality index (CI) and the heterogeneity index (HI), which were calculated as follows (30):

$$CI = \frac{TV_{D_P}}{TV} \times \frac{TV_{D_P}}{V_{D_P}} \in [0, 1],$$

Where $TV_{D_P}$ is the target volume covered by the prescribed dose, TV is the target volume, and $V_{D_P}$ is the volume enclosed by the prescribed isodose surface and $$HI = \frac{D_1}{D_{95}},$$

where $D_1$ and $D_{95}$ are, respectively, the dose encompassing 1% and 95% of the target volume.

The IMRT and VMAT plans were evaluated using dose-volume histograms (DVHs). To quantitatively measure the OAR sparing of each plan, the mean OAR volume was calculated within the 30-, 40-, 50-, 60-, and 70-Gy isodose lines and the average mean dose to the rectum and the bladder. The total MUs per fraction were also compared to assess the delivery time for each plan. Statistical analysis was performed using the two-sided paired t-test. A p-value<=0.05 was defined as statistically significant.

Example 9

All of the AIP-generated IMRT and VMAT plans were reviewed by a radiation oncologist and were considered as acceptable for patient treatment. All the AIP-generated plans in this example achieved a similar level of PTV coverage as the 8 beam clinical IMRT plans previously generated by experienced dosimetrists. The average CI and HI values for the 11 patients for each category of plans are similar, as shown in FIG. 20.

The number of patients whose IMRT plan in each category achieved better rectum sparing than their VMAT plan were summarized. As shown in FIG. 23, no patients received better rectum sparing from their 8-beam clinical or AIP-generated IMRT plans than from their VMAT plans. For one patient, the 12-beam IMRT plan achieved better rectum sparing (14% lower mean rectal dose, 15% less volume receiving 0-30 Gy dose and only 1% larger volume receiving 40-70 Gy dose) than the VMAT plan. The number of patients keeps increasing with the number of beams in the IMRT plans. All patients received better rectum sparing from their 24-beam IMRT plan than from their VMAT plan.

Figure 38:
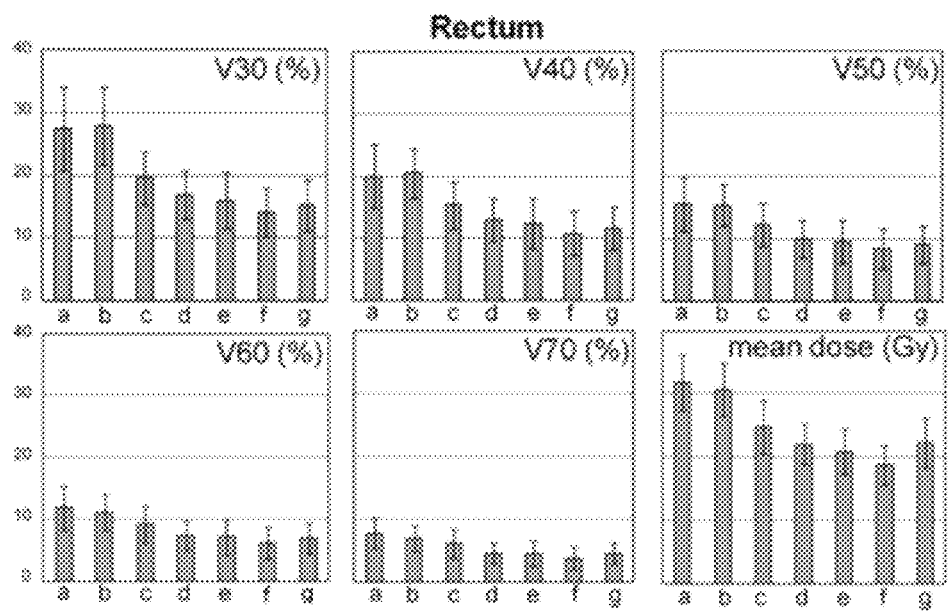
FIG. 38a-g are dose statistics in the rectum for the 11 patients from the 8-beam clinical IMRT plan (a), 8-(b), 12-(c), 16-(d), 20-(e) and 24-beam (f) AIP-generated IMRT plans, and the AIP-generated VMAT plan (g).
Figure 39:
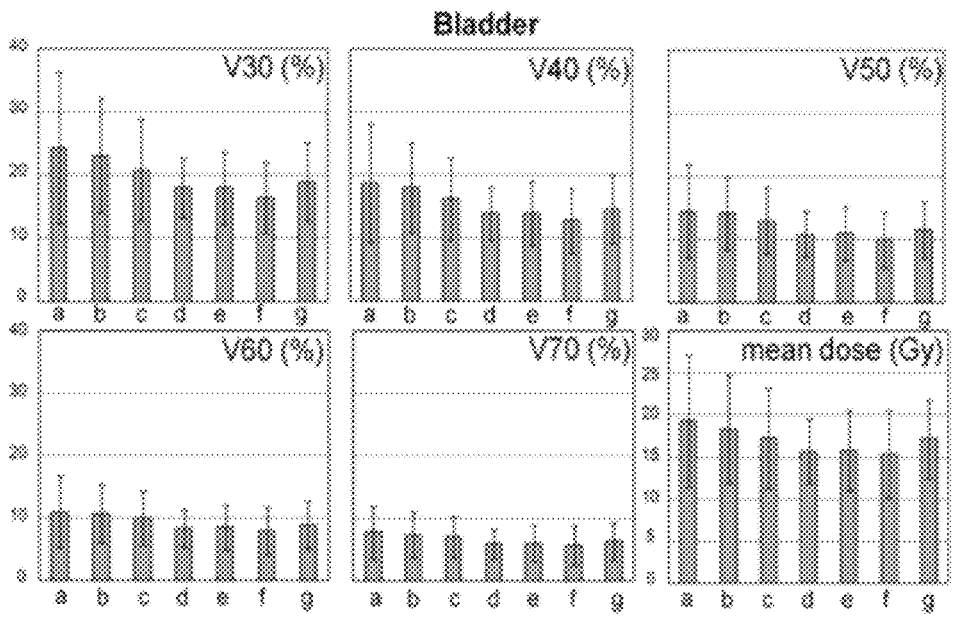
FIG. 39a-g are dose statistics in the bladder for the 11 patients from the 8-beam clinical IMRT plan (a), 8-(b), 12-(c), 16-(d), 20-(e) and 24-beam (f) AIP-generated IMRT plans, and the AIP-generated VMAT plan (g).
Figure 44:
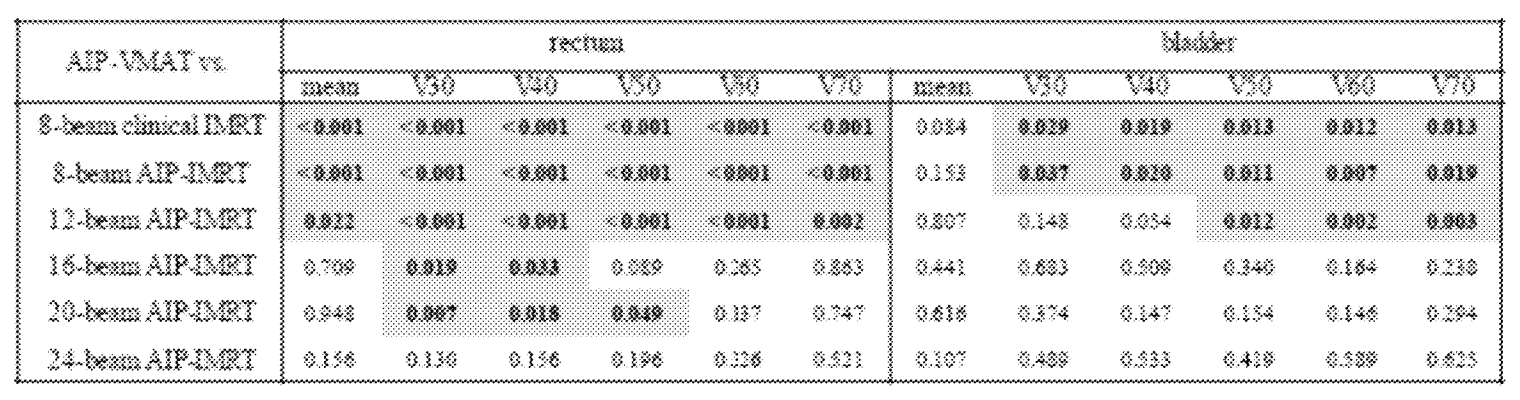

FIG. 38 and FIG. 39 depict quantitative dose-volume measures in the rectum and bladder from the IMRT and VMAT plans that had a similar level of PTV coverage. In general, the 8-beam AIP-generated IMRT plans had similar rectum and bladder sparing to the 8-beam clinical IMRT plans but inferior to that of the AIP-generated VMAT plans. As the number of beams used in IMRT increased, the level of rectum sparing achieved by these plans improved, eventually reaching a level similar to that of the VMAT plans. FIG. 44 shows the p values for the differences between doses delivered by the VMAT plans and those delivered by the various IMRT plans. For all the dosimetric indices in the rectum, the VMAT plans had a highly significant advantage (p<0.0001) over the 8-beam clinical and AIP-generated IMRT plans. However, as more beams were included in the IMRT plans, the dosimetric advantage of the VMAT plans became less significant because the IMRT plan qualities were improved. For all the dosimetric indices in the bladder, the VMAT plans and the AIP-generated 8-beam IMRT plans were, on average, better or at least no worse than the 8-beam clinical IMRT plans. Although the trend for each individual patient Was not as clear as in the rectum, dose levels in the bladder were well within the standard dose constraints (24) in all plans generated in this example.

Figure 40:
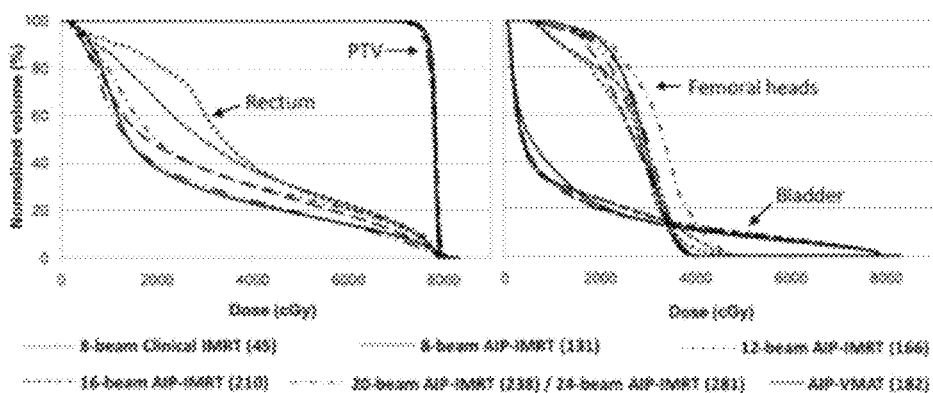
FIG. 40 is dose-volume histograms of the PTV, rectum, and bladder from DART plans with different numbers of beams and the AIP-generated VMAT plan for a typical patient. The numbers in parentheses in the legend give the total number of control points for each plan.

FIG. 40 shows the DVHs of a typical patient. The PTV received similar coverage from each type of plan. The rectum received a much lower dose from the VMAT plan than from the 8-beam IMRT plans. However, as the number of beams in IMRT increases, the rectum dose from the IMRT plan decreases. In the 20-beam AIP-generated IMRT plan, the rectum DVH was only slightly higher than that of the VMAT plan in the mid-dose region, but it was superior to that of the VMAT plan in both the low- and high-dose regions. The 24-beam AIP-generated IMRT plan was almost identical to the 20-beam AIP-generated IMRT plan.

For the patient presented in FIG. 40, note the change in the total number of control points of each plan. In the case of the 16-beam AIP-generated IMRT plan, the total number of control points was 210 (9-19 control points from each beam direction), which was 15% higher than that of the VMAT plan (182), but the level of rectum sparing from this IMRT plan did not reach the same level as that from the VMAT plan. In the case of the 20-beam AIP-generated IMRT plan, the total number of control points was 238 (7-19 control points from each beam direction), which compensated for the missing beam angles and resulted in the same level of rectum sparing as the VMAT plan.

Figure 41:
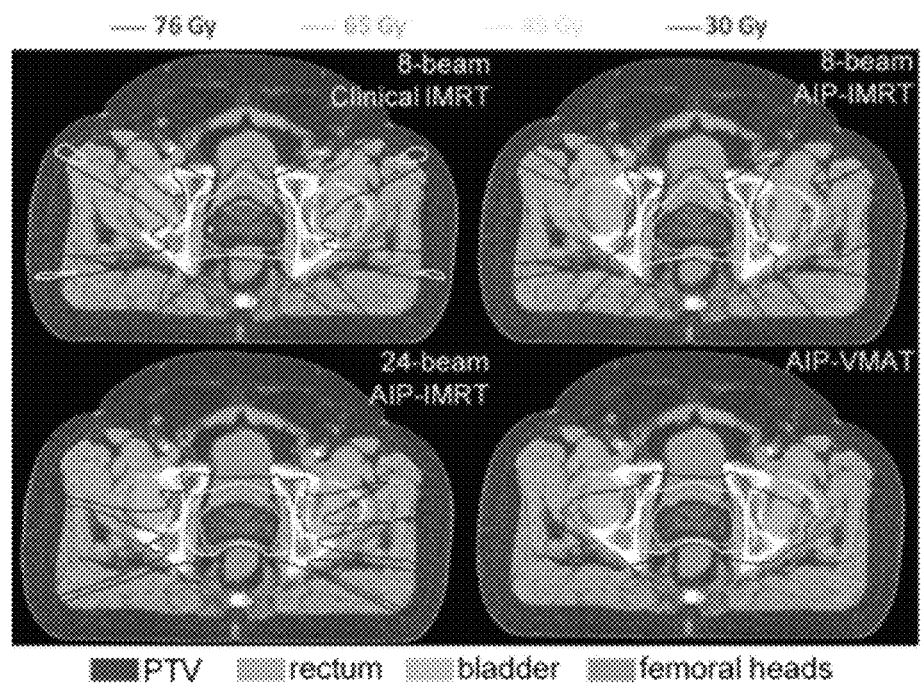
FIG. 41 is dose distributions represented by isodose lines from the 8-beam clinical and AIP-generated IMRT plans, the 24-beam AIP-generated IMRT plan, and the AIP-generated VMAT plan.
Figure 42:
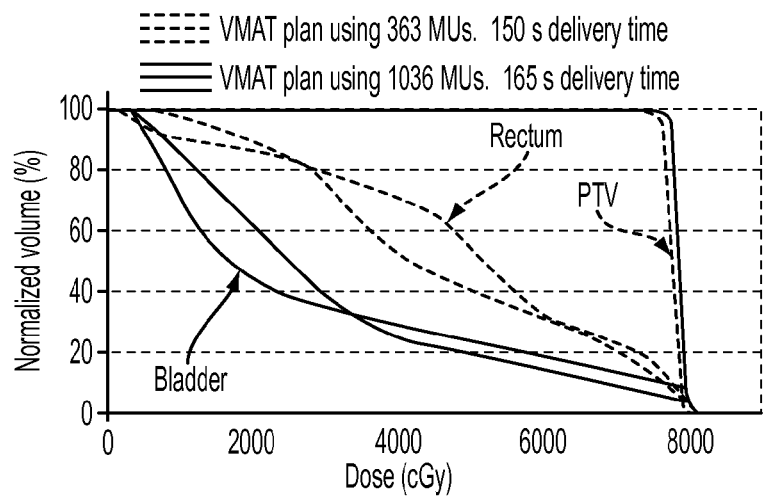
FIG. 42 is DVH curves from two VMAT plans with different MUs.

FIG. 41 shows the isodose distributions from the different types of plans for a typical patient whose IMRT plan required 24 beams to be comparable to the VMAT plan in terms of rectum sparing. Although the 24-beam IMRT and the VMAT plans delivered a higher dose to the femoral heads than the 8-beam clinical IMRT plan, they are both well within the standard dose constraints for femoral heads (V50 less than 10% (24)).

The comparison of the total MUs used in each plan showed that the average total MU usage increased significantly as the number of beams used in IMRT increased. The AIP-generated VMAT plans used about 30% more total MUs than the 8-beam clinical and AIP-generated IMRT plans, but only about 4% more total MUs than the 24-beam AIP-generated IMRT plans (FIG. 9). The delivery time for a typical VMAT plan was 2.6 minutes; the delivery times for 8-, 12-, 16-, 20-, and 24-beam IMRT plans were respectively 4.7, 7, 9.3, 11.7, and 14 minutes, which included the beam-on time and loading time of each beam.

In this example, quality of VMAT plans was compared to a series of IMRT plans using increasing numbers of beams. IT is shown that the AIP-generated VMAT plans resulted in significantly better rectum sparing than the IMRT plans using the standard 8-beam configuration currently being utilized. When more gantry angles were added to the IMRT plans, the VMAT plan quality was still consistently better until the number of beams in IMRT reached 12-16 beams. At this point, which varied among the patients examined, the IMRT plan quality became similar to or slightly better than that of VMAT. Beyond this point, the plan quality of IMRT does not improve noticeably further even if more beams are used. This indicates that, for prostate cancer, the plan quality of VMAT is a limit to which the plan quality of IMRT converges as increasing numbers of beams are used.

From another perspective, these results demonstrate that the difference in the plan quality of VMAT and IMRT is due to the difference in the number of beam angles and the level of modulation from each angle used in the two modalities. These results show that having a large number of beam angles but few modulations (control points) from each angle is superior (in terms of plan quality) to having many modulations from each angle but a small number of beam angles. However, a large number of modulations from many beam angles in IMRT may compensate for the insufficient number of beams and produce a plan quality similar to that of VMAT, when the number of beams in IMRT is sufficiently large.

Because the in-house AIP algorithm was developed to generate treatment plans with optimal plan quality, all the AIP-generated plans in this example have the best quality that can be achieved, which enabled us to perform a fair comparison of the two modalities. A quality control (QC) method was applied that was recently published by Moore et al. (31) in evaluating the quality of plans involved in this example. It was found that the rectum dose measured from the AIP-generated plans is consistently close to the "best organ sparing" predicted by the QC model presented in the paper. The relative model excess, which gives the normalized difference between measured and predicted dose, obtained from the AIP-generated 8-field IMRT plans ranges from −0.2 to 0.22 Gy, which is within the expected range for plans after applying the QC procedure (−0.8 to 0.22 Gy). The clinically treated IMRT plans have also resulted in a similar range. This result shows that both the clinical and the AIP-generated IMRT plans have achieved similar level of rectum sparing as the well-quality-controlled plans. For IMRT plans with a larger number of beams, the algorithm optimizes the plan in the same way as it does for 8-field IMRT which was expected to generate the same high level of plan quality for these beam configurations.

The AIP-generated VMAT plans generated in this example resulted in considerably higher MU usage than the 8-beam IMRT plans, which is inconsistent with the results reported by other groups, who have found that VMAT plans usually reduce MU usage compared to IMRT plans (3, 10, 12, 13, 16, 17). For studies conducted in the Varian planning system (3, 16), the significant reduction in MU usage of VMAT probably comes from the difference in the optimization algorithms used for VMAT and IMRT. Comparing to studies conducted in Pinnacle (12, 13), the discrepancy may be due to the fact that, in the AIP algorithm, the focus was on improving the plan quality, especially by reducing the rectum dose, so that achievable optimal plans were generated but not plans with higher delivery efficiency or lower MU usage. Higher MU usage resulting from the plans may be a consequence of their highly conformal dose distributions and their superior OAR sparing. To confirm this, a VMAT plan was manually designed for one patient using a set of objectives that has loose dose constraints for the rectum and bladder compared to those used in the AIP algorithm. This manual VMAT plan resulted in dramatically reduced MU usage (363 MU) compared to that of the corresponding AIP-generated VMAT plan (1038 MU), but it also resulted in inferior OAR sparing (FIG. 10). As far as delivery time is concerned, the 1038-MU plan took only 10% longer to deliver than the 363-MU plan. Admittedly, higher MU has its drawbacks such as the potential increase in total body dose because of scattering and leakage from MLCs (32).

Figure 43:
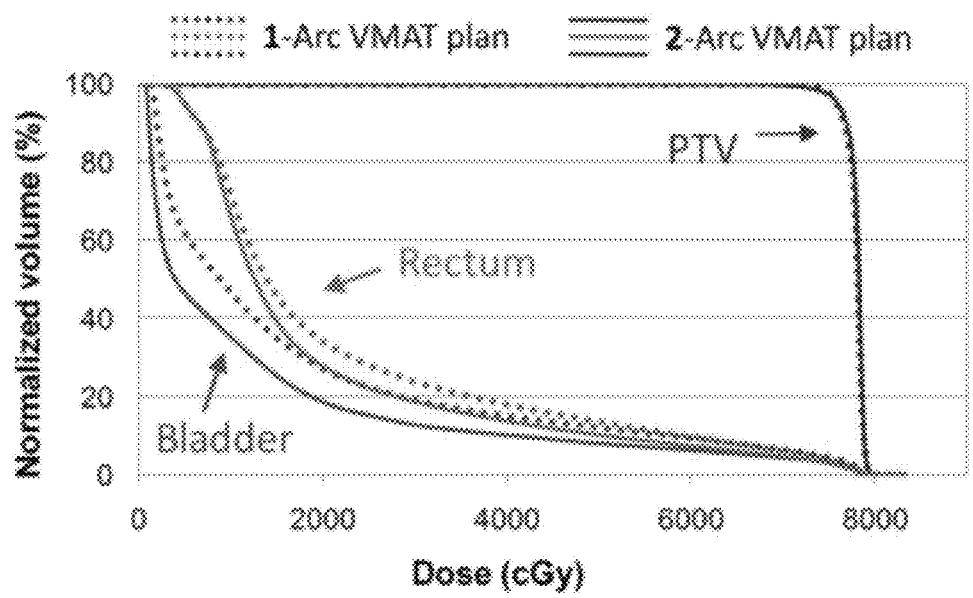
FIG. 43 is dose-volume histograms of the PTV, rectum, and bladder from the single- and dual-arc VMAT plans for a typical patient.

All the VMAT plans generated in this example used two 360° arcs instead of one 360° arc because it was found that dual-arc is superior to single-arc in terms of the compromise between plan quality and delivery efficiency. FIG. 43 shows the typical DVH plots of a single-arc and a dual-arc VMAT plan. Dual-arc produced better rectum and bladder sparing than single-arc. In fact, dual-arc VMAT plans typically used less than 15% more total MUs than single-arc VMAT plans. Therefore, in this example dual-arc VMAT plans were used for the comparison with IMRT.

The effect of the number of beams on plan quality has been previously studied by Pirzkall et al., using a completely different approach from ours, who found that less than 9 beams may result in increased dose in regions far away from the target. In their work, all IMRT plans were generated "using the same dose-volume constraints" (33). In contrast, every plan in this example was generated completely independently from other plans. Specifically, the objective function parameters of every plan were optimized for each beam angle configuration, ensuring a high plan quality of each case.

This suggests the effectiveness of the AIP algorithm for prostate cancer treatment planning. For the few manually-designed clinical VMAT plans that were available, the AIP-generated VMAT plans produced at least a comparable plan quality. The AIP algorithm also consistently produced IMRT plans that were comparable, if not superior, to the dosimetrists' manual IMRT plans with the same beam angle configurations for all patients that were examined.

One might argue that IMRT with a large number of beams (>8) is not clinically practical considering its lower delivery efficiency. In this example, IMRT with a larger number of fields was used to obtain a better understanding of the capability of IMRT and the differences between IMRT and VMAT plan quality. Furthermore, novel technologies that enable the more efficient delivery of fixed-field IMRT, such as the one used in the TrueBeam system (Varian Medical Systems, Palo Alto, Calif.), and continuing improvements in IMRT delivery techniques will make it possible to deliver IMRT plans with a large number of beams more efficiently in the near future, to continue to expand understanding of this modality.

This shows that the VMAT technique combined with the in-house AIP algorithm generates significantly superior plans compared to the 8-beam clinical IMRT plans used for prostate cancer treatment. For IMRT plan quality to be improved such that it is comparable to that of an optimized VMAT plan, a sufficiently large number of beams has to be used. However, this would come at the expense of even longer dose delivery, increased treatment times (leading to increased intra-fractional motion) and higher economic cost. Considering the superior delivery efficiency of VMAT and the fact that the optimized VMAT plan quality in terms of both DVH and conformality of dose distribution well exceeds that of clinical IMRT plans, VMAT may be the preferred modality for treating prostate cancer.

REFERENCES

All references listed below are hereby incorporated by reference in full.

Xiaodong Zhang et al. Phys. Med. Biol. 56 (2011) 3873-3893.

Allen, A. M. and E. H. Baldini (2007). "In regards to Allen et al. (Int J radiat oncol biol phys 2006; 65: 640-645)-Reply." International Journal of Radiation Oncology Biology Physics 68(1): 316-316.

Allen, A. M., M. Czerminska, et al. (2006). "Fatal pneumonitis associated with intensitymodulated radiation therapy for mesothelioma." International Journal of Radiation Oncology Biology Physics 65(3): 640-645.

Allen, A. M., D. Schofield, et al. (2007). "Restricted field imrt dramatically enhances IMRT planning for mesothelioma." International Journal of Radiation Oncology Biology Physics 69(5): 1587-1592.

Chang, J. Y., X. D. Zhang, et al. (2006). "Significant reduction of normal tissue dose by proton radiotherapy compared with three-dimensional conformal or intensity-modulated radiation therapy in Stage I or Stage III non-small-cell lung cancer." International Journal of Radiation Oncology Biology Physics 65(4): 1087-1096.

Chung, H. T., B. Lee, et al. (2008). "Can all centers plan intensity-modulated radiotherapy (IMRT) effectively? An external audit of dosimetric comparisons between three-dimensional conformal radiotherapy and IMRT for adjuvant chemoradiation for gastric cancer." International Journal of Radiation Oncology Biology Physics 71(4): 1167-1174.

D'Souza, W. D., H. H. Zhang, et al. (2008). "A nested partitions framework for beam angle optimization in intensity-modulated radiation therapy." Physics in Medicine and Biology 53(12): 3293-3307.

Forster, K. M., W. R. Smythe, et al. (2003). "Intensity-modulated radiotherapy following extrapleural pneumonectomy for the treatment of malignant mesothelioma: Clinical implementation." International Journal of Radiation Oncology Biology Physics 55(3): 606-616.

Komaki, R., Z. X. Liao, et al. (2006). "Fatal pneumonitis associated with intensity-modulated radiation therapy for mesothelioma: In regard to Allen et al. (Int J Radiat Oncol Biol Phys 2006; 65: 640-645)." International Journal of Radiation Oncology Biology Physics 66(5): 1595-1596.

Liao, Z. X., J. D. Cox, et al. (2007). "Assessing the impact of technological advancement on outcome for patients with unresectable locally advanced non-small cell lung cancer (NSCLC) receiving concomitant chemoradiotherapy." International Journal of Radiation Oncology Biology Physics 69(3): S160-S161.

Liu, H. H., M. Jauregui, et al. (2006). "Beam angle optimization and reduction for intensitymodulated radiation therapy of non-small-cell lung cancers." International Journal of Radiation Oncology Biology Physics 65(2): 561-572.

Meedt, G., M. Alber, et al. (2003). "Non-coplanar beam direction optimization for intensitymodulated radiotherapy." Physics in Medicine and Biology 48(18): 2999-3019.

Potrebko, P. S., B. M. C. McCurdy, et al. (2008). "Improving intensity-modulated radiation therapy using the anatomic beam orientation optimization algorithm." Medical Physics 35(5): 2170-2179.

Pugachev, A. and L. Xing (2002). "Incorporating prior knowledge into beam orientaton optimization in IMRT." International Journal of Radiation Oncology Biology Physics 54(5): 1565-1574.

Rodrigues, G. B. and W. H. Roa (2007). "In regard to Allen et al.: Fatal pneumonitis associated with intensity-modulated radiation therapy for mesothelioma (Int J Radiat Oncol Biol Phys 2006; 65: 640-645)." International Journal of Radiation Oncology Biology Physics 68(3):959-959.

Stein, J., R. Mohan, et al. (1997). "Number and orientations of beams in intensity-modulated radiation treatments." Medical Physics 24(2): 149-160. Veldeman, L., I. Madani, et al. (2008). "Evidence behind use of intensity-modulated radiotherapy: a systematic review of comparative clinical studies." Lancet Oncology 9(4): 367-375.

Wang, X. C., X. D. Zhang, et al. (2005). "Effectiveness of noncoplanar IMRT planning using a parallelized multi-resolution beam angle optimization method for paranasal sinus carcinoma." International Journal of Radiation Oncology Biology Physics 63(2): 594-601.

Wang, X. C., X. D. Zhang, et al. (2004). "Development of methods for beam angle optimization for IMRT using an accelerated exhaustive search strategy." International Journal of Radiation Oncology Biology Physics 60(4): 1325-1337.

X. G. Wu, Y. P. Zhu, and L. M. Luo, "Linear programming based on neural networks for radiotherapy treatment planning," Phys. Med. Biol. 45, 719-728 (2000).

I. I. Rosen et al., "Treatment plan optimization using linear-programming," Med. Phys. 18, 141-152 (1991).

M. Langer et al., "Comparison of mixed integer programming and fast simulated annealing for optimizing beam weights in radiation therapy," Med. Phys. 23, 957-964 (1996).

E. K. Lee, T. Fox, and I. Crocker, "Optimization of radiosurgery treatment planning via mixed integer programming," Med. Phys. 27, 995-1004 (2000).

T. Bortfeld et al., "Methods of image-reconstruction from projections applied to conformation radiotherapy," Phys. Med. Biol. 35, 1423-1434 (1990).

T. Bortfeld, "Optimized planning using physical objectives and constraints," Semin Radiat. Oncol. 9, 20 (1999).

P. S. Cho et al., "Optimization of intensity modulated beams with volume constraints using two methods: Cost function minimization and projections onto convex sets," Med. Phys. 25, 435-443 (1998).

T. Holmes et al., "A unified approach to the optimization of brachytherapy and external beam dosimetry," Int. J. Radiat. Oncol., Biol., Phys. 20, 859-873 (1991).

D. Hristov et al., "On the implementation of dose-volume objectives in gradient algorithms for inverse treatment planning," Med. Phys. 29, 848-856 (2002).

G. Starkschall, A. Pollack, and C. W. Stevens, "Treatment planning using a dose-volume feasibility search algorithm," Int. J. Radiat. Oncol., Biol., Phys. 49, 1419-1427 (2001).

Q. W. Wu and R. Mohan, "Algorithms and functionality of an intensity modulated radiotherapy optimization system," Med. Phys. 27, 701-711 (2000).

Q. Hou and Y. G. Wang, "Molecular dynamics used in radiation therapy," Phys. Rev. Lett. 8716, 168101 (2001).

Q. Hou et al., "An optimization algorithm for intensity modulated radiotherapy—The simulated dynamics with dose-volume constraints," Med. Phys. 30, 61-68 (2003).

S. M. Morrill et al., "Treatment planning optimization using constrained simulated annealing," Phys. Med. Biol. 36, 1341-1361 (1991).

I. I. Rosen et al., "Comparison of simulated annealing algorithms for conformal therapy treatment planning," Int. J. Radiat. Oncol., Biol., Phys. 33, 1091-1099 (1995).

S. Webb, "Optimization of conformal radiotherapy dose distributions by simulated annealing. Inclusion of scatter in the 2d technique," Phys. Med. Biol. 36, 1227-1237 (1991).

X. G. Wu et al., "Selection and determination of beam weights based on genetic algorithms for conformal radiotherapy treatment planning," Phys. Med. Biol. 45, 2547-2558 (2000).

T. Bortfeld et al., "Physical vs biological objectives for treatment plan optimization," Radiother. Oncol. 40, 185-185 (1996).

M. Langer et al., "Large-scale optimization of beam weights under dosevolume restrictions," Int. J. Radiat. Oncol., Biol., Phys. 18, 887-893 (1990).

Q. W. Wu et al., "Optimization of intensity-modulated radiotherapy plans based on the equivalent uniform dose," Int. J. Radiat. Oncol., Biol., Phys. 52, 224-235 (2002).

A. Holder, "Designing radiotherapy plans with elastic constraints and interior point methods," Mathematics Technical Report, Trinity Univ., San Antonio, Tex. (2000).

A. Holder, "Radiotherapy treatment design and linear programming," Trinity University, San Antonio (2002).

S. V. Spirou and C. S. Chui, "A gradient inverse planning algorithm for conformal with dose-volume constraints," Med. Phys. 25, 321-333 (1998).

M. F. Moller, "A scaled conjugate-gradient algorithm for fast supervised learning," Neural Networks 6, 525-533 (1993).

J. O. Deasy, "Multiple local minima in radiotherapy optimization problems with dose-volume constraints," Med. Phys. 24, 1157-1161 (1997).

Q. W. Wu and R. Mohan, "Multiple local minima in IMRT optimization based on dose-volume criteria," Med. Phys. 29, 1514-1527 (2002).

J. Llacer et al., "Absence of multiple local minima effects in intensity modulated optimization with dose-volume constraints," Phys. Med. Biol. 48, 183-210 (2003).

C. G. Rowbottom and S. Webb, "Configuration space analysis of common cost functions in radiotherapy beam-weight optimization algorithms," Phys. Med. Biol. 47, 65-77 (2002).

M. Alber et al., "On the degeneracy of the IMRT optimization problem," Med. Phys. 29, 2584-2589 (2002).

R. Jeraj, C. A. Wu, and T. R. Mackie, "Optimizer convergence and local minima errors and their clinical importance," Phys. Med. Biol. 48, 2809-2827 (2003).

C. Wu, R. Jeraj, and T. R. Mackie, "The method of intercepts in param-eter, space for the analysis of local minima caused by dose-volume constraints," Phys. Med. Biol. 48, N149-N157 (2003).

A. Niemierko, "Reporting and analyzing dose distributions: A concept of equivalent uniform dose," Med. Phys. 24, 103-110 (1997).

W. H. Press, W. T. Vetterling, and B. P. Flannery, Numerical Recipes in C: The Art of Scientific Computing, 2nd ed. (Cambridge University Press, Cambridge, 1992).

Q. W. Wu et al., "A fast dose calculation method based on table lookup for IMRT optimization," Phys. Med. Biol. 48, N159-N166 (2003).

Edward C. Halperin, Carlos A. Perez, Luther W. Brady. Perez and Brady's Principles and Practice of Radiation Oncology, Lippincott Williams & Wilkins, 2008.

Eric K. Hansen, Mack Roach. Handbook of evidence-based radiation oncology, Springer, 2006.

S. Soderstrom, et al., "Which is the Most Suitable Number of Photon Beam Portals in Coplanar Radiation Therapy", International Journal of Radiation Oncology, Biology, Physics, Vol. 33, 1995, pp. 151-159.

G. A. Ezzell, "Genetic and Geometric Optimization of Three-Dimensional Radiation Therapy Treatment Planning", Medical Physics, Vol. 23, 1996, pp. 293-305.

P. Gokhale, et al., "Determination of Beam Orientations in Radiotherapy Planning", Medical Physics, Vol. 21, 1994, pp. 393-400.

M. E. Hosseini-Ashrafi, et al., "Pre-optimization of Radiotherapy Treatment Planning: An Artificial Neural Network Classification Aided Technique" Physics in Medicine and Biology, Vol. 44, 1999, pp. 1513-1528.

C. G. Rowbottom, et al., "Beam Orientation Customization using an Artificial Neural Network", Physics in Medicine and Biology, Vol. 44, 1999, pp. 2251-2262.

B. C. J. Cho, et al., The Development of Target-Eye-View Maps for Selection of Coplanar or Noncoplanar Beams in Conformal Radiotherapy Treatment Planning", Medical Physics, Vol. 26, 1999, pp. 2367-2372.

S. K. Das, et al., "Selection of Coplanar or Noncoplanar Beams using Three-dimensional Optimization Based on Maximum Beam Separation and Minimized Non-Target Irradiation", International Journal of Radiation Oncology, Biology, Physics, Vol. 38, 1997, pp. 643-655.

D. L. McShan, et al., "Advanced Interactive Planning Techniques for Conformal Therapy: High Level Beam Description and Volumetric Mapping Techniques", International Journal of Radiation Oncology, Biology, Physics, Vol. 33, 1995, pp. 1061-1072.

C. G. Rowbottom, et al., "Constrained Customization of Noncoplanar Beam Orientations in Radiotherapy of Brain Tumors", Physics in Medicine and Biology, Vol. 44, 1999, pp. 383-399.

S. L. Sailer, et al., "The Tetrad and Hexad: Maximum Beam Separation as a Starting Point for Noncoplanar 3D Treatment Planning: Prostate Cancer as a Test Case", International Journal of Radiation Oncology, Biology, Physics, Vol. 30, 1994, pp. 439-446.

G. T. Y. Chen, et al., "The use of Beam's Eye View Volumetrics in the Selection of Noncoplanar Radiation Portals", International Journal of Radiation Oncology, Biology, Physics, Vol. 23, 1992, pp. 153-163.

H.-M. Lu, et al., "Optimized Beam Planning for Linear Accelerator-Based Stereotactic Radiosurgery", International Journal of Radiation Oncology, Biology, Physics, Vol. 39, 1997, pp. 1183-1189.

M. Goitein, et al., "Multi-dimensional Treatment Planning: II. Beam's Eye-View, Back Projection, and Projection through CT Sections", International Journal of Radiation Oncology, Biology, Physics, Vol. 9, 1983, pp. 789-797.

and Carl Graham, et al., "Improvements in Prostate Radiotherapy from the Customization of Beam Directions", Medical Physics, Vol. 25, 1998, pp. 1171-1179.

Beam orientation selection in IMRT is discussed in the following references: J. Stein, et al., "Number and Orientations of Beams in Intensity-Modulated Radiation Treatments", Medical Physics, Vol. 24, 1997, pp. 149-160.

M Asell, et al., "Optimal Electron and Combined Electron and Photon Therapy in the Phase Space of Complication-Free Cure", Physics in Medicine and Biology, Vol. 44, 1999, pp. 235-252.

T. Bortfield and W. Schlegel, "Optimization of Beam Orientations in Radiation Therapy: Some Theoretical Considerations", Physics in Medicine and Biology, Vol. 38, 1993, pp. 291-304.

A. Pugachev, et al., "Beam Orientations in IMRT: To Optimize or not to Optimize?", The Use of Computers in Radiation Therapy, XIII ICCR, 2000, pp. 37-39.

S. Soderstrom and A. Brahme, "Selection of Suitable Beam Orientations in Radiation Therapy using Entropy and Fourier Transform Measures", Physics in Medicine and Biology, Vol. 37, 1992, pp. 911-924.

A. Pugachev, A. Boyer, L. Xing, "Beam Orientation Optimization in Intensity-Modulated Radiation Treatment Planning", Medical Physics, Vol. 27, 2000, pp. 1238-1245.

M. Braunstein, et al., "Optimum Beam Configurations in Tomographic Intensity Modulated Radiation Therapy", Physics in Medicine and Biology, Vol. 45, 2000, pp. 305-328.

What is claimed is:

1. A method of forming a treatment plan for treating a patient with radiation therapy, the method comprising:
   receiving information corresponding to a tumor position in the patient determined using an imaging device;
   selecting a plurality of beam angles for a respective plurality of beams based on the tumor position;
   receiving information corresponding to a plurality of constrained and unconstrained objective function parameters related to at least one of a minimum and maximum radiation dosage to a specific region of interest;

selecting an intensity for each beam based, in part, on the objective function parameters;

selecting new unconstrained objective function parameters based, in part, on previous unconstrained objective function parameters; and selecting new beam intensities based, in part, on the new unconstrained objective function parameters, wherein selecting new unconstrained objective function parameters comprises:

calculating a value of a sub-objective function;

comparing the value of the sub-objective function to a user-defined maximum sub-objective function value; and adjusting a value of an objective function parameter if the value of the sub-objective function is less than the user-defined maximum sub-objective function value.

2. The method of claim 1, wherein the new beam intensities are selected more than twice.

3. The method of claim 1, wherein the plurality of beams are used to treat a patient in need of radiation therapy.

4. The method of claim 1, wherein the plurality of beam angles are selected using an expert system.

5. The method of claim 4, wherein the expert system includes information on a plurality of patients' tumor position, tumor size, general tumor site and beam angles used to treat the plurality of patients' tumor position.

6. The method of claim 4, wherein beam angles are selected using expert system beam angles used to treat a tumor location in a patient in the expert system who has the closest tumor location to the tumor position.

7. The method of claim 4, wherein the selected beam angles are selected from beam angles with a highest frequency distribution in a set of patients in the expert system with tumor locations in the general organ location of the tumor position.

8. The method of claim 7, wherein the treatment plan comprises multiple treatments.

9. The method of claim 8, wherein after a treatment within the multiple treatments, new information corresponding to the tumor position is received and new beam angles selected from the expert system.

10. The method of claim 8, wherein after a treatment within the multiple treatments, new information corresponding to the tumor position is received and new objective functional parameters are selected.

11. The method of claim 1, wherein a tumor position is a relative coordinate between a marked iso-center of a tumor and the center of a planning target volume.

12. The method of claim 1, wherein at least one objective function parameter is represented by an objective function parameter value calculated using Equivalent Uniform Dose (EUD), Tumor Control Probability (TCP), Normal Tissue Complication Probability (NTCP), dose and dose-volume.

13. The method of claim 1, wherein the method additionally comprises removing at least one beam and selecting new beam intensities for the remaining beams.

14. The method of claim 13, wherein the method additionally comprises comparing the treatment plan before and after removing the at least one beam; and adding the removed beam back into the treatment plan if the selected new beam intensities results in a total objective function value greater than a previous total objective function value.

15. The method of claim 1, wherein the tumor position is represented by an integrated target volume.

16. The method of claim 15, wherein the method additionally comprises:

estimating a mean organ dose based on the tumor size and overlapping between tumor and normal organ;

determining if the mean organ dose is above or below a set value;

using the integrated target volume tumor position to select the new objective function parameters if the mean organ dose is above the set value.

17. The method of claim 1, wherein the objective function parameters are selected from the group consisting of planning target volume minimum dose, planning target volume uniform dose, planning target volume maximum dose, minimum planning target dose volume, maximum planning target dose volume, organ avoidance maximum dose, maximum organ avoidance dose volume, and any combination thereof.

18. The method of claim 1, wherein constrained objection function parameters are selected from the group consisting of planning target volume minimum dose, planning target volume maximum dose, planning target volume dose, maximum normal tissue dose, maximum cord dose volume, and any combination thereof.

19. The method of claim 1, wherein regions of interest are selected from a group consisting of the tumor location, any organ located near the tumor location, and any combination thereof.

20. The method of claim 1, wherein the radiation therapy is selected from the group consisting of intensity modulated radiation treatment, intensity modulated proton therapy treatment, and volumetric modulated arc therapy.

21. The method of claim 1, wherein an objective function parameter is represented by the parameters: equivalent uniform dose (EUD0), dose, dose-volume, weight, and alpha.

22. The method of claim 1, wherein the method is repeated until a total objective value calculated from the sum of the individual objective function parameters is the same as or greater than a previous total objective value.

23. The method of claim 1, wherein multiple treatment plans are generated by weighing each objective functional parameter differently.

24. The method of claim 23, wherein the multiple treatment plans are Intensity-Modulated Radiation Therapy (IMRT) plans and a final treatment plan is a Volumetric-Modulated Arc Therapy (VMAT) plan.

25. The method of claim 23, wherein at least two of the multiple treatment plans are combined to produce a final treatment plan.

26. The method of claim 1, wherein a final treatment plan is an Intensity-Modulated Radiation Therapy (IMRT) plan or a Volumetric-Modulated Arc Therapy (VMAT) plan.

27. A system for generating treatment plans for radiation therapy, the system comprising a processor in communication with a memory, where the memory stores processor-executable program code and the processor is configured to be operative in conjunction with the processor-executable program code to:

receive information corresponding to a tumor position in the patient determined using an imaging device;

select a plurality of beam angles for a respective plurality of beams based on the tumor position;

receive information corresponding to a plurality of constrained and unconstrained objective function parameters related to at least one of a minimum and maximum radiation dosage to a specific region of interest;

select an intensity for each beam based, in part, on the objective function parameters;

select new unconstrained objective function parameters based, in part, on previous unconstrained objective function parameters; and select new beam intensities based, in part, on the new unconstrained objective function parameters, wherein selecting new unconstrained objective function parameters comprises:

calculating a value of a sub-objective function;

comparing the value of the sub-objective function to a user-defined maximum sub-objective function value; and adjusting a value of an objective function parameter if the value of the sub-objective function is less than the user-defined maximum sub-objective function value.

28. The system of claim 27, further comprising selecting a best compromised plan based on multiple plans.

29. A non-transitory computer readable medium comprising computer-usable program code executable to perform operations comprising:

receiving information corresponding to a tumor position in the patient determined using an imaging device;

selecting a plurality of beam angles for a respective plurality of beams based on the tumor position;

receiving information corresponding to a plurality of constrained and unconstrained objective function parameters related to at least one of a minimum and maximum radiation dosage to a specific region of interest;

selecting an intensity for each beam based, in part, on the objective function parameters;

selecting new unconstrained objective function parameters based, in part, on previous unconstrained objective function parameters; and selecting new beam intensities based, in part, on the new unconstrained objective function parameters, wherein selecting new unconstrained objective function parameters comprises:

calculating a value of a sub-objective function;

comparing the value of the sub-objective function to a user-defined maximum sub-objective function value; and adjusting a value of an objective function parameter if the value of the sub-objective function is less than the user-defined maximum sub-objective function value.

* * * * *